US010888270B2

(12) United States Patent
Abrahami et al.

(10) Patent No.: US 10,888,270 B2
(45) Date of Patent: Jan. 12, 2021

(54) COGNITIVE STATE ALTERATION SYSTEM INTEGRATING MULTIPLE FEEDBACK TECHNOLOGIES

(71) Applicants: Avishai Abrahami, Tel Aviv (IL); Eli Bar Yosef, Tel Aviv (IL)

(72) Inventors: Avishai Abrahami, Tel Aviv (IL); Eli Bar Yosef, Tel Aviv (IL)

(*) Notice: Subject to any disclaimer, the term of this patent is extended or adjusted under 35 U.S.C. 154(b) by 0 days.

(21) Appl. No.: 15/230,449

(22) Filed: Aug. 7, 2016

(65) Prior Publication Data

US 2017/0039045 A1 Feb. 9, 2017

Related U.S. Application Data

(60) Provisional application No. 62/201,749, filed on Aug. 6, 2015.

(51) Int. Cl.
*A61B 5/00* (2006.01)
*A61B 5/11* (2006.01)
*A61B 5/0205* (2006.01)

(52) U.S. Cl.
CPC ............ *A61B 5/486* (2013.01); *A61B 5/0205* (2013.01); *A61B 5/1118* (2013.01); *A61B 2505/09* (2013.01)

(58) Field of Classification Search
CPC ............. G06F 2221/2133; G06F 19/30; G06F 19/324; G06F 19/325; G06F 19/34;
(Continued)

(56) References Cited

U.S. PATENT DOCUMENTS 8,517,912 B2    8/2013  Clare
8,972,324 B2 *  3/2015  Reddy ................. G06N 3/008
                                        706/46
(Continued)

FOREIGN PATENT DOCUMENTS

WO    2007025120    3/2007
WO    2007103835    9/2007
WO    2014107795    7/2014

OTHER PUBLICATIONS

Chris Wilson; An Agent for Simulating Cognitive Impairment in Elders; ADS; 5 pages; retrieved on Sep. 28, 2020. (Year: 2014).*
(Continued)

*Primary Examiner* — S. Sough
*Assistant Examiner* — Cuong V Luu
(74) *Attorney, Agent, or Firm* — Heidi Brun Associates Ltd.

(57) ABSTRACT

A cognitive alteration system includes a storage unit at least to store one or more scripts, each to control a cognitive alteration process where the process comprises first and second in session media-based treatment processes and an out of session reinforcement stimulus process between the first and second in session processes, and where the storage unit stores both a script per in session process and a script per out of session process; a script handler at least to run at least one script; at least one of a wearable and a non-wearable element to sense an attribute of a subject or to provide an output to the subject during one of the in session and out of session processes; an information analyzer at least to perform analysis of the readings of the at least one element, an integrator to integrate the analysis and a script updater to update at least one of the scripts.

28 Claims, 14 Drawing Sheets

(58) Field of Classification Search
CPC ....... G06F 1/163; A61B 5/486; A61B 5/0205; A61B 5/1118; A61B 2505/09; A61B 5/4836; A61B 5/0022; A61B 5/742
See application file for complete search history.

(56) References Cited

U.S. PATENT DOCUMENTS

| | | | |
|---|---|---|---|
| 9,089,691 B2 | 7/2015 | Libbus et al. | |
| 9,248,286 B2 | 2/2016 | Simon et al. | |
| 9,729,631 B2* | 8/2017 | Addala | H04L 67/1095 |
| 10,111,611 B2* | 10/2018 | el Kaliouby | A61B 5/165 |
| 2009/0099623 A1* | 4/2009 | Bentwich | A61N 1/36025 |
| | | | 607/45 |
| 2009/0198145 A1 | 8/2009 | Chow | |
| 2010/0010371 A1* | 1/2010 | Zayfert | G16H 20/70 |
| | | | 600/558 |
| 2011/0190594 A1 | 8/2011 | Heit | |
| 2011/0289484 A1* | 11/2011 | Caine | G06F 8/30 |
| | | | 717/127 |
| 2013/0266924 A1 | 10/2013 | Zelin | |
| 2014/0032467 A1* | 1/2014 | Reddy | G06N 99/005 |
| | | | 706/46 |
| 2014/0057232 A1* | 2/2014 | Wetmore | A61B 5/0036 |
| | | | 434/236 |
| 2014/0303425 A1* | 10/2014 | Pilla | A61B 6/037 |
| | | | 600/14 |
| 2014/0323817 A1* | 10/2014 | el Kaliouby | A61B 5/165 |
| | | | 600/300 |
| 2014/0330896 A1* | 11/2014 | Addala | G06F 17/3089 |
| | | | 709/203 |
| 2015/0112409 A1* | 4/2015 | Hagedorn | A61B 5/0006 |
| | | | 607/62 |

OTHER PUBLICATIONS

Elliot Cole et al.; Computer-Based Cognitive Prosthetics Assistive technology for the Treatment of Cognitive Disabilities; Assets; pp. 11-18; retrieved on Sep. 28, 2020 (Year: 1998).*
"A Realtime and Continuous Assessment of Cortisol in ISF Using Electrochemical Impedance Spectroscopy" by Venugopal M, Arya SK, Chornokur G, Bhansali S. Sens Actuators A Phys. Dec. 1, 2011;172(1):154-160. http://www.ncbi.nlm.nih.gov/pubmed/22163154.
International Search Report for corresponding PCT application PCT/IB2016/095003 dated Jan. 23, 2018.
Supplementary European Search Report for corresponding European application 16 83 2413.5 dated Jul. 16, 2018.

* cited by examiner

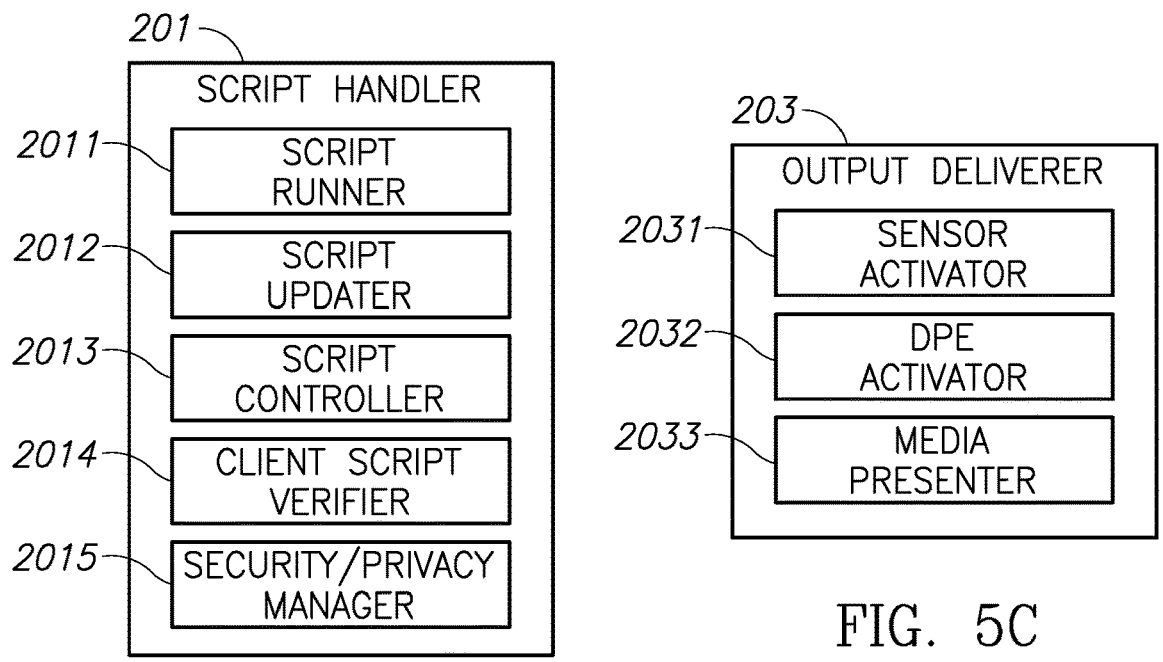
FIG. 5B
FIG. 5C
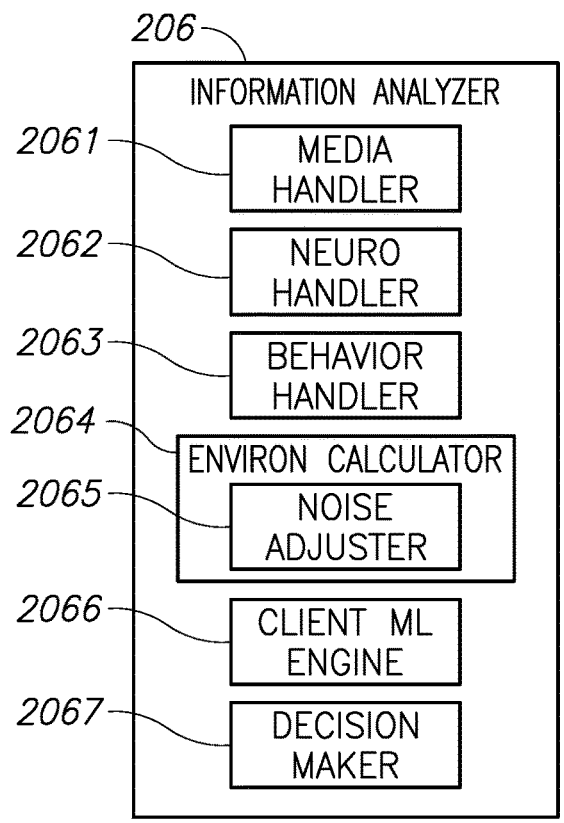
FIG. 5D

COGNITIVE STATE ALTERATION SYSTEM INTEGRATING MULTIPLE FEEDBACK TECHNOLOGIES

CROSS REFERENCE TO RELATED APPLICATIONS

This application claims priority from U.S. Provisional Patent Application 62/201,749 filed Aug. 6, 2015 which is hereby incorporated herein by reference.

FIELD OF THE INVENTION

The present invention relates to cognitive treatment systems generally and to systems with integrated feedback technologies in particular.

BACKGROUND OF THE INVENTION

Cognitive state alteration techniques have been used throughout history to help people in improving various areas of their life, in solving specific problem affecting the life or well-being of a person, as well as for achieving specific goals.

Typical areas and goals include performance improvement (e.g. in sports), concentration, weight loss, smoking cessation, pain reduction, stress reduction, behavior modification, sleeps disorders (sleep deprivation and deficiency) and many more.

Cognitive state alteration techniques have mainly been used in two modes: therapeutic and self-induced.

In therapeutic mode, a therapist interacts with the subject, performing a therapeutic session to achieve the desired results. A primary example of such mode is a hypnosis session performed by a hypnotherapist, but this may also be a part of psychoanalysis or psychotherapeutic session.

In self-induced mode, a person performs the required actions by himself or herself, without the involvement of a human therapist. Examples include the use of self-hypnosis and some forms of meditation, as well as the use of specialized systems (such as the one described in this application) to achieve the desired cognitive state alteration as well as the desired goals.

Cognitive state alteration techniques are usually performed during a specific uninterrupted session (i.e. the subject is focused on and dedicated to performing the session). This is known as the "in session" period. However, the desired effects (behavioral change, reduced anxiety etc.) should also affect the regular day to day routine of the subject i.e. during the "out of session" period.

It will be appreciated that the session duration of the "in session" period is not the same as the trance period (as described in more detail herein below), since a session may include multiple stages, some of which are not spent in hypnotic trance state, notably the pre-trance relaxation stage and the post-trance awakening stage.

The human mind may function in multiple and different states of consciousness. Some of them occur naturally, such as the regular (fully awake and aware) state, or the state of regular sleep, and some will only occur when artificially induced. Some are very common, and some occur less often, such as day-dreaming with an associated lowered awareness.

Some of the states may further be divided into sub-states which may be divided even further. For example, the sleeping state may be divided into REM (Rapid-Eye Movement) sleep and NREM (non-REM) sleep with NREM further sub-divided into multiple sub-states (such as NREM stage 1 (drowsy), NREM stage 2 (sleep) and NREM stage 3 (deep sleep also known as Slow Wave Sleep (SWS). An alternative analysis (used by some sources) separates NREM stage 3 from NREM stage 4 (SWS), with the latter being characterized by a higher level of delta waves. These stages are further described herein below.

Some states occur only under specific inducement or conditions, such as the states entered by using some mind-affecting drugs. For example, the state known as "highway hypnosis" can only occur when driving a familiar route. In this state, a person can drive great distances, driving perfectly, but without remembering doing so.

A person is typically in a given state at any given time, but may transition to another state. Some transitions are very easy (e.g., a person who is daydreaming or focuses on a task may be easily distracted by external noise) whereas some transitions are difficult to achieve (e.g., it may take a long time for a person to actually fall asleep). The methods and amount of effort required to transition into a given state may vary between different individuals, some people fall asleep easily, and some take hours to do so. Furthermore, the effort involved in state transitioning may vary for a given individual, e.g. the effort to fall asleep may very well depend on how tired the person is.

Hypnosis, or hypnotic trance, is another state of consciousness involving focused attention and reduced peripheral awareness, and characterized by an enhanced capacity for response to suggestion. Thus, hypnosis can be used (e.g. in a hypnotherapy session) for the implantation of a set of suggestions which may benefit the hypnotized subject in various life areas such as motivation, sleep, weight loss, smoking cessation etc.

Hypnosis is usually induced by a procedure known as a hypnotic induction involving a series of preliminary instructions and suggestions. The implanted suggestions can be immediate (e.g. "your will feel better") or can be a future-oriented posthypnotic suggestion, affecting the subject after the hypnosis session has ended.

A posthypnotic suggestion may include a post-session behavior modification (e.g. "you will feel a reduced desire to smoke" or "you will feel less stressed when awakening") or specific actions to be performed.

The posthypnotic suggestion may be tied to a cue i.e. a specific trigger which will activate it (e.g. "whenever you touch a cigarette you will feel nauseated").

Such a suggestion may be positive (e.g. "when you start your daily training you will feel exhilarated") or aversive (e.g. the cigarette example above) in nature.

There are many levels and sub-levels of trance. Hypnosis induced trance may be shallow, deep or anywhere in between. In some levels, the hypnotized person may appear to be fully awake and aware of his or her environment, and in some levels he may appear to be fast asleep. Researchers have developed over the years numerous scales describing such different trance levels, ranging from high-level categorization to highly detailed, 100+ stage scales. Two of the most commonly used are the Harvard Group Scale of Hypnotic Susceptibility (HGSS) and the Stanford Hypnotic Susceptibility Scale (SHSS). The various scales and stages may be correlated with various hypnotic session stage structures (i.e. division into stages and sub-stages).

It will be appreciated that trance levels are not fixed or "hard wired", a specific hypnotic session structure may use specific trance levels not used by other hypnotic session structures.

Trance states are not unique to hypnosis. For example, daydreaming or the state of concentrating when reading a book and visualizing its story are also considered trance states. However, such trance states are very shallow, and do not induce a heightened response to a suggestion, whereas the hypnotic trance states are much deeper and the hypnotized person is much more sensitive to suggestions.

Typically, the complete hypnotherapy process is performed during a session which is divided into stages. A typical set of stages may include: introduction (opening the session and preparing the subject for the upcoming stages); relaxation (initial hypnotic induction causing the subject to enter a light hypnotic state), attention focusing (making the subject more focused and attentive to additional instructions), testing (to check current trance level) and deepening (when the subject transitions into a higher trance level). The stages may continue with suggestion/instruction (delivering the effective part (the "payload") of the session, e.g. the suggestions relevant to smoking cessation etc.) and awakening (when the subject returns to a normal awake state). It will be appreciated that the stages are dynamic, and some stages may be skipped, prolonged or shortened.

Furthermore, some types of hypnotherapy sessions may include stages in which the user is some type of sleep state (e.g. employing sleep stages in which the user is highly susceptible to suggestions). Some types of hypnotherapy sessions may even end with the user asleep, i.e. the user has left the trance state but is still in a normal sleep state.

During each stage the hypnotherapist (in a therapist/subject scenario) provides the appropriate instructions and induction to effect the required transition between different states of consciousness. The progress between stages is not linear, e.g. a user may return to a previous state due to (for example) interruption, non-effective instructions or problems in the instructions delivery. Furthermore, the progress between stages may lead the subject to an undesired state, such as the subject becoming over-relaxed and falling asleep, and the hypnotherapist may have to resolve the situation and move the subject back to a state more conducive to session continuation.

A session is typically performed over a contiguous time period, during which there should be no interruptions and the subject should be able to rest and relax as needed. Furthermore, the subject is typically required to be stationary during the session.

The hypnotherapist must be able to detect the state to which the subject has reached, in order to perform the appropriate steps and provide the right instructions, be it continuing with the current stage, delivering specific suggestions, advancing to the next stage, returning to a previous stage, taking some other actions or stopping the session altogether.

A single stage may include transitioning between multiple trance levels. For example, assuming a scale containing 10 different trance levels, a deepening stage (as described above) may be aimed at deepening the trance from levels 2-3 to levels 6-7 (passing through the intervening levels). Some stages might involve cognitive states which are not trance states (or levels), e.g. an awakening state may include tasks to be performed after the user has awakened and is not in a trance anymore.

There are numerous methods known in the art to detect and recognize trance levels based (for example) on externally observable phenomena (e.g. pupil dilation), measureable physiological criteria (e.g. heart rate, brain wave reading) or on the level of susceptibility of the subject to various specific suggestions. Some of these methods have been employed over the years by trained hypnotists and hypnotherapists, whereas some methods can only be employed through the use of measurement equipment (to measure some biological/biophysical aspects of the subject) or in the context of machine-based hypnosis. Detecting the current trance state of a subject may be a difficult and challenging task, and sometimes impossible for a human, in particular when a hypnotherapist is required to closely observe minute details of the subject's behavior for an extended period, and may become unfocused himself.

The hypnotherapy session is often based on a script, or a set of scripts, which detail the instructions to be provided to the subject such as any specific content or media to be displayed to the subject (e.g. audio, video, etc.) and the suggestions to be used.

The suggestions made during the dedicated "in session" period are typically used to affect the subject during the "out of session period" i.e. outside of the session itself.

Many computerized systems aimed at supporting self-induced therapy (as described here in above) have been developed over the years. The use of such systems is often more convenient, accessible and economical than the use of a dedicated hypnotherapist (who can only handle one patient at a time).

Historically, such systems started with the use of fixed pre-recorded therapeutic scripts which can be played over any audio playback device (computerized or not). They further evolved into self-hypnosis software, which included audio as well as visual stimuli.

Such systems may include such options as script customization, e.g. allowing the user to select specific script types, keywords or element progression; a pre-session questionnaire, allowing the user to provide some input data to the script (e.g. the user's name, favorite images etc.) and a post-session questionnaire, allowing the user to provide some feedback to the system on its effectiveness.

Some systems provide a degree of in-session interactivity. Regular user interaction (e.g. asking the user to provide some keyboard/mouse feedback during session) is difficult, as the user is at rest while in a trance, and may be unable to perform complex actions. Interaction may be limited to execution of simple instructions (e.g. "lift your arm when you feel fully rested"). The system may then use sensors to measure some physiological or physical parameters of the subject, and manage the session based on the input gathered from these sensors.

One of the most common such physiological sensor is EEG (Electroencephalography). EEG sensors are typically located inside a headband to be worn on the head. Many vendors produce consumer-grade EEG headbands, including NeuroSky Inc., Emotive Inc. or Interaxon Inc. (providers of the Muse headset). Such headbands have become popular, in part, due to their use with various brain training, meditation and focus improvement systems which do not employ cognitive state alteration (CSA) techniques and do not place the user in any trance level.

It will be appreciated that even after substantial research there is no definitive and easy method to determine an "EEG hypnosis signature". Some EEG patterns (e.g. the Alpha-Theta crossover) do correlate with hypnotic trance states, but are still not a definite indicator of such a state.

SUMMARY OF THE PRESENT INVENTION

There is provided, in accordance with an embodiment of the present invention, a cognitive alteration system including a storage unit at least to store one or more scripts, each to control a cognitive alteration process where the process occurs within at least one of: a dedicated session and a follow-up open time period and where the storage unit stores both a script per dedicated session and a script per follow-up open time period for the process. The system also includes a script handler at least to run at least one script from the storage unit; at least one of a wearable and a non-wearable element to sense an attribute of a subject or to provide an output to the subject during one of the dedicated session and the follow-up open time period; an information analyzer at least to perform analysis of the readings of the at least one element and to provide results of the analysis to the script runner; an integrator to integrate the analysis at least from the process in both the dedicated session and the follow-up open time period; and a script updater to update at least one of the scripts for the process according to the results of the integrator.

Moreover, in accordance with an embodiment of the present invention, the system also includes a de-briefer to collect user feedback information about the system, the at least one script and the dedicated session and follow-up open time period and where the information analyzer includes a decision maker to update at least one of the scripts for the process based on at least one of the integrated analysis and post session debriefing from the de-briefer; and a machine learner to update at least both of the scripts for the process based on subject data from any of the scripts, subject data from multiple subjects using any of the scripts and multiple subjects using scripts similar to any of the scripts.

Further, in accordance with an embodiment of the present invention, the non-wearable element is at least one of: a screen and a camera.

Still further, in accordance with an embodiment of the present invention, the wearable element is at least one of EEG, HRV, EMG, GSR, ECG, PPG.

Additionally, in accordance with an embodiment of the present invention, the script handler includes a script runner to run the at least one script and a script updater to update the scripts from updates from the machine learner, the decision maker and the integrator.

Moreover, in accordance with an embodiment of the present invention, the system also includes an event handler defining events to be responded to and an output deliverer to activate at least one of: a direct physical effect (DPE) activator, a media presenter, earphones and a wearable screen according to the scripts and in response to the events.

Further, in accordance with an embodiment of the present invention, the information analyzer includes at least one of: a media handler to handle at least delivery of media to the subject and selection and adaptation of media segments; a neurological handler to receive neurological readings and to analyze a neurological state of the subject based at least on the neurological readings; a behavior handler to monitor movements of the subject to analyze his/her behavior, to recognize gestures and to detect indicators of the psychological state of the subject; and an environment calculator to determine the state of an environment of the subject and at least to remove its effect in any readings utilized by the handlers.

Still further, in accordance with an embodiment of the present invention, the system also includes a script manager including at least one of: a script compiler to compile initial scripts; a script simulator to simulate an expected operation of a script; and an A/B test runner of the scripts to test alternate versions of the scripts before finalizing them.

Moreover, in accordance with an embodiment of the present invention, the output is at least one of: a stimulus, a media element and an instruction.

Further, in accordance with an embodiment of the present invention, the process includes at least one of: hypnosis, meditation, psychoanalysis, psychotherapeutic handling, pregnancy support, combined therapies and nerve stimulation.

Still further, in accordance with an embodiment of the present invention, the script runner transitions to a new state upon receipt of an indication of at least one of: sleep stage synchronization; pre-defined neurological states, pre-defined physiological states, timing, including calculation based on desired session length and remaining time and an intervention by at least the subject.

Additionally, in accordance with an embodiment of the present invention, the script runner transitions to a new state upon receipt of an analysis based on at least one of: user profile information, explicit subject feedback, subject's cognitive or neurological state, neurological state reading, physiological sensors reading, subject behavior detection, post-session feedback from the subject and information from other subjects.

Moreover, in accordance with an embodiment of the present invention, each transition has a transition probability associated therewith and the script updater updates the transition probabilities.

Further, in accordance with an embodiment of the present invention, the system also includes a neuro-linguistic programming (NLP) analyzer to utilize NLP-based analysis of the subject's communication with the environment to support the progress of the subject towards his/her desired goals.

Still further, in accordance with an embodiment of the present invention, the storage unit, script handler, information analyzer, integrator and script updater and de-briefer are implemented on a client/server system.

The methods implement the steps of the system.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 5B is a schematic illustration of the elements of the script handler of FIG. 5A, constructed and operative in accordance with a preferred embodiment of the present invention;

FIG. 5C is a schematic illustration of the elements of the output deliverer of FIG. 5A, constructed and operative in accordance with a preferred embodiment of the present invention;

FIG. 5D is a schematic illustration of the elements of the information analyzer of FIG. 5A, constructed and operative in accordance with a preferred embodiment of the present invention;

Figure 1:
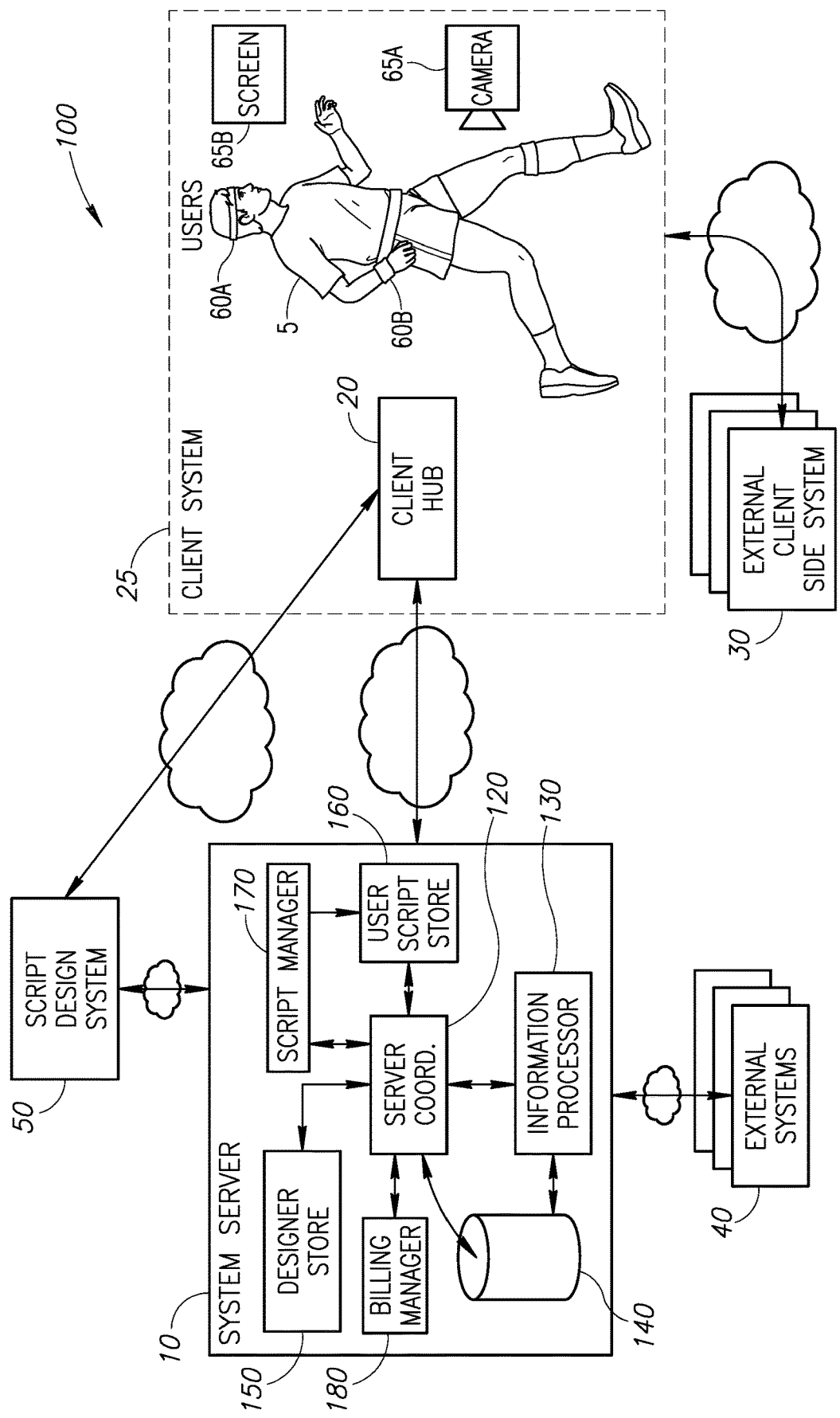
FIG. 1 is a schematic illustration of cognitive state monitoring and alteration system incorporating feedback technologies constructed and operative in accordance with a preferred embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicants have realized that there are a number of limitations with existing systems known in the art as described herein above. For example, existing systems use a fixed (and limited) model of the possible trance types/hypnosis levels, whereas different scenarios and different subjects may require the use of different (and personalized) models, level sets or progressions of levels.

Existing systems also use a limited model (e.g. simple threshold comparison) when analyzing EEG, and are limited in their integration of EEG data with other physiological or physical data (such as Heart Rate Variability (HRV)).

Existing systems handle the in session period only, and do not include an out of session supporting component or integrate information between the two periods.

Furthermore existing systems have no measured information about the effectiveness of the induced suggestions (e.g. actual amount of smoking following an anti-smoking suggestion). It will also be appreciated that relying on subject-provided feedback may be problematic, as the subject may, for example: be biased, be unable to remember the information, be unable to provide objective or precise feedback (e.g. stress levels) or be unable to directly sense the required information (e.g. out of session blood pressure levels).

Furthermore, existing systems do not have the ability to interact with the user during the out of session period (e.g. through out of session suggestion re-activation or re-enforcement).

In general, existing systems are typically adapted to in session stationary use only. In particular, existing systems include a limited set of sensor inputs which are only suitable for in session use. It will be appreciated that the sensors which measure specific physiological parameters during in session stationary use may be vastly different than the sensors which measure the same physiological parameters during out of session period (e.g. when the subject is walking or is generally outdoors).

Existing systems do not support integration of session stages with specific sleep stages, so to make the best use of enhanced susceptibility during some sleep stages, or of deep hypnosis levels which can only be accessed going though specific sleep stages.

For example, U.S. Pat. No. 8,517,912 entitled "Medical Hypnosis Device for Controlling the Administration of a Hypnosis Experience" issued 27 Aug. 2013 teaches a single medical hypnosis device for controlling the administration of a hypnosis session together with processing means for comparing the received physiological feedback data with predetermined physiological data to detect a change in a neurological state of the user.

Applicants have further realized that the above mentioned limitations may be overcome by a system consisting of multiple, dynamically configurable cooperating wearable and non-wearable elements which are also connected to a main server facility. The system includes a variety of instruction/stimuli delivery options, sensors and direct physical effect generation elements (e.g. vibration or temperature change). The system may further connect to external systems to provide additional functionality. The system may also implement a comprehensive framework for use of CSA techniques, which includes integrated interactions spanning both in session and out of session periods.

Furthermore, the system may be guided by scripts which run during the in session and out of session periods, using a sophisticated intelligent script engine. The scripts may run locally (after being downloaded or streamed to the user), or in conjunction with a server as further detailed below.

The system may use a variety of sensors, and an accumulating database of information about the current user (as well as other users), so to accurately assess the user's state at any time. This assessment may provide the scripts and the script creators with information helpful in delivering the relevant instructions correctly and with the right timing. The system may also provide information about the user's state and activities which can be used by the script to find the best way to reach the user's goals—therapeutic, behavior modification or otherwise.

Furthermore, the system may analyze the sleep stages of the user (when used during sleep within both in session and out of session periods), and allow scripts to be synchronized to the sleep stages. This may be useful for sleep-stage based session (in session use), automatic session activation during the user's sleep based on the specific sleep stage (e.g. "teach me language X when I reach a given sleep stage Y") and sleep-stage based suggestion activation (out of session use).

It will be appreciated that the scripts may also communicate with the server to provide data sharing and implement the resulting server-based analysis results while maintaining the user's privacy.

Reference is now made to FIG. 1 which illustrates a cognitive state monitoring and alteration system incorporating feedback technologies 100 in accordance with an embodiment of the present invention. System 100 may comprise system server 10, a client system 25 and a script design system 50. Client system 25 may further comprise a client hub 20 and associated wearable elements 60 and non-wearable elements 65 as described in more detail herein below.

Figure 2:
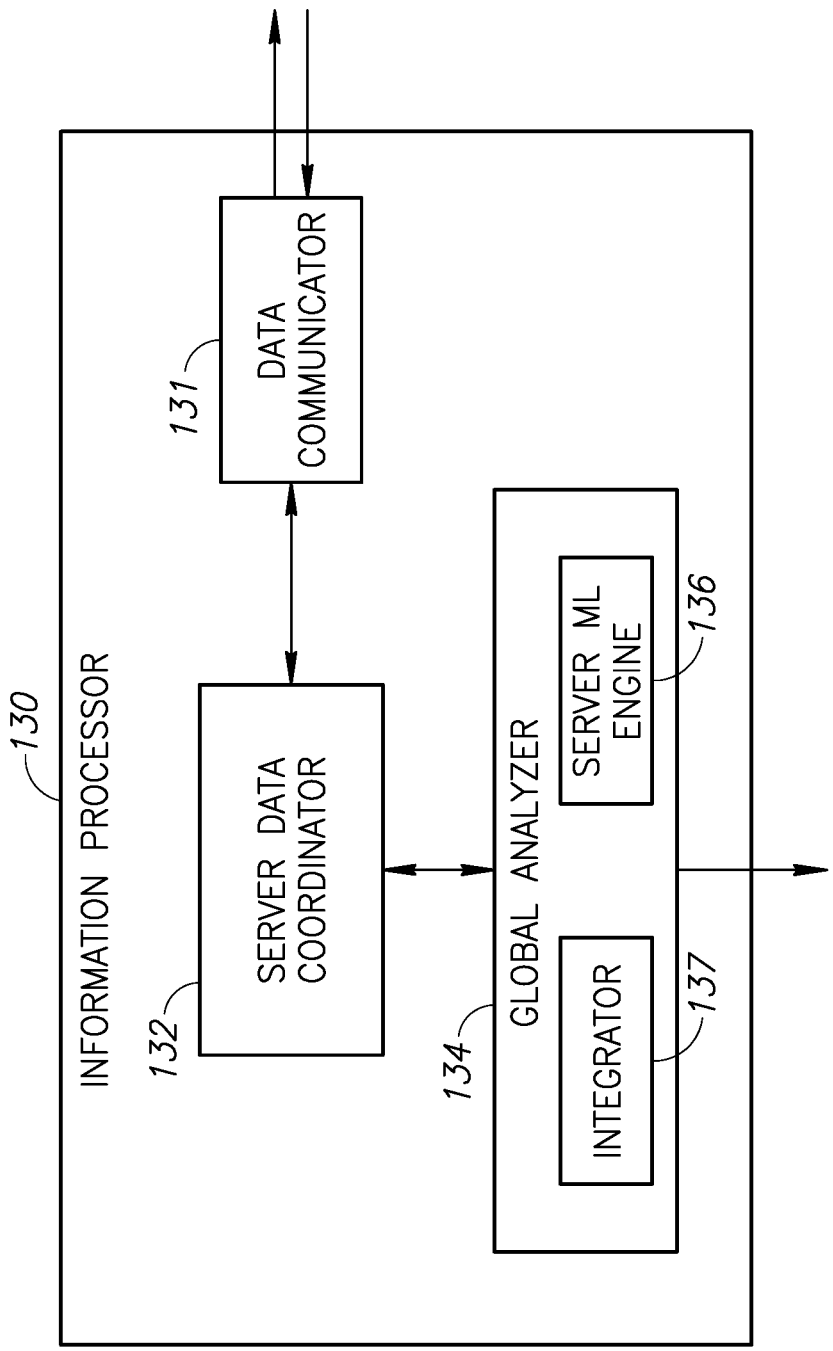
FIG. 2 is a schematic illustration of the elements of the global analyzer of FIG. 1, constructed and operative in accordance with a preferred embodiment of the present invention.

System server 10 may further comprise a server coordinator 120, an information processor 130, a designer store 150, a user script store 160, a script manager 170 and a billing manager 180. Information processor 130 may receive, collate and analyze all data from client system 25 and may further comprise a data communicator 131, a server data coordinator 132, and a global analyzer 134. Global analyzer 134 may further comprise an integrator 137 and a server ML engine 136 as is illustrated in FIG. 2 to which reference is now made. The functioning of these elements is described in more detail herein below.

It will be appreciated that system server 10 may also be connected to a database 140. Database 140 may store user information, scripts and media content together with results of the various wearable and not wearable elements for use by decision maker 2067 and server ML engine 136 as described in more detail herein below. Database 140 may also store metadata attributes to all content types described above.

System server 10 may be a set of one or more central servers which collect information from multiple users, provide scripts and content segments, and allow the update of user database 140 with gathered user responses to scripts and content segments. System server 10 may receive data about user 5 and his state during multiple in session and out of session periods as collected by numerous user client hubs 20, and may analyze and integrate this information to make decisions regarding the current treatment and to provide further information and guidance to the local scripts as discussed in more detail herein below.

Client hub 20 may be any form of composite or virtual client or may be a physical client such as a desktop computer, mobile device, laptop etc. In an alternative embodiment, client hub 20 may also be built into wearable and non-wearable devices as discussed in more detail herein below.

It will be appreciated that system 100 may be implemented in a number of embodiments which differ in the way the workload is divided between server 10 and client system 25 as discussed in more detail herein below. The preferred embodiment may depend on the balance between processing power and communication: the availability of strong processors with low power consumption (i.e. for use within multiple wearable elements 60) on one hand, and the availability of low-latency high-speed wireless communication on the other hand. If strong processors are available, client system 25 may take on additional functions. If low-latency communication is available, server 10 may take on additional functions.

Client hub 20 may communicate with a user 5 who may be connected to one or more wearable 60 and non-wearable elements 65 as described in more detail herein below. Client hub 20 may collate and analyze readings from wearable 60 and non-wearable elements 65 (such as such as UI input means, script responses, neurological and physiological information reading, motion and behavior detection) and any other sensors for use by the pertinent script as described in more detail herein below. It will be appreciated that these wearable 60 and non-wearable elements 65 may communicate with client hub 20 via different local communication and interconnection means such as Wi-Fi, Bluetooth etc. It will also be appreciated that both wearable 60 and non-wearable elements 65 may also communicate directly with server 10 bypassing client hub 20 using built-in communication technology.

In an alternative embodiment to the present invention, client system 25 may also communicate with external client-side systems 30 (such as a smart home system) which may interact with a user 5 in a variety of ways as discussed in more detail herein below. System server 10 may also connect to various external systems 40. Such external systems 40 may include, for example, medical information systems or Internet data sources.

It will be appreciated that server 10 may collate and store data about users and sessions and may analyze this data to modify scripts where necessary and to provide session support where necessary. As discussed herein above client hub 20 may run the scripts during sessions and may receive and analyze feedback from the wearable 60 and non-wearable elements 65 during the sessions.

It will be appreciated that in a typical embodiment, client hub 20 may manage the interaction with user 5 (through wearable 60 and non-wearable elements 65) without communicating with the system server 10 continuously, and may interact with system server 10 mostly at specific time points (such as the start and end of sessions, between specific session phase and at specific points during the out of session period). Thus, user 5 may use client system 25 even if it can't communicate with the system server 10, or if such communication is intermittent.

Figure 3:
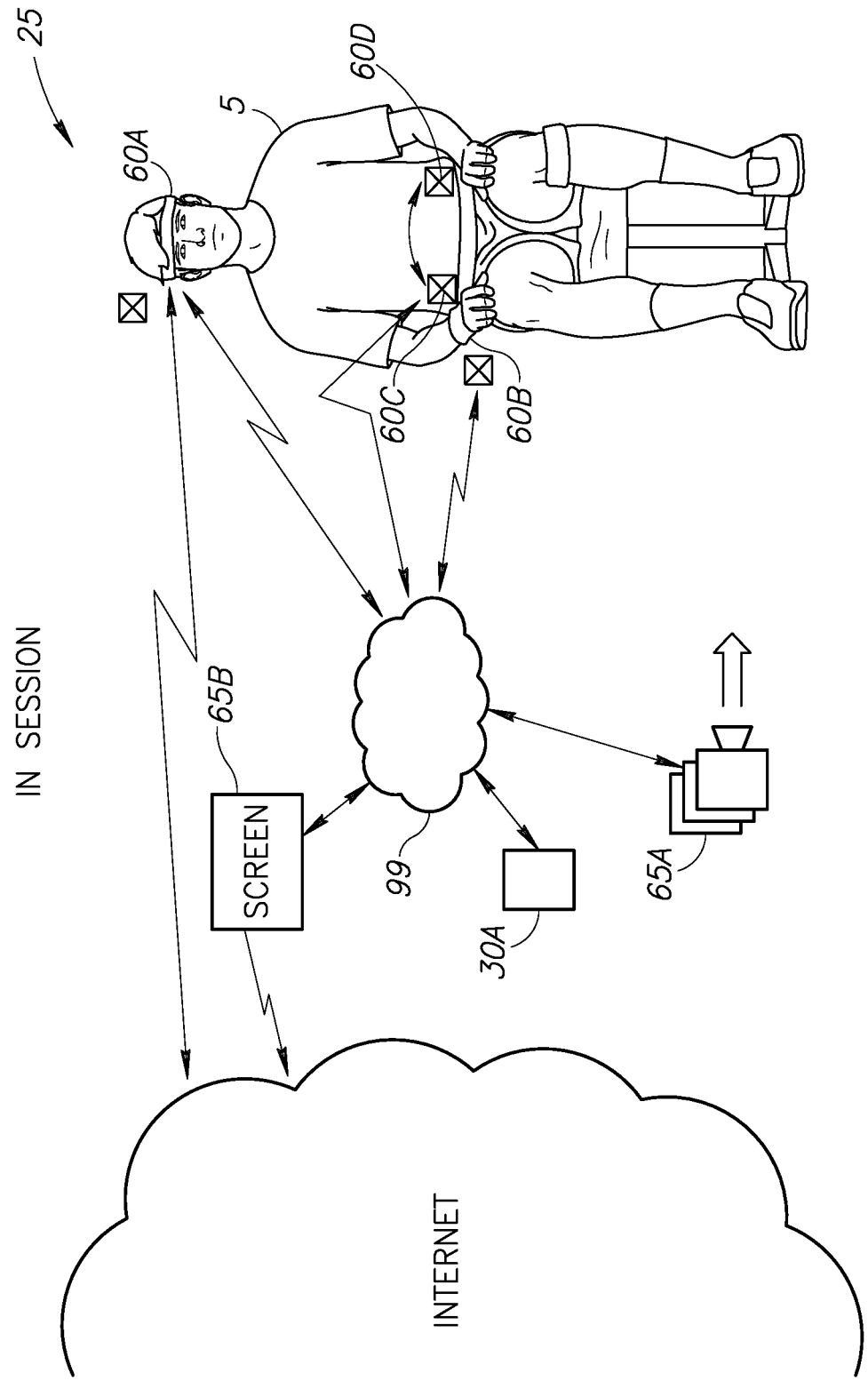
FIG. 3 is a schematic illustration of the use of system of FIG. 1 during an in session phase; constructed and operative in accordance with a preferred embodiment of the present invention.

Reference is now made to FIG. 3 which illustrates an exemplary architecture of client system 25 as used during an in session setting. As discussed herein above, client system 25 may comprise multiple wearable 60 and non-wearable elements 65 connected through a communication medium 99 (which could be based on several wireless communication method such as Bluetooth, Bluetooth Low-Energy (BLE) or others). The communication medium 99 may also include multiple communication methods (such as BLE for communication between wearable 60 and non-wearable elements 65 and the body-area network for communication between the wearable elements 60A (headband), 60B (armband) and 60C/60D (two belt-wearable units). Some of the wearable elements 60 may be connected directly (such as 60C and 60D, both of which connect to the same belt). Some of the wearable elements 60 (such as the headband 60A and one of the non-wearable elements 65B (a screen to present media, system UI and stimulus) may be connected to the Internet to allow interaction with the systems server. One of the external client side systems 30 may also be an environment detector 30A which also detects (and possibly affects) the environment of user 5 (e.g. detecting the heat and humidity in the room, and possibly affecting them by communicating with a smart house infrastructure). Non-wearable element 65A may also perform monitoring (e.g. through a video camera) of user 5 (for example) for motion detection, facial expression reading etc.

Figure 4:
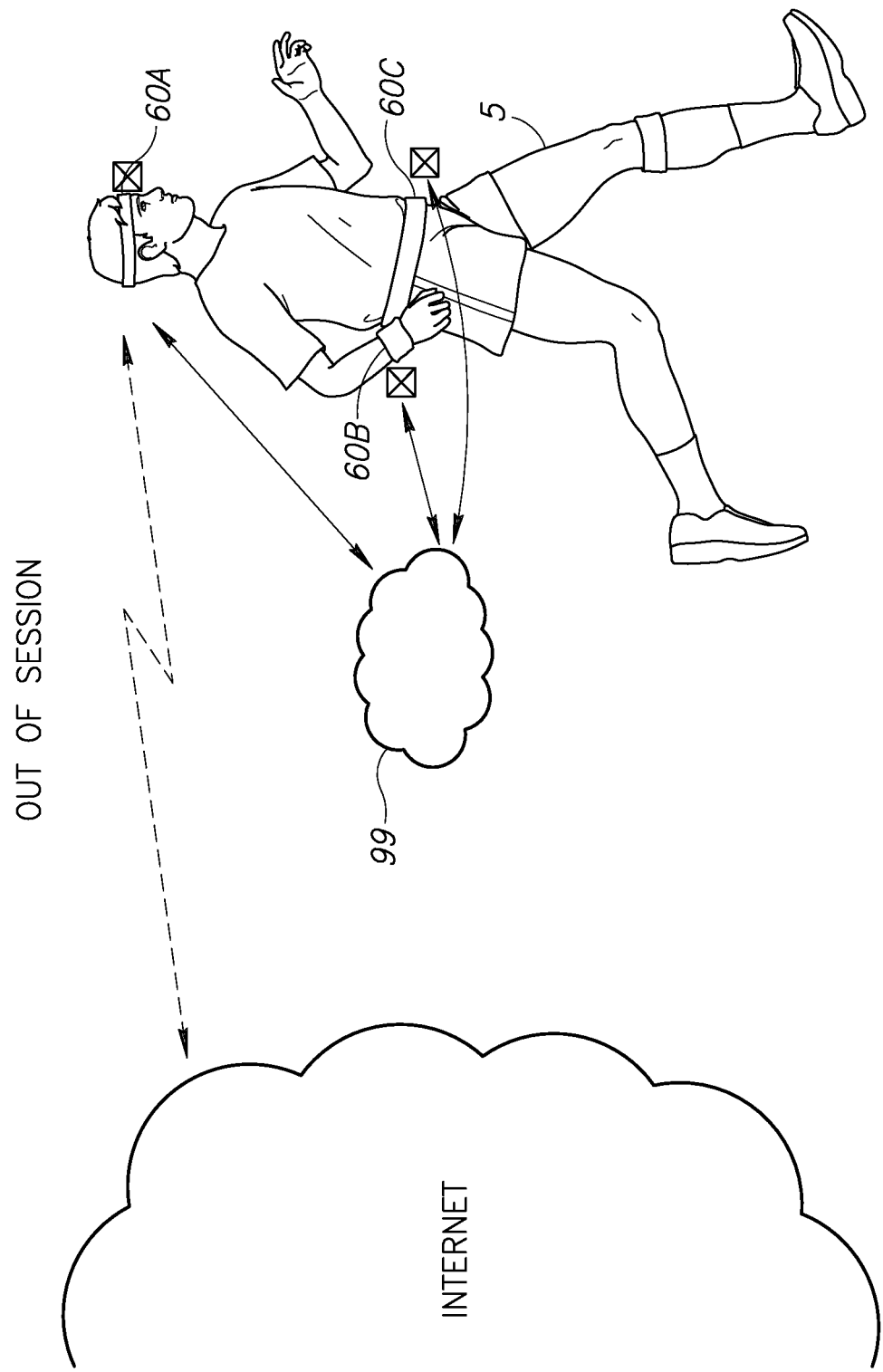
FIG. 4 is a schematic illustration of the use of system of FIG. 1 during an out of session phase; constructed and operative in accordance with a preferred embodiment of the present invention.

Reference is now made to FIG. 4 which illustrates an exemplary architecture of client system 25 as used in an out of session setting. As is illustrated, the client-side only wearable elements 60A (headband), 60B (armband) and 60C (belt-wearable unit)], all of which are connected through communication media 99. Wearable element 60A (headband) may be intermittently connected to the Internet (typically through cellular internet communication) and may serve as a communication gateway for the entire client system 25.

It will be appreciated that the system 100 elements used in an out of session setting are typically a subset of the elements used in the in session setting (with some elements possibly replaced due to reasons such as convenience of use or aesthetics). The reverse scenario (in which additional elements are used in out of session compared to in session) is less likely, though it may occur, e.g. if the out of session activity is a sports activity, and the user uses a number of specialized sports performance measurement wearable elements 60 integrated with the system.

Data communicator 131 may receive data from client system 25 (gathered information from wearable 60 and non-wearable elements 65), possibly including pre-session, mid-session or end-session data), server coordinator 132 may coordinate between the elements accordingly, global analyzer 134 may analyze the received data accordingly including integration of data from different sessions and elements for user 5 as well as other gleaned information from other users. Decision maker 2067 may make decisions regarding therapy accordingly and learning engine 137 may glean useful information from pertinent sessions and data held in database 140 (for user 5 and other users from their sessions).

Figure 5A:
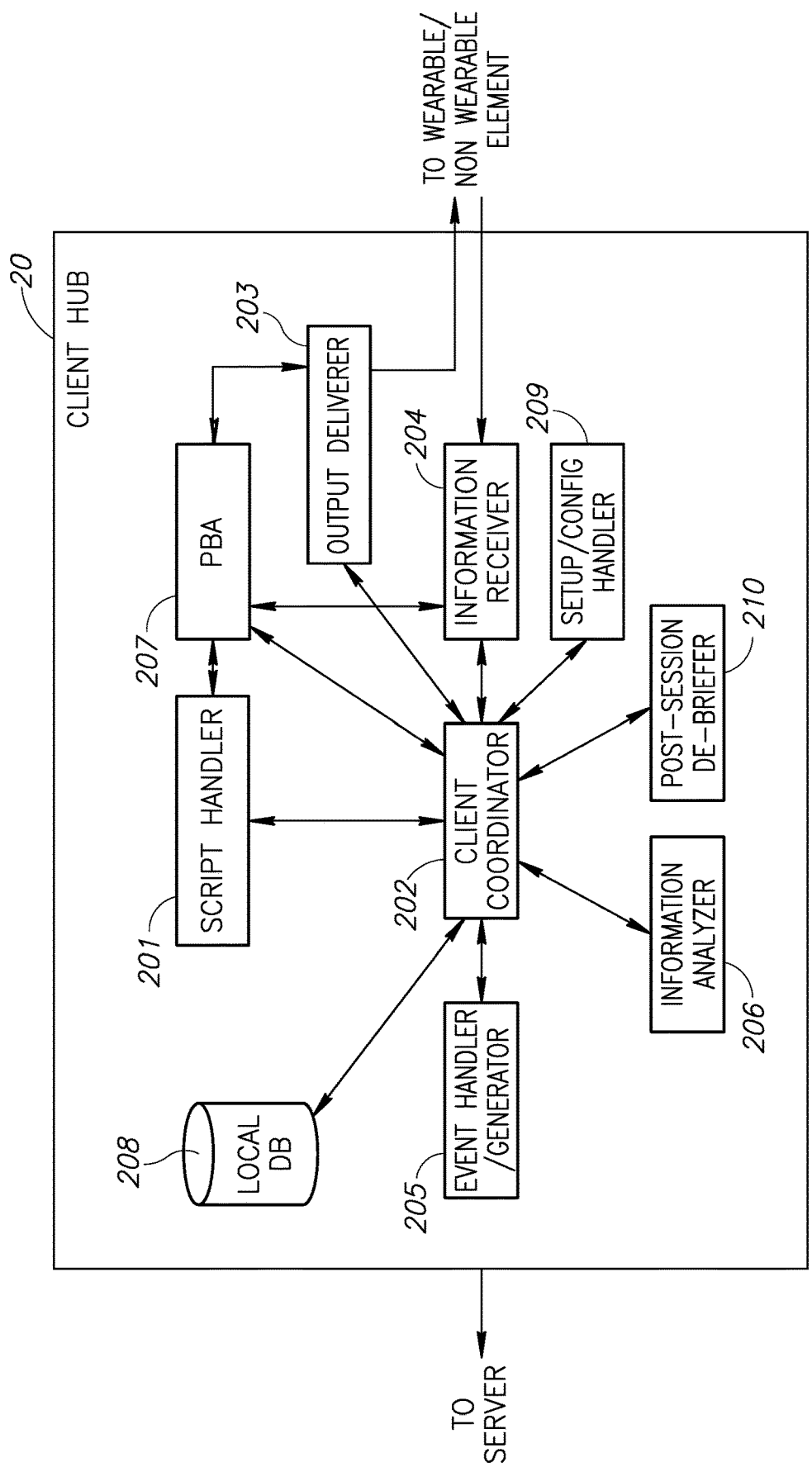
FIG. 5A is a schematic illustration of the elements of the client hub of FIG. 1, of the use of system of FIG. 1, constructed and operative in accordance with a preferred embodiment of the present invention.

Reference is now made to FIG. 5A which illustrates the elements of client hub 20. Client hub 20 may comprise a script handler 201, a client coordinator 202, an output deliverer 203, an information receiver 204, an event handler generator 205, an information analyzer 206, a physiological and behavioral abstractor (PBA) 207, a local database 208, a setup config handler 209 and a post-session de-briefer 210.

Reference is now made to FIGS. 5B, 5C, 5D 5E and 5F which illustrate the elements of script handler 201, output deliverer 203, information analyzer 206, setup config handler 209 and script manager 170 accordingly.

Script handler 201 may further comprise a script runner 2011, a script updater 2012 and a script controller 2013, a client script verifier 2014 and a security/privacy manager 2015.

Information analyzer 206 may further comprise a media handler 2061, a neurological handler 2062, a behavior handler 2063, an environmental calculator 2064, a client ML engine 2066 and a decision maker 2067. Environmental calculator 2064 may further comprise a noise adjuster 2065.

Figure 5E:
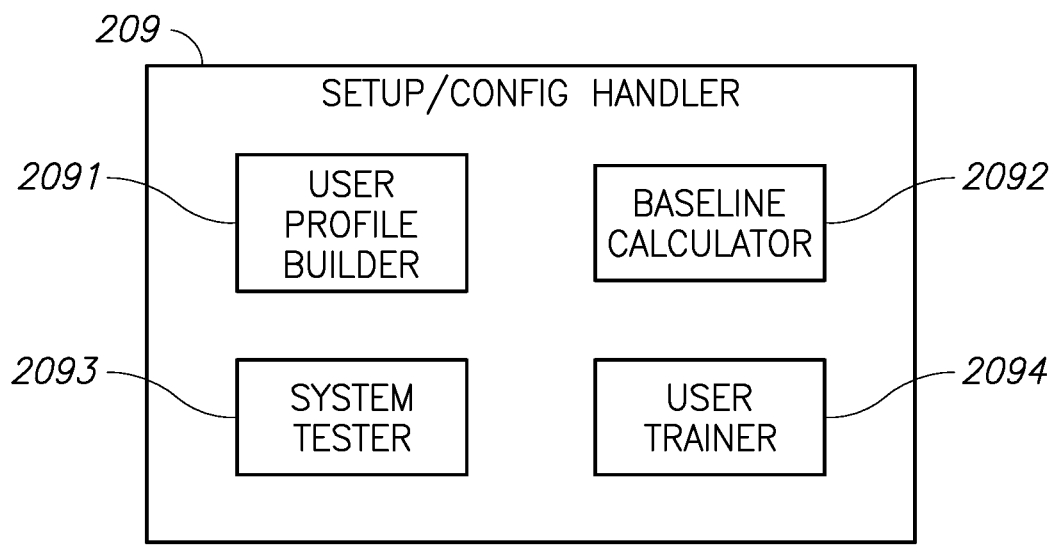
FIG. 5E is a schematic illustration of the elements of the setup/config handler of FIG. 5A, constructed and operative in accordance with a preferred embodiment of the present invention.
Figure 5F:
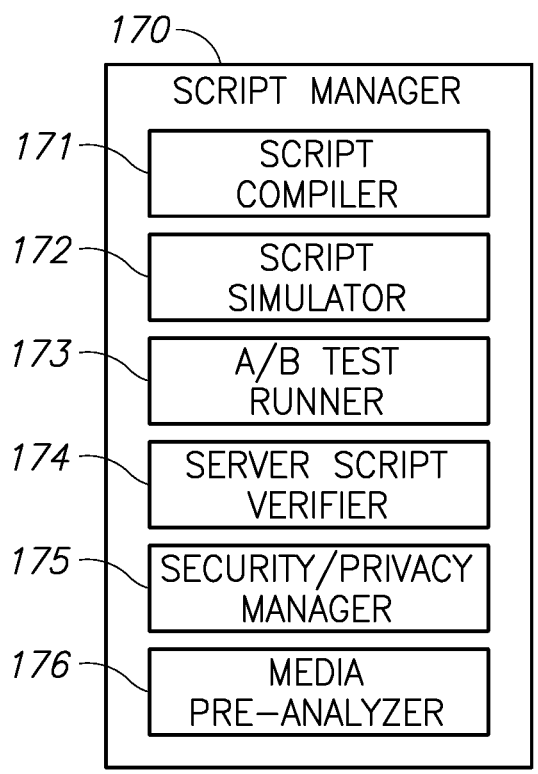
FIG. 5F is a schematic illustration of the elements of the script manager of FIG. 1; constructed and operative in accordance with a preferred embodiment of the present invention.

Reference is now made to FIG. 5F which illustrates the elements of script manager 170 which may further comprise a script compiler 171, a script simulator 172, an A/B test runner 173, a server script verifier 174, a security privacy manager 175 and a media pre-analyzer 176.

Output deliverer 203 may further comprise a sensor activator 2031, a direct physical effect DPE activator 2032 and a media presenter 2033. Setup config handler 209 may further comprise a user profile builder 2091, a baseline calculator 2092, a system tester 2093 and a user trainer 2094. The functioning of these elements is described in more detail herein below.

Script designer system 50 may communicate with system server 10 to upload scripts, related media and script updates. Script designer system 50 may also communicate with client system 25 to provide support services or premium services (such as direct professional human intervention) as described in more detail herein below. Script designer system 50 may further comprise a script designer interface to allow non-technical users such as psychologists to create scripts which handle the complex interaction and analysis. Script designer system 50 may be a standalone client system (as illustrated in FIG. 1), a server based system (in which the script designer system 50 is implemented on the system server 10 and accessed through a browser or other client-side agent software) or a combined client-server system (in which the functionality described above is divided between script designer system 50 and system server 10). An example of the last embodiment may be a script design or editing mobile app installed on mobile devices and cooperating with system server 10 hosted infrastructures.

Designer Store 150 may allow user 5 to purchase system 100 provided scripts. User script store 160 may allow a user to purchase an external script from an external supplier to be used with system 100 in the same manner as the in-house scripts described in more detail herein below.

As discussed throughout, the primary interaction between user 5 and system 100 is guided by scripts which control various aspects of the functionality of system 100 and drive the dialog with user 5. These controlled aspects may include session management, instruction delivery, stimuli (media) delivery, sensor input handling, concept recognition, direct physical effect generation, user input reading, user action detection, user behavior recognition and bidirectional client to server communication (including in particular saving of collected user 5 information, server instructions, script updates and system updates).

During an in session period, this interaction is managed in a structured manner, following a script which may be structured as a transition graph consisting of nodes and edges. Nodes may represent activities of the system, which may include delivery of stimuli and instructions. Edges may have transition probabilities associated with them, which determine the probabilities of transition between the nodes linked by the given edge. Nodes and edges are discussed in more detail herein below.

In one embodiment (server-centric), all script running and information processing is performed by system server 10.

The various elements of client system 25 only provide the direct input and output to the user (and low-level signal processing as described above).

In another embodiment (client-centric), script running and information processing is mostly performed by client hub 20. Client hub 20 may contact server 10 at specific points (e.g. start/end of session) to receive updates to the scripts as well as an update to the script's transition probabilities based on a one-shot analysis of the current user information against the information collected in the system database 140. On-going analysis and transition probability modification is be performed by client-side information analyzer 206. Client hub 20 may synchronize local data 208 with database 140 at certain time points so (for example) to provide backup and persistence as noted above.

In yet another embodiment (client-server), script running and information processing is performed by client hub 20 in conjunction with server 10. During each node execution (as described above), client-side script updater 2012 may contact server-side global analyzer 134, provide it with processed user info (e.g. latest EEG, motion detection and other sensor readings) and receive updated transition probabilities for the running script. Client hub 20 may also contact server 10 for database synchronization as noted above.

If communication is not available, script updater 2012 would still be able to use the transition probabilities provided originally with the script (as updated during the last communication with server 10), and consult information analyzer 206 to provide the best known values.

In all of these embodiments, the processing for out of session periods is be similar, but would be applied to the script segment activated due to association with events managed by the event handler/generator 205.

Thus system 100 may provide the underlying functionality and hardware interfaces (e.g. stimulus delivery, sensor input) and higher-level decoding and analysis of the received inputs, including high-level functions such as behavior recognition and concept reading. The script may only be provided with the processed/analyzed information, and is not given access to the low-level/raw EEG or other data. It will be appreciated that scripts may be based on transition graphs (as discussed in more detail herein below and the information analyzer 206 and PBA 207 may provide the required decision making information accordingly. Furthermore, in typical embodiments, the analysis of information related to other users (for the benefit of the current user) is typically performed by server-side information processor 130—so as not to expose multiple user information through external communication links to client system 25.

As discussed herein above, the interaction of user 5 with the system 100 is conducted during in session and out of session periods. During an in session period, the interaction is managed in a structured manner, following a script which may be structured as a transition graph consisting of nodes and edges. Nodes may represent activities of the system, which may include delivery of stimuli and instructions. Edges may have transition probabilities associated with them, which determine the probabilities of transition between the nodes linked by the given edge.

Client coordinator 202 may also facilitate the downloading of the script and its related media to the client hub 20 and manage storage space and its optimization on the relevant elements. Client coordinator 202 may also interact with user script store 160 (to allow user 5 to acquire new scripts). Existing (installed) scripts may reside on the (client-side) local database 208, or in an area allocated to the specific user on the servers data base 140 (and download on demand when required). Client coordinator 202 may also coordinate data collection to be stored locally on database 208 or server side on database 140. Client coordinator 202 may also handle the use of faulty elements and sensors in conjunction with scripts as described in more detail herein below.

System 100 also provides the communication infrastructure allowing the script to run on multiple interconnected devices together with the communication and data collection channels between user 5 and the script designer.

Other functionalities of system 100 regarding scripts are persistent and may include information retention services which allow scripts to continue running from session to session even with intermittent Internet and inter-component connectivity. This may also include the changing configuration of components from session to session which may be saved within the session history, including full input values from all sensors and inputs, any required internal script information and full timing information. This allows, for example, a script to transfer information from session to session, and from an in session to an out of session period execution, even if some or all of the system components have been replaced (e.g. due to malfunction, an upgrade or because the out of session setting requires a different and disjoint set of client system 25 components).

System 100 may also limit and control script functionality including (for example) stopping scripts which exceed their allocated time. System 100 may stop scripts which cause physical, emotional or psychological distress to user 5 or otherwise exceed their script limitations (as detected through the sensors), or otherwise in the case of an emergency as described in more detail herein below.

System 100 may also deliver the interaction phases not included in the script, such as initial system learning, pre-execution profiling and part of the pre-session evaluation (as described in more detail herein below).

System 100 may handle on-going updates. It will be appreciated that scripts may run for very long period (esp. out of session scripts), and may require updating, including being updated/modified while running via updates from server 10 (push/pull updates). System 100 may support hot swap capability (i.e. changing the script during while the script is running), or alternatively just store an updated version to be used the next time the script would run (in session or out of session). System 100 may also provide software component remote update capability for system software elements as well as script components.

System 100 may also adapt scripts to run with updated version of underlying software platform or hardware elements of system 100. This may be limited and the script developer may be required to update the script to support some of the system updates.

It will be appreciated that the scripts themselves may define session stages and transitions including script-specific or user-specific stage structures, may provide output to user 5 (such as instructions, stimulus, content and direct physical effects) based on rules and inputs, and possibly on synchronization rate sources (as discussed in more detail herein below).

The scripts may also implement high-level functionality and planning, including taking care of session time constraints (and planning time allocation for session stages accordingly).

The scripts may provide high-level user goal management and progress tracking, including providing feedback and displaying the relevant management and motivational UI (e.g. "you're doing great—3 more sessions and you'll overcome your XYZ problem").

It will be appreciated that scripts may implement multiple goals and may transition between goals (including different "progress ladders" in each). For example, a smoking cessation can become a stress relief script (when required), as system 100 does not control the type of treatments that scripts are created for.

The scripts may implement parameters and functions that are specific to one goal, as well as parameters and functions which are related to the entire script functionality (including its multiple goals).

It will be appreciated that system 100 may be offered to a user 5 in the form of a kit. User 5 may decide which type of program he is interested in purchasing such as a program to lose weight, to stop smoking, to increase concentration etc. The kit may comprise of one or more wearable 60 or non-wearable 65 elements together with the appropriate scripts to run the program and the means to monitor effects including detection of behavior where necessary and to administer direct physical effects where necessary. It will be appreciated that the scripts may control various aspects of system 100 during both in session and out of periods. For example, a smoking cessation program may include a script that administers an electric shock or a specific hypnotic trigger activation stimulus when it senses the motion of cigarette being raised to the mouth using an appropriate element.

As discussed herein above, client system 25 may comprise a set of cooperating, wearable elements 60. Wearable elements 60 may include appropriate output devices and sensors used to interact with user 5, i.e. that may deliver instructions and media segments (stimuli) which together form a hypnotic session, may track user feedback (e.g. head nodding, facial expression etc.) as well as physiological, physical and other parameters (using a variety of sensors and sensor data analysis algorithms), and may continue user interaction and tracking outside of the hypnotic session and into "regular life" time period. This later out of session period may include (if needed) periods in which user 5 is awake as well as sleeping periods. The out of session interaction may also include system 100 related activities such as setting up system 100 or providing explicit pre- or post-session feedback as described in more detail herein below.

Wearable elements 60 may typically include but not be limited to: directly wearable items (helmet, head-band, wrist-band, earphones, glasses etc.), hand-held elements, indirectly worn elements (e.g. inside a wallet/backpack/ . . . ), being embedded inside clothing garments or other worn elements (such as cycling helmet); being embedded as a hardware module inside another wearable element 60 or embedded as an added software functionality to another wearable element 60 (e.g. added as application to an existing Smartphone, smart watch, Glasses, etc. using sensors of hosting wearable elements 60). Wearable elements 60 may also include medically-inserted implanted devices or "smart tattoos" as further described below.

It will be appreciated that the interaction between wearable elements 60 and user 5 may also include direct physical effects applied to user 5, such as vibration, pressure, sound effect (e.g. buzzing), temperature sensation change (hot or cold), low-voltage electrical current (as further detailed below) or odor generation. Such a direct physical effect may be applied during an in session period (e.g. to provide additional sensory stimulus or as a feedback mechanism) or out of session (e.g. operating as a cue to activate a posthypnotic suggestion) as discussed in more detail herein below.

It will also be appreciated that a single wearable element 60 device may implement multiple functions. For example, a single integrated headband or glasses may implement some or all of: neurological sensing, audio input and output (including bone conduction interface for audio), speech recording and recognition, virtual reality (VR)/augmented reality (AR) glasses (including analysis and recognition of a viewed scene and use of resulting information by system 100 or the script) and pupil and or iris tracking (e.g. pupil dilation measurement, blinking rate measurement and gaze direction detection). A wearable element 60 may also implement a vibration direct physical effect; a temperature change direct physical effect, inertial sensors to detect head motions (e.g. nodding of the head) as well as general body position (e.g. vertical or horizontal position) and bio-physiological sensing electrodes (for Galvanic Skin Response (GSR), Electromyography (EMG), etc.)

It will be further appreciated that wearable element 60 may also cooperate with other external elements (such as a separate PC, laptop or smart-phone) which provide additional communication services, computing power, storage, display or other capabilities also known as non-wearable elements 65.

Wearable elements 60 may also cooperate with non-wearable elements 65 which provide additional capabilities, e.g. an external camera pointed at user 5 which performs motion detection and allow for motion-related interactions (e.g. evaluating the user's response to a "please lift your arm" suggestion). Such an external camera may also provide hints for signal noise reduction to system 100, by notifying system 100 of the motion of user 5 allowing system 100 to filter out any muscle movement related artifacts and signal noise.

It will be appreciated that system 100 may require different wearable elements 60, wearable elements 60 models or wearable elements 60 configurations during different usage periods (e.g. during in session, regular awake period, sport activity or sleeping). For example, a headband which can be using during an in session and later an out of session sports activity may not be convenient enough for use during sleep, and would be replaced with a specific armband (designed so to be convenient enough for use while sleeping). User 5 may even desire to switch between different wearable elements 60 due to personal consideration, e.g. different wearable elements 60 which suit the appearance of user 5 in different social settings.

It will be appreciated that some wearable elements 60 may work best when precisely adapted to the specific user's body structure. A notable example is an earphone wearable element 60 which works best when adapted to the specific user's ear or ear canal structure. Such adaptation may improve (for example) the convenience of wearing, the ease of insertion and removal and the acoustic quality of the earphone.

In an embodiment of the present invention, an earphone wearable element 60 may include additional functions, such as sensor functions (e.g. EEG, blood pressure, heart rate, accelerometer/gyro etc.) or direct physical effect generation functions. Such functions may also benefit from better, closer or more precise placement of the functional element (e.g. the sensors' active element or electrodes) against the body of user 5 providing better connection with the body.

It will be appreciated that all of the above applies to additional wearable element 60 categories, and also to earphone wearable element 60 sets (e.g. two earphones which should both be individualized).

Thus, the system 100 vendor may offer the option to purchase an individualized version of a given wearable element 60. Such an individualized version may include the entire wearable element 60, or just a sub-element of wearable element 60 (e.g. a framework, connector or carrier sub-element), with the main element being common to all versions of wearable element 60. The personalized element may in fact be the actual electrode(s) touching the user's skin, which may provide a better measurement profile.

The system 100 vendor may offer a completely individualized wearable element 60 or a selection from a series of possible predefined designs. The system 100 vendor may determine the individualized wearable element 60 based on some form of scanning of the related body member on/in which the individualized wearable element 60 is to be worn or used. Such scanning may include photography (including multi-angle photography) or 3D scanning or physical measurement. The scanning may be performed by the user himself (sending the results to the system's vendor), or in a predefined scanning and fitting location.

The system 100 vendor may provide the individualized wearable elements 60. In addition, third party vendors may provide additional wearable elements 60, including both hardware and software support for that hardware (such as drivers and interfaces). The system 100 vendor or third party vendors may also create detailed designs and send them to the user, to be created using 3D printing or similar technology.

The same individualization technology may be used to personalize wearable elements 60 in other ways, such as color, shape, design, size, material etc. Such personalization may also support the functionality or quality of the wearable elements 60, but may also have other purposes, such as resolving issues related to allergies to specific materials, making the wearable elements 60 design and color a better fit to other elements worn by the user etc.

Wearable elements 60 and non-wearable elements 65 may be implemented using a specialized hardware platform (as discussed in more detail herein below) which includes some of the required sensing, processing, storage and communication capabilities.

They may also be implemented using a hardware add-in to existing commercially available devices which include hardware add-in capability, such as the modular phones designed by Google's project ARA (found at www.projectara.com). Such a hardware add-in may typically include associated software as well.

Wearable elements 60 and non-wearable elements 65 may also be implemented using software implemented on existing commercially available wearable, luggable or off-body computing devices (e.g. a programmable sport watch, smart phones, laptop, PC, web camera etc.). Such software may exploit (and be adapted) to the specific sensors included in the pertinent element, such as the inertial sensors included in smart phones or the heart rate sensors included in some sport watches.

Another method of implementation is by using medical implants providing specific functions to the user's body. The implants may interface with system 100 through wireless communication, physical (wired) connection or some form of body conductivity.

It will be appreciated that different elements may implemented in any of the different ways as discussed herein above (specialized hardware, hardware add-on, software etc.), so that a specialized head-band (for example) may be used together with a software-extended sport watch.

Some of the elements may require other elements to operate, e.g. a miniaturized sensor element might include limited functionality and depend on the use of a specific armband to provide the additional processing and storage required for it to operate.

Different wearable element 60 configurations include different sensors, e.g. to help the user resolve different issues. For example, client system 25 may include a wearable element 60 configured with different versions of a gas detection sensor, aimed at detecting smoke (for users tackling a smoking problem) or alcohol (for users tackling a drinking problem).

The elements may be connected in a variety of ways including via a physical connection, e.g. a headband component may be physically connected (via wires) to an additional electrode component which provides additional EEG reading information.

They may also be connected via a wireless connection, using any combination of protocols such as Wi-Fi, Bluetooth, and Bluetooth Low Energy (BLE).

Another form of connection may be communication based on body conductivity, i.e. using the body of user 5 as a communication medium.

Such connectivity may occur directly between elements (e.g. peer-to-peer or mesh topology), or though some of the elements acting as communication hubs (e.g. star topology). More specifically, client system 25 elements may serve as low energy inter-sensor communication for different wearable 60 and non-wearable elements 65. This can be achieved, for example, using communication based on the ZigBee wireless specification (as published by the ZigBee alliance at www.zigbee.org), or using wireless sensors implementing the ANT+ protocol (as described in https://en.wikipedia.org/wiki/ANT%2B). The choice of protocol and topology may also be affected by power management considerations, e.g. which of the elements has sufficient power to act as communication and processing hub.

It will also be appreciated that system 100 may be used in conjunction with external client side systems 30 which provide additional data, sensing capabilities and other services but are not a part of the regular system 100. These may be wearable or non-wearable systems.

It will be appreciated that external client side systems 30 may also be integrated into system 100, with the client system 25 elements (wearable elements 60 and non-wearable elements 65) serving as a hardware platform and with the third party solution devices extending the platform. For example, a third party may provide a specialized pressure device (applying different degrees of pressure to a skin region) which is attached or connected to system 100. Client system 25 may provide a standard API which allows such a device to be used by scripts running on it.

Figure 6:
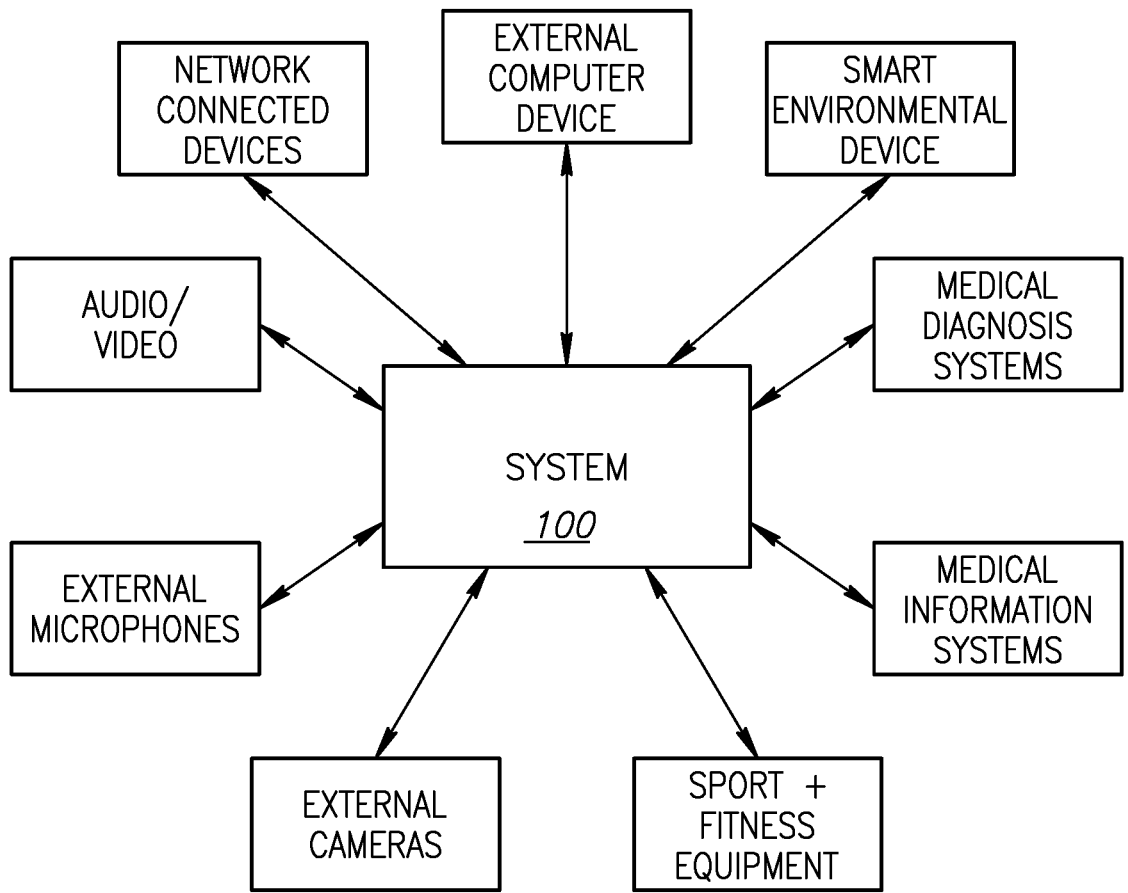
FIG. 6 is a schematic illustration of the use of system of FIG. 1 with external systems, constructed and operative in accordance with a preferred embodiment of the present invention.

In particular, system 100 may interface with any of the following external systems 40 and external client-side system 30 and support any of the following applications for their use as described below and illustrated in FIG. 6 to which reference is now made.

| External system 30/40 types | Used for |
| --- | --- |
| Medical diagnosis systems | Additional user measurements. Baseline user physiological data (e.g. baseline EEG/EKG information). User's genetic information - to add to user's profile information. |
| Medical information systems | User's profile information. |

-continued

| External system 30/40 types | Used for |
|---|---|
| | User's medical history/profile; Historical physiological measurements. |
| Sport and fitness equipment (e.g. sport watch) | Sensor platform, e.g. heart rate, motion detection. Current sport activity tracking, e.g. what is the current sport activity being undertaken, what are the current activity parameters (e.g. activity start time, meters run, total climb/descent etc.). |
| External camera, e.g.: Smartphone cameras. Security cameras. Desktop video conferencing/chat camera. Cameras embedded in game consoles. Cameras embedded in smart TV's. | Gesture detection for system interaction. Motion detection. Behavior recognition. Body language reading. Face recognition. Facial expression reading. Eye motion detection - including gaze direction, focus, blinking, pupil dilation etc. |
| External microphone (in Smartphone etc. as above). | Voice recognition. Voice feedback. Voice command/response. Voice analysis. Physiological sensing - breathing rate, heart rate. |
| External audio/video display systems, e.g.: External speakers. External earphone/headset systems. Phone systems. Home audio systems. TV sets. Car sound systems. Car navigation systems. Car HUD displays. | Script output (instructions, stimuli/content segments). System UI presentation - including visual & voice prompts. |
| External network-connected devices (e.g. PC, Laptop, tablet, mobile). | Internet connectivity gateway. Added processing support. Touch-based input. Shared experience hub - allowing multiple users to use cooperating scripts. This could be in a single or multiple locations. |
| External computing devices (as above). | Internet connectivity gateway. Added processing support. Storage services - for collected information which can't be uploaded to servers (e.g. due to intermittent Internet connection). |
| Smart environmental elements (e.g. smart home, Internet of Things devices) | Detecting environmental interactions e.g. interface with a smart refrigerator (so to detect when the user is opening the refrigerator) for a dieting script. Maintaining continuous area monitoring, e.g. using a smart home internal network so to monitor users' smoking habits via multiple cameras and smoke detectors in the house. |

It will be appreciated that the connection between client system 25 and external client side system 30 may typically be wireless, through in some cases it could be direct or internet-based connections (e.g. using a web service). The connection with external systems 40 may typically be direct or internet connected.

Such connections may use standard protocols supported by external systems, such as the specialized Bluetooth profiles used for health-care (e.g. BLP Blood Pressure Profile) or sport and fitness (e.g. CPP Cycling Power Profile)

.

Such communications may be real-time (i.e. the external system is integrated into the process performed during one of the operating modes), or may be non-real-time (such as data exchange with an external system which provides additional data about the user but is not involved in the actual processing sequence).

The communication is usually performed at the client side (e.g. for the specific use) but may also be performed on the server side (with system server 10 acting as an intermediary to the external system 40).

It will be appreciated that some of the functions mentioned in the table above are low level functions, and some are higher level function built on top of the lower-level functions. For example, behavior recognition is a high-level function which relies on the lower-level motion detection.

In some of the cases above (e.g. the smart home scenarios), system 100 may need to receive preliminary authorization keys, receive information from the external systems 30 or 40 (regarding the availability of cameras, sensors and other relevant devices), build an internal description/map of the relevant devices and connect to these devices when required (so to protect the privacy of other people which visit the same spaces as user 5).

As discussed herein above system 100 may be used with different element configurations at different times (in session and out of session) and with different operating modes, e.g. using different sets of elements during a hypnotherapy session, during sleep, during a sports activity and during everyday life.

Thus system 100 may continue to operate and use and update the same underlying database 140, even when user 5 (for example) removes the elements adapted to one mode of operation (wearable elements 60 or non-wearable elements 65) and uses a different set of elements adapted to the new mode of operation.

It will be appreciated that some embodiments of the present invention may require a specific master element to be used in these multiple operation modes so to implement such operational persistence. Other embodiments may support a mode of use in which there are no common elements between the different sets of elements. For example, the set of elements used during a session may be completely disjoint from the set of elements used during sports activity. However, system 100 may still provide persistence and continuity of operation between the different modes of use.

It will be appreciated that in order to achieve this, different system 100 elements may include synchronization and "hand over" functionality implemented via the communication methods connecting the elements, so that an element set used in a given operating mode may continue from the point in which a previous element set has finished (i.e. the "old" elements hand over control and synchronize with the "new" elements via the element-to-element communication).

This should not require synchronization via system server 10, as the communication with system server 10 may be intermittent (as discussed herein above) and may not be available when the switch-over is performed. However, the system 100 may also offer server-based synchronization when server connectivity is available during the switch-over process.

Furthermore, client system 25 should assume the Internet connectivity is always intermittent, in particular in out of session mode. Thus, system 100 may provide the required caching and other mechanism so to function off-line and only use Internet connectivity when available.

As discussed herein above, client system 25 may implement multiple types of system to user interfaces i.e. channels through which system 100 interfaces with user 5 (e.g. for information/stimuli presentation or direct physical effect generation) and user 5 interfaces with client system 25 (e.g. for user 5 input, user information gathering or user sensing).

Such interfaces may be two-way (forming complete interactions or feedback loops) or one-way. They may include explicit interfaces (e.g. audio stimulus played through earphones, a vibration applied to the user or skin temperature reading through an attached sensor) as well non-explicit ones (e.g. subliminal message embedded inside a video segment stimulus).

The interfaces may be implemented by one or more wearable elements 60 (e.g. headband sensors) or non-wearable elements 65 (e.g. an external computer displaying a system UI or an external video camera used for user motion detection). A given interface functionality may be implemented through different elements (with the same or different levels of capability). For example, user motion detection may be performed using a camera setup in a stationary, in-house in session setting. The same functionality (but at different level of capability) may be provided by a motion detecting bracelet worn by user 5 during a sport activity out of session period.

It will be appreciated that interfaces may integrate multiple technologies, possibly implemented using multiple elements. Further to the example above, analyzer 206 may perform user motion detection by combining information from an external camera with that provided by a motion detecting bracelet. As another example, system 100 may deliver audio stimuli through a combination of external speakers (which provide ambient background music) together with specific instructions and stimuli provided by dedicated earphones.

As discussed herein above, different operating modes (in session, out of session/sleeping, out of session/sport, out of session/social etc.), and the specific combination of system elements (wearable elements 60 and non-wearable elements 65) used in each mode may dictate specific interfaces and interface technologies.

Figure 7:
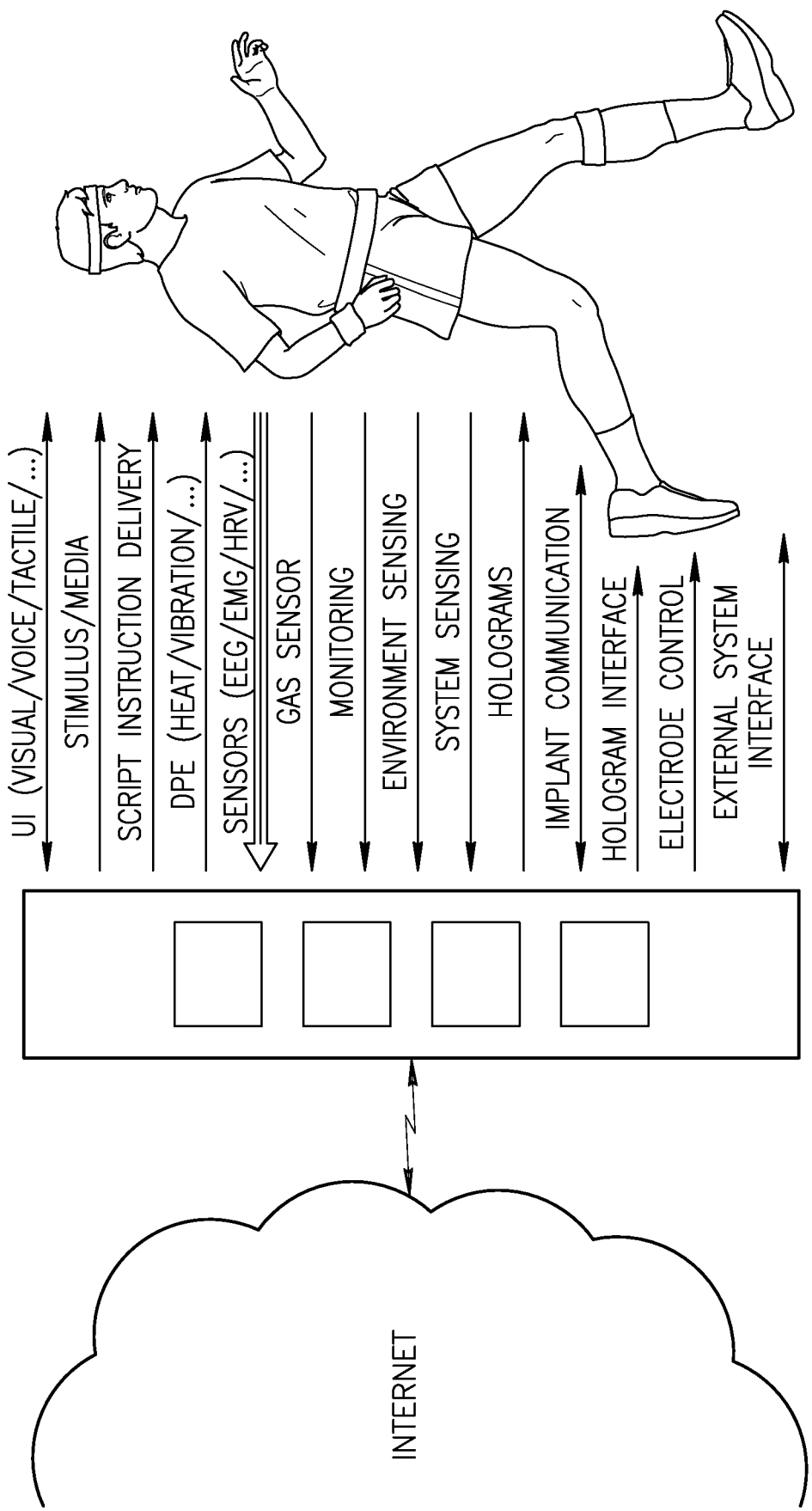
FIG. 7 is a schematic illustration of the different modes of interaction of the wearable and non-wearable elements of FIG. 1 with a user; constructed and operative in accordance with a preferred embodiment of the present invention.

Reference is now made to FIG. 7 which illustrates some of the ways in which the client system 25 (consisting of client hub 20, wearable elements 60 and non-wearable elements 65) interact with user 5. As can be seen, client system 25 may both receive input from wearable elements 60 and non-wearable elements 65 and may also provide output such as direct physical effect generation. The different ways are also listed in the following table which expands on the direction of information flow.

| Interface type | Direction | From/to |
|---|---|---|
| UI | I/O | User: visual (incl. VR/AR, motion based), voice (2-way - speaker/earphones + microphone), tactile, . . . |
| Stimulus/media | Output | User: visual (incl. VR/AR), voice, . . . |
| Script instruction delivery | Output | User: through media (visual, voice, . . . ) |
| DPE | Output | User-worn direct physical effect applier: heating/cooling element, vibration generator |
| Sensor | Input | User-worn sensors: EEG, EMG, HRV . . . |
| Gas sensor | Input | User worn gas sensor |
| Monitoring | Input | Camera (focusing on user or environment), motion detection (user worn/user monitoring), . . . |
| Environment sensing | Input | Environmental sensors: background noise, humidity, vibrations |
| System sensing | Input | System sensors: GPS, acceleration |
| Holograms | Output | User |
| Implant | I/O | User implants - including both control of |

-continued

| Interface type | Direction | From/to |
|---|---|---|
| communication | | implants and reading of information gathered by implants |
| Holograms interface | Output | User |
| Electrode control | Output | User-worn controllable electrodes |
| External system interfaces | I/O | |

It will be appreciated that client system 25 may typically include a suitable interface (UI) to interact with user 5. Such interaction may be administrative (signup, registration, setup etc.) or operational (related to the in session/out of session interaction).

It will be further appreciated that this UI may be separate from the actual session delivery interaction, which is typically administered via instructions and (media) stimuli output, and uses various input means as detailed below. In particular, when in a trance state, user 5 is typically not capable of dealing with a regular user interface (which typically requires delicate manipulation of a mouse, a touch screen or similar UI devices).

Thus system 100 may employ different interaction modes for different needs and stages, including (for example) a combination of any of the following:

Regular visual UI display for system elements or using external connected components (e.g. a connected Smartphone or Smart-TV screen) as further detailed below regarding visual output delivery.

Regular UI inputs (keyboard, mouse, touch-screen etc.)

Physical buttons, dials or other physical controls installed on some of the elements or connected external systems (e.g. a TV remote control used to operate a connected Smart-TV).

Voice UI which may include both voice output and voice input (based on voice command recognition or natural language processing). Such voice command input may be performed by microphones (including regular microphones as well as those based on bone conduction) built into specific wearable elements 60 or non-wearable elements 65, or the microphones integrated into external client side systems 30 (e.g. Smartphone or Smart TV's) which interface with client system 25. The voice UI input (i.e. the user's speech received by system 100) may also be used for voice analysis as described in more detail herein below.

Other interaction modes may be motion/gesture/facial expression based, using the detection capabilities of system 100 (as described in more detail herein below). These may include in particular head-based gestures (e.g. nodding, shaking or even bobble) which may be used by user 5 in response to system prompts.

A hologram-based UI including such technologies as virtual keyboard/touch-screen or other UI, avatar based UI etc. may also be used. Such a hologram-based UI may be highly customizable to the specific preferences of user 5, including those gathered from any in session information recording and other calibration information. It will be appreciated that holograms may also be used for stimulus output.

As discussed herein above, system 100 may use different methods during different user phases. It will be appreciated that the main administration of the CSA session is done through instructions and stimuli delivered to user 5 (together with the relevant stimulus and direct physical effect administration as discussed in more detail herein below). The instructions and stimulus are typically delivered using visual or audio or delivery means (discussed in more detail herein below).

It will be appreciated that the delivery of the instructions and stimuli may be controlled by the relevant script acting upon information gathered from user 5 (e.g. via analyzed voice response, motion detection, neurological state detection, other physiological and physical sensors, fEMG (facial electromyography) etc.) as well as additional system information as discussed in more detail herein below.

Instructions may include general instructions which do not require specific execution (e.g. "feel relaxed and well rested"), direct execution instructions which direct the user to perform an action which can be directly measured or tracked (e.g. "lift your right arm" instruction, tracked via a motion detection capability) and direct execution instructions which direct the user to perform an action which cannot be directly measured (e.g. "think about a beautiful outdoor landscape you've seen recently"). For some of these instructions types their execution may be indirectly measured (e.g. "feel relaxed and empty your mind" may be correlated with specific neurological state or physiological or physical measurement values).

Other types of instructions may be instructions which require a specific response (e.g. verbal or selection via gesture/gaze) that can be recorded, analyzed and possibly used in a later interaction (e.g. "What is your favorite color?").

The instructions may also be related to the environment of user 5 rather than the user himself (e.g. "please dim the lights in the room and close any source of background noise such as TV or Radio"). Such instructions may have measurable results (e.g. by light/noise detection in the given example) or not.

System 100 may implement multiple user state sensors in order to receive readings and to administer stimuli. Some of these sensors detect physiological parameters of user 5 (i.e. biophysical parameters of the body functioning not directly under the user control) and some detect physical parameters (i.e. physical parameters of the body movement typically controlled by user 5).

It will be appreciated that some measured (typically physical) body phenomena may include both user-controlled and non-user-controlled elements. For example, hand movement may include both a conscious hand gesture as well as a nervous twitch which user 5 cannot control.

Physiological sensors may include Galvanic Skin Response (GSR), Blood Volume Pulse (BVP), Electrocardiography (ECG) or Photoplethysmogram (PPG), which may record heart rate information. Physiological sensors may also include Electromyography (EMG), which may monitor electrical activity of the muscles and can provide additional information regarding specific muscle activity (e.g. for monitoring certain gestures).

Another body phenomenon is breathing rate which may be measured using a chest belt to detect chest motion, through motion detection sensing of chest motion, using Pulse Oximeter data extracted from a Photoplethysmogram (PPG) signal and using a GSR sensor.

Other measurable phenomena are blood/oxygen level, blood pressure, body/skin temperature and various hormone levels. For example Cortisol (which is indicative of stress) can be measure in real time (e.g. measuring in the user's saliva, or in interstitial fluid (ISF) using specialized sensors, as described in the publication "A Realtime and Continuous Assessment of Cortisol in ISF Using Electrochemical Impedance Spectroscopy" by Venugopal M, Arya S K, Chornokur G, Bhansali S. Sens Actuators A Phys. 2011 Dec. 1; 172(1):154-160. http://www.ncbi.nlm.nih.gov/pubmed/22163154. It may also be measurable using other skin/body embedded sensors, as well as through NIRS sensors.

Also measurable are muscle tension, detecting tension in different muscle groups such as face, arms and others and additional physiological parameters, such as these which may be measured through blood testing (e.g. done in real-time using an implant as noted below), breath analysis or any other technique.

Physical sensors may include any of the following (although some of these sensors may have a physiological component):

Motion detection, the user's motion may be continuously tracked using video when available (e.g. from an external camera), directly from on-body motion sensors installed as part of the various wearable elements 60 or by using an integration of the two.

User posture detection, sensing if the user lying down, sitting etc.

Body gestures, including hands, arms, feet, shoulders etc. These may include head-based feedback such as nodding, shaking or even a bobble. For example, a script may include a segment asking a yes/no question, to which user 5 may respond with a head-based feedback. It will be appreciated that some of these feedbacks may require localization (as accepted body signals vary from one culture to another).

Fine-grain motion detection, detecting minute motions such as fidgeting, twitching, shaking, tics etc. This may also include Restless Legs Syndrome (RLS) detection.

Facial gestures or expression (e.g. as analyzed by fEMG) which could provide an implicit feedback. This may include, for example, the user laughing (providing a feedback on the currently playing audio segment), rapid blinking, sadness expression etc.

Eye motion tracking (through video or EEG), which may include tracking of open or closed eyes, eye blinking, direction of gaze, pupil dilation.

As discussed herein above, the use of multiple sensors provides system 100 with opportunities to integrate the input from these multiple sensors and improve the measurement of specific physiological or physical parameters. Furthermore, analyzer 206 may use physiological sensor data to verify EEG data.

For example, analyzer 206 may analyze signal information (such as EEG artifacts (known as EOG), fEMG, motion etc.) using Blind Source Separation (BSS) and pattern recognition algorithms, and detect some of the types of motion described above (e.g. blinking and eye opening/closing, sad face, smile etc.). Thus, analyzer 206 may correlate such analyzed EEG information with other wearable 60 and non-wearable elements 65. The resulting information is highly useful for script event generation, sleep stage detection, face expression analysis etc.

Client system 25 may also use some physiological sensors as UI means, e.g. using hand/face gestures to interact with system 100 or with specific scripts as discussed in more detail herein below.

Furthermore the system 100 may include a gas detection sensor, aimed at detecting gasses in the vicinity of user 5, inhaled into or exhaled (or otherwise emitted) from the body of user 5. Such a sensor may be used, for example, to detect smoke (for users tackling a smoking problem) or alcohol (for users tackling a drinking problem).

This could be a single universal gas detection sensor, or a set of sensors adapted to specific gasses.

Such a sensor may be placed so to detect (specific) gases in the general environment of user 5, or may be placed (and configured) to focus on a breath analysis of user 5 (i.e. by placing the sensor on the front side of a headband worn by user 5). System 100 may also use multiple gas sensors (placed in different positions) so to differentiate between results of the breath analysis of user 5 and gas presence in the general environment of user 5. For example, environmental calculator 2064 (as discussed in more detail herein below) may correlate the results of two gas sensors, one placed on the front side of a headband and one placed on an armband.

In particular, such a gas sensor may detect incidences of passive smoking, and provide an indication which may be relevant to some scripts (e.g. warning the user of a smoking cessation script that he would better leave the area since the second-hand smoke in the area may be detrimental to the user's smoking cessation effort).

It will be appreciated that client coordinator 202 may receive and record the information on local database 208 from some or all of the available sensors so to create a database of baseline sensors values for the specific user, and may correlate this information with additional user and environmental information as further detailed below. Client coordinator 202 may also send the information to server system 10 to be saved on database 140 for use by global analyzer 134 for central storage, analysis against other general user information, backup and to support client system 25 persistence.

As discussed herein above, an EEG reading (as well as other system sensors) requires the use of electrodes to detect electrical (or other) user 5 body activities. System 100 may use standalone electrodes or electrodes integrated with other wearable elements 60. Furthermore, system 100 may use the enclosures or other elements of various wearable elements 60 (e.g. a metal enclosure of wristwatch) as electrodes as well. In particular, electrode functionality may be integrated into direct physical effect wearable elements 60 which are in contact or are in close proximity to the body of user 5.

It will be appreciated that system 100 may use personalized wearable elements 60 (matched to the specific body parameters of user 5) so to provide the best conductivity for the electrodes. This may also include personalized electrodes manufactured especially to match the specific body parameters of user 5.

System 100 may also use many types and categories of electrodes. In particular, improved results may be achieved by the use of active (rather than passive) electrodes. Such active electrodes include an initial amplifier on the electrodes themselves, rather than an external cable-connected unit. This prevents noise creation due to cables or electrode movement.

System 100 may also use dry rather than wet electrodes. In this embodiment, user 5 may be required to apply a conducting gel (or other preparation process) to the measured skin area before placing the relevant wearable element 60 and electrodes.

Such a preparation process is reasonable for limited-time use in medical setting. However, it is less suitable for a typical use in which the user may be expected to be connected to wearable element 60 devices for long period of time, in particular during out of session periods.

To improve the conductivity of dry electrodes, the pertinent wearable element 60 may also include a mechanism to generate localized humidity at the electrode contact point. One such mechanism (co-located or attached to the electrodes) may spray a small amount of conductive liquid (or other material such as conductive dust). Another such mechanism may be a heat-generating mechanism which would heat the skin of user 5 to some extent, causing him or perspire, with the generated perspiration acting as a conductive liquid. Such a mechanism may also function as a direct physical effect administrator (in parallel to the described functionality).

Such a heat-generating mechanism may be located next to the electrode (and the skin of user 5). It could also be located further from the skin of user 5, using the heat conducting properties of the electrode itself to conduct the heat to skin of user 5. Either way, it is important to limit the generated heat so to be below the sensory threshold of user 5.

Such a heat-generating mechanism may also serve as a heat (and possibly cold) generating direct physical effect administrator (as discussed in more detail herein below).

Any such mechanism (liquid spraying, heat generating or otherwise) may operate continuously (e.g. whenever the electrodes are required to operate). Output deliverer 203 may also activate any such mechanism conditionally, based on an analysis by analyzer 206 of the quality of measurement provided by a given electrode, comparing against the quality expected from this electrode given its position on the body, electrode type, session type, environment conditions (as described below), previous measurement quality and any other parameters.

For example, on a hot day, user 5 may be perspiring more, thus providing higher quality measurements from the electrodes. On a colder day (i.e. when user 5 is perspiring less, having drier skin in general), some electrodes may be in a higher-perspiration area (and thus provide quality measurements) and some may not requiring use of such a humidity inducing mechanism.

System 100 may also implement moveable, retractable or configurable electrodes. Such electrodes may change their position, amount of pressure on the skin or sub-element configuration (for electrodes which consist of multiple parts).

Such changes could benefit system 100 in a number of ways, such as adapting the electrodes to different body postures and movement patterns so to provide better measurements, moving the electrodes so to make them more convenient to user 5 in various body postures and moving electrodes aside or retracting them so to prevent possible damage to both user 5 and the electrodes (for example when used in an out of session biking scenario and user 5 falls off).

Another benefit is moving electrodes to support the use of different monitoring techniques during different times. For example, when monitoring a sleeping user 5, client coordinator 202 may conserve power by using an EEG (which consumes more power) only intermittently, and may rely on GSR monitoring for the rest of the time. As another example, during long-term monitoring, client coordinator 202 may disable (and move aside) malfunctioning or broken electrodes. It will be appreciated that in this embodiment, client coordinator 202 may access script information from script handler 201 and user information from server system 100 to determine best mode of action to handle situations such as broken or non-effective electrode a sleeping user, low battery power mode etc.

Such electrodes may also employ rhythmic changes so to maintain better electrode positions during various activities in which the body of user 5 performs rhythmic movement (walking, cycling etc.) using information gathered about the movement pattern of user 5 as saved in local database 208.

Electrodes may also be adapted for use by the same wearable element 60 by multiple users (e.g. the same headband used by multiple users with different head size).

Such changes can be effected using micro-motors, electro-magnetic elements, form change affected by heat or current, hydraulic drive, pneumatic drive or actuator or any other mechanical motion inducing means.

Analyzer 206 (possibly engaging server analyzer 134) may determine which movement to make based (for example) on activity type (defined or detected), general user's body parts position reading, motion detection, guidance provided by the running script, measurement information, sensor information, measurement quality analysis, user's historical information, sensor information from sensors installed on the electrodes themselves, environmental conditions or other parameters.

System 100 may also employ multiple electrodes and sensor activator 2031 may select which one to use (with or without moving or retracting the other electrodes) based on conditions described herein above.

Analyzer 206 (possibly engaging server analyzer 134) may also use information gathered from sensors installed on the electrodes (as described herein above), as well as the other data sources noted above, as a factor in determining the level of precision to attribute to each electrode.

As discussed herein above, as part of the interaction between user 5 and system 100, system 100 may apply direct physical effects to the body of user 5, such as vibration, pressure (e.g. buzzing) and temperature change (hot or cold) which may be generated by thermoelectric cooling (using two metals to affect heat transfer), if there is no refrigeration unit available. Hot temperature is easier to generate.

Other direct physical effects may include low-voltage electrical current and odor generation.

It will be appreciated that direct physical effects are typically applied by wearable elements 60 (e.g. a wearable element applies vibration or temperature change to the user). System 100 may also interface with an environment control system (e.g. air conditioning system, smart home) to apply physical effects which do not require direct skin contact, such as changing the room's general temperature or humidity. In this scenario sensor activator 2031 may instruct the control system accordingly.

Direct physical effects may be combined with other instructions or stimuli, for example, vibration may be associated with specific sound effect or music segment.

DPE activator 2032 may apply multiple direct physical effects simultaneously (of the same or different types), and to the same or multiple body elements. For example, DPE activator 2032 may apply hot sensation to one body area and cold sensation to another. Furthermore, DPE activator 2032 may instruct to the pertinent element to apply a vibration direct physical effect to multiple body regions by using multiple vibration engines (inside different wearable elements 60). These multiple direct physical effects may have different strength and parameters (e.g. vibration frequency).

The strength (and effect) of a multiple direct physical effects may depend on the way in which it is applied to the body of user 5. For example, an identical vibration might affect user 5 differently if applied to a general skin area (e.g. the torso), to the hand (via a smart watch) or to the head.

It will be appreciated that DPE activator 2032 may apply direct physical effects during both in session and out of session periods.

Typical direct physical effects uses may be used as a stimulus, to serve as additional sensory stimulus that may be used by scripts (as described in more detail herein below).

System 100 may use a direct physical effect (such as vibration) as a cue for a posthypnotic suggestion. It will be appreciated that that some non-direct physical effect stimuli (e.g. a short audio segment such as strong beep) may also function as a cue for such posthypnotic suggestion. Such a cue may be induced in session, and may be associated with a given posthypnotic suggestion. When the cue is activated out of session, the posthypnotic suggestion is affected. DPE activator 2032 may also activate the cue to reinforce its association with such posthypnotic suggestion.

Some direct physical effect may affect feelings or mental associations in user 5 and thus may be used as a reward system.

For example, cooling the skin (or heating, based on the weather and skin temperature) is generally a good feeling for most people. An effect may be generic (i.e. applicable to all users) or may be adapted to a given user in some way (e.g. by testing the user response to specific direct physical effect options and settings).

Such a direct physical effect may be used implicitly, providing a feeling which is somewhat below the conscious feeling threshold so the user is not aware that such a reward system is used.

Direct physical effects may be used as a notification system. System 100 may include behavior recognition capability (as discussed in more detail herein below), such as in a smoking cessation scenario. System 100 may detect various events, such as user 5 taking a cigarette out of its box, lighting the cigarette and putting it in his mouth. Furthermore, system 100 may be configured to detect and recognize events which are not directly or fully observable by user 5 (such as high blood pressure or uncontrolled shaking). Such recognition may be performed by system 100 in session as well as out of session.

For example, system 100 may perform a noticeable direct physical effect (e.g. a vibration, beep or even a small electrical pulse) upon detecting any of these events. This direct physical effect may provide a notification or warning to user 5, making him aware that he is performing (or about to perform) an action which conflicts with his stated goal (smoking cessation in our case). This may be helpful even if the direct physical effect is not associated with a specific posthypnotic suggest.

Direct physical effect may also be used as a positive/negative feedback mechanism, for example the direct physical effect can be a pleasant sensation (e.g. cooling the skin) or an unpleasant one (e.g. small electrical jolt) creating a positive or negative feedback loop.

Thus, user 5 who (for example) wants to cease smoking may further his goal through positive feedback (receiving a cooling sensation if he doesn't smoke during his lunch break), negative feedback (an electrical pulse whenever he lights a cigarette) or both.

It will be appreciated that this strategy may be combined with a posthypnotic suggestion for which the direct physical effect serves as a cue.

Some direct physical effects may also support or enhance the hypnosis induction stage. For example, applying cold and hot sensation to the wrist or forehead of user 5 may make the hypnosis induction stage stronger. Such an effect may also occur with the use of specific low levels of electrical current.

As another example, sending small electrical pulses to specific muscles may affect them (e.g. make them move), making the script feel "stronger" or more convincing.

A direct physical effect may be coupled with specific sensors which measure the effect of the direct physical effect on the user. For example, when using small electrical pulse, system 100 may test the follow up muscle electrical activity (EMG) in the affected area.

System 100 may also interact with the body of user 5 through one or more implants that are inserted into the body of user 5 though a medical procedure. The implant would typically communicate with system 100 via wireless communication, but may also be physically connected.

Such an implant may be unique to system 100 (i.e. created to uniquely interface with system 100) or an existing implant (performing an unrelated function) which still provides a relevant capability. Such an implant could be temporary (e.g. installed for a specific treatment involving the system for a given duration), long term or permanent.

Such an implant could be passive in nature (i.e. provide only sensing capabilities, such an implanted continuous glucose monitoring sensor for diabetes patients) or active (e.g. implanted insulin pump or other in-body delivery device for any medicine or other substance, or an externally-programmable artificial cardiac pacemaker).

The implant may be completely contained in the body, or have externally visible/accessible parts (e.g. used for communication or to replenish the supplies of the delivered medicine or other substance. The implant may also be most external to the body, such as a "smart tattoo" which is embedded in the skin of user 5.

An implant may be a single function device or provide multiple capabilities (e.g. a monitoring implant capable of monitoring multiple body parameters).

In particular, an implant may interface with the nervous system of user 5, e.g. so to provide reading of information, new input into the nervous system or to block specific nerve communication.

As discussed herein above, the retrieval and initial processing of information from user 5 via wearable elements 60 and non-wearable elements 65 may be performed by client hub 20 before it is passed to system server 10 for further analysis. Furthermore, client hub 20 may also provide instructions to administer direct physical effects according to user 5 behavior as per the pertinent script in use. In an alternative embodiment to the present invention, in which wearable elements 60 and non-wearable elements 65 have a built in client hub 20, information retrieval and processing may be performed on system server 10. Thus a typical "in session" may occur on wearable elements 60/non-wearable elements 65 which may communicate directly with system server 10 bypassing client hub 20.

Reference is now made back to FIG. 5A which illustrates the elements of client hub 20. It will be appreciated that each element may function according to the instructions from the pertinent script in use based on the session in use and the wearable elements 60 and non-wearable elements 65 available.

Information receiver 204 may receive feedback accordingly from the various sensors used by wearable elements 60 and non-wearable elements 65 available. Coordinator 202 may distribute the information accordingly i.e. to information analyzer 206 for general analysis and to system server 10 for further analysis—future integration (with data from additional users), backup and persistence support.

Figure 8:
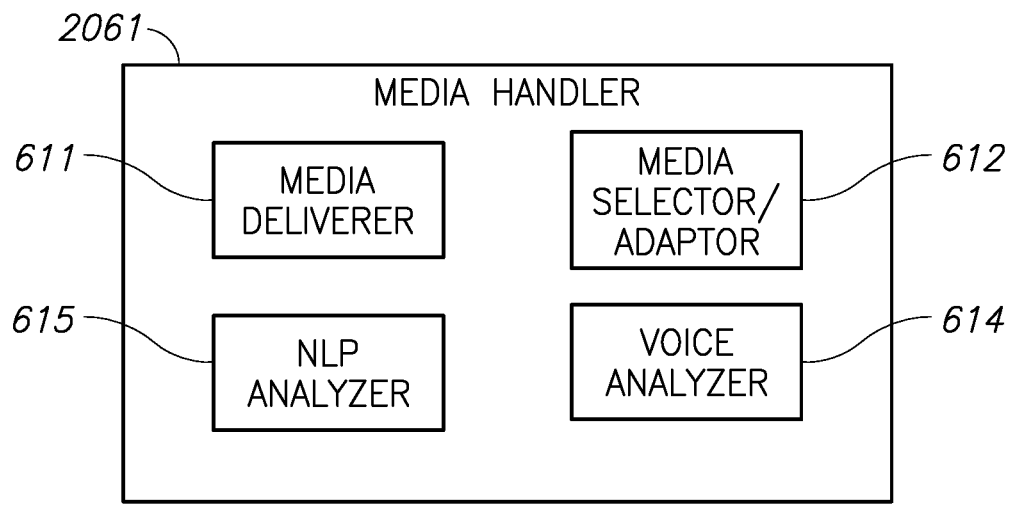
FIG. 8 is a schematic illustration of the elements of the media handler of FIG. 5A, constructed and operative in accordance with a preferred embodiment of the present invention.

It will be appreciated that media segments may be used for instructions and stimuli delivery as part of a session but may also be useful for other purposes such as event notifications, training segments, on-line media based help, UI elements etc. Media handler 2061 may handle all forms of use of media segments as required and as dictated by the pertinent script in use such as delivery of media, selection and adaptation of media segments and pre-analysis of loaded media. Media handler 2061 may further comprise a media deliverer 611, a media selector/adapter 612, a voice analyzer 614 and an NLP analyzer 615 as is illustrated in FIG. 8 to which reference is now made.

It will be appreciated that media segments may be pre-analyzed before use when uploaded to system 100 by media pre analyzer 176. Media pre-analyzer 176 may analyze the audio/video media content upon its uploading into system 100 (via designer store 150 or user script store 160), and its storing in database 140, to extract various features and parameters from it, such as its text content and concepts to be used in the media segment. Media pre-analyzer 176 may create a feature vector for each loaded content segment and may match the content segment with features vector created for user 5 (e.g. matching audio segments containing Jazz music with users which prefer Jazz music) e.g. as part of downloaded script personalization as described below. Such feature vector matching may also be performed later by analyzers 134 or 206

For example, media pre-analyzer 176 may detect different correlations, and use the detected information in script personalization as described in more detail herein below. For example, media pre-analyzer 176 may detect the use of high-pitched sounds in a given audio segment, which are known to decrease EEG's alpha rhythm in this specific user. Media pre-analyzer 176 may also detect that the elements of given content refer to swimming and correlate it with the specific user's fear of water.

Media pre-analyzer 176 may also detect that a given audio segment includes melancholic music which has specific effects on the mood of user 5 or may detect that a given user is more attentive to a quick delivery of speech than to a slow one.

Thus, media pre-analyzer 176 may estimate the effects of a specific media segment on a specific user, even if user 5 has never encountered this media segment before. It will be appreciated that media pre-analyzer 176 may take into account (for example) extracted text content. This may come from keywords or descriptions pre-associated with the media segment or from the text of a text segment (e.g. to be used for text-to-speech generation) which is associated with the media segment in the script. It may also come from a text file providing alternative information for the media segment (e.g. a sub-titles .SRT file for a video segment), from text extracted using a speech recognition engine or from text extracted from images or video frames using OCR.

Media pre-analyzer 176 may also take into account the use of a natural language processing engine on extracted text content so to further extract embedded concepts from the text, graphics or video frame content analysis (e.g. to find the types of entities and activities portrayed in this visual media segment). Media pre-analyzer 176 may also analyze audio segments (for example) using spectrum analysis for tones, rhythm, quality and gain and for indicators of the segment's emotional content.

It will be appreciated that media deliverer 611 may instruct media presenter 2033 to present the selected media to user 5 in the regular manner, as well as using special delivery techniques (such as binaural audio delivery and synchronized delivery).

It will be appreciated that media deliverer 611 may instruct media presenter 2033 to deliver output which may include visual content using still images and video segments, which may be displayed using an embedded screen (built into one of the wearable elements 60 or non-wearable elements 65), an external device screen, a projection system etc. The output may also include virtual reality (VR) and augmented reality (AR), which may be displayed (for example) using specialized VR/AR glasses technology or using regular screens (similar to regular video delivery).

Media deliverer 611 may also use hologram based delivery which may include specific avatars, and may also encompass user 5 (i.e. function not just like a regular UI in front of user 5, but also as a "user environment"). Media deliverer 611 may adapt such delivery to the past responses of user 5 and calibration information (as described in more detail herein below). This may help system 100 (for example) in deepening a particular hypnotic session, allowing higher relaxation etc.

Media deliverer 611 may also instruct media presenter 2033 to deliver audio content via using earphones, speakers or bone-conduction technology. Media deliverer 611 may also use bone conduction technology with external sound generation devices, including devices embedded in or attached to external elements, such as furniture elements. The audio content in such case may not be audible in the regular sense, but is conducted over vibration and bone conduction.

Such audio content may include pre-recorded audio segments and generated audio, which may include text to speech (including multiple narrators and choice of narrator by the user); rule-based synthesized music, audio adapted to external rhythm (as discussed in more detail herein below) and human operator's audio which could be provided (for example) as a premium option.

It will be appreciated, that given the appropriate output devices, media deliverer 611 may also deliver alternate content which addresses the senses, such as touch (e.g. vibration, pressure etc.), temperature, odor or taste.

Media selector/adapter 612 may adapt or select the media segments to the current element/device providing playback capabilities. For example, a script may include playing multiple instances of a given audio segment having different qualities and number of channels (e.g. mono vs. stereo).

Alternatively, media selector/adapter 612 may parameterize media segments such as an audio segment, defined using a client music synthesis format, with the actual media segment generation performed at the client side. This may allow media selector/adapter 612 to select or adapt the media segment for different requirements. This may be required (for example) for selecting or adapting the media segment depending on the element configuration of user 5 (e.g. user 5 is using high-quality earphones in home session setting vs. using a simple single-ear earphone for outdoor sport setting) or may be required for selecting or adapting the media segment to different playback time. Such time constraints may result (for example) from explicit user-set limitation (e.g. the user has limited the session to 15 minutes) or from session section timing issues (e.g. the user has taken longer than planned to enter trance state, and now the remaining time for specific trance-stage content is shorter than planned).

Media selector/adapter 612 may also select or adapt due to conditions resulting from a different session environment (e.g. a session performed in a noisy environment may require using a louder audio segment or a modified version of the given audio segment).

Thus media selector/adapter 612 may provide alternate media of different types altogether. For example, a script may call for use of a video segment to be used by a user without a video display of sufficient quality. In this situation, media selector/adapter 612 may replace the video segment with an audio one either extracted from the video, or a different audio segment altogether.

It will be appreciated that the analysis methods described above may be used to create the features vectors associated with media segments and with specific users. Matching the two vector types may then help media deliverer 611 determine which media files to play, to determine how to play given media files and how to provide alternative media selection i.e. replace a given media file in a script with another one. They may also help media deliverer 611 perform recommendation and unsupervised learning, i.e. use information gather about the response of user 5 to specific media files to learn (e.g. via machine learning) what files to play or recommend in the future.

Thus as media handler 2061 accumulates more indicators on the specific media segment, and on the way it affects various users, the decisions taken based on these indicators may become more precise.

It will also be appreciated that media pre-analyzer 176 may also analyze non-audio/video media, such as specific odor combinations generated by an odor-generation component.

As discussed herein above, media deliverer 611 may employ a variety of specialized techniques for audio segment delivery which rely on the ability to deliver different audio stream to each of the ears. Such techniques may include binaural beats (delivering slightly different beats to the two ears), delay between the two ears, different amplitude between the two ears, double induction (delivering a different message to each ear), different sound layer combination and by using different mixing of audio tracks, channels or sound layers for each ear.

It will be appreciated that some of these techniques may have specific effects on the user/listener (which may vary from person to person), such as affecting specific brainwave frequencies and associated activities, or causing confusion.

The relevant audio content may be standalone audio content or the audio content associated with a given video content segment.

It will also be appreciated that some of the techniques above may also apply to the delivery of video content which include frequency-specific content, and the frequency matches specific brainwave frequencies. This could be done with or without having separate video view for each eye.

Furthermore, media deliverer 611 may employ subliminal messaging embedded in video (and possibly audio) content. Such messages (or other stimuli) may affect the users without being registered in the user's conscious perception.

It will be appreciated media deliverer 611 may also synchronize any audio/video output (regular, binaural or otherwise) in real-time to physiological (or other) rates as detected by the physiological or physical sensors, brainwave reading sensors or environment detecting sensors. Media deliverer 611 may also synchronize general script operation to such synchronization rates, and not just specific media delivery (as discussed in more detail herein below).

Sources of synchronization rate may include brain waves (in real-time), heart rate, breathing rate, movement/running/cycling rate (for out of session use) and behavioral gestures. For example during gym exercise (e.g. weight lifting), media deliverer 611 may synchronize with the user's "lifting pattern". Such a rate could be used not only for media synchronization, but also for script synchronization so that on every completion of the lift the script designer can encourage the user with "very good", "one more time" etc.

Sources of synchronization rate may also include galvanic skin response, eye blinking, eye movement/gaze direction (e.g. for REM detection) and environmental sound. For example, whenever there is substantial repetitive background noise (e.g. on a train), media deliverer 611 may synchronize media delivery or script operation so to match the less-noisy periods. Other sources of synchronization rate are facial expression and muscle relaxation.

Media deliverer 611 may also use any of the other sensors (physiological, physical or otherwise) to provide such synchronization rate.

Analyzer 206 may also record sensor values over stretches of specific activity in order to perform frequency spectrum analysis and detect additional relevant rates in addition to the predefined ones, e.g. rates of "complete sets" in gym exercise, different from the rates of single physical exercises.

Voice analyzer 614 may analyze the voice of user 5, recorded as part of voice UI responses or script responses. In addition to regular voice content recognition (i.e. recognizing what the user said), such analysis may provide information on the state of the user such as the user's emotional state, mental/physiological state information (e.g. anxiety, stress, fatigue), focus/concentration level (e.g. how long it takes the user to respond), sobriety level (e.g. is the user's speech incoherent or slurred) and the confidence level of the user, e.g. strength and resolve in responses, evasiveness, hesitation and similar parameters.

It will be appreciated that voice analyzer 614 may analyze not just the actual speech, but also on delays between utterances, strength of speech and similar metrics. Such voice analysis may also detect some physiological conditions which may be relevant to some scripts, such as coughing, breathing problems, changes to the user's voice related to smoking etc.

Such analysis may be also be based in particular on detecting changes to voice metrics of user 5 as compared to baseline versions of the voice of user 5 recorded during the setup and calibration stages of system 100 as described in more detail herein below. For example, some users will naturally speak very quickly, whereas for some users this could indicate high stress level.

It will be appreciated that voice analyzer 614 may detect the current state of user 5 that a pre-recorded voice segment analysis is aimed at extracting features from the specific pre-recorded segment so to provide information to segment selection, script personalization and other system mechanisms.

Voice analyzer 614 may use advanced voice analysis techniques, such as Mel-frequency cepstral coefficient sound digest for a number or purposes, including analysis of the speech of user 5 (as part of the interaction), analysis of the commands of user 5 (as part of a voice UI), analysis of the script voice segments (e.g. as part of the script pre-analysis process described above) and analysis of speech in the environment of user 5 (which may be used by the system as part of the environment information).

It will be appreciated that such synchronized media delivery is part of the dynamic mode system capability as described in more detail herein below.

Neuro-Linguistic Programming (NLP) was developed by Richard Bandler and John Grindler during the early 1970's as methodology for therapy, communication and the analysis of communication. NLP encompasses multiple tools and skills, and has traditionally been employed by trained therapists.

NLP analyzer 615 may make use of NLP-based analysis of the user 5's communication with the environment to support the progress of user 5 towards his desired goals. This is complementary to behavior analysis and recognition (as described herein below) since behavior recognition allows system 100 to understand what the user does; NLP-based communication analysis allows system 100 to understand the inner elements of the user 5 world based on his communication with other people.

NLP analyzer 615 may record voice and conversations of user 5 (in the environment, with the consent of user 5). This includes continuous monitoring of (e.g. during in session and possibly out of session periods) any such conversations including dialogs with system 100 through the pertinent wearable element 60.

Thus NLP analyzer 615 may distinguish the voice of user 5 from the voices of other people. NLP analyzer 615 may also learn to recognize the sound of an additional person with whom user 5 interacts with on a regular basis such as close family members).

NLP analyzer 615 may separate the voices (user 5 and others) from the environment through blind source separation, known voice recognition or information gathered by the system sensors. For example, NLP analyzer 615 may integrate information about changes in the strength of a given voice and tracking of the head motion of user 5 so to better discern different voices originating in different places relative to the user 5. NLP Analyzer 615 may also make use of multiple recording elements to better detect the position (and identity) of different speakers.

NLP analyzer 615 may convert the recorded and separated voice tracks to text possibly retaining information such as voice level and tonality, so to provide context or "color" information to the extracted text content.

NLP analyzer 615 may also analyze the conversations of user 5 through Natural Language Processing techniques as well as model the collected data so that behavioral issues can be uncovered.

It will be appreciated that system 100 may primarily use NLP meta-model analysis to uncover any underlying issues. The ability to formalize and model behavior of user 5 by NLP, mainly through its meta-model analysis tools (e.g. deletion, distortion and generalization), can suggest different treatments for behavioral difficulties and matching appropriate treatment methods in the form of specific scripts, script parameters or the use of human therapists.

It will also be appreciated that NLP analyzer 615 may be used in conjunction with Combined Therapy Mode (CTM) (described herein below), so that communication between multiple users of system 100 is analyzed from both points of view, and with the information shared between the multiple cooperating scripts.

It will be appreciated that system 100 may be integrated with an on-body device or devices which stimulates the nervous system in some way, and with the stimulation being part of stimuli applied by the script. Such stimulation can be performed by sensor activator 2031 in various parts of the body, and using a range of techniques such as physical stimulation or pressure-based techniques (e.g. similar to the ancient Chinese system of acupuncture) as well as electrical stimulation.

A primary candidate for such stimulation is the vagus nerve, which is accessible in a number of places in the body. In particular, the auricular branch of the vagus nerve is accessible through a device inserted into the ear. There are known methods in the art for non-invasive stimulation (e.g. external neck-area stimulation as described in U.S. Pat. No. 9,248,286 by Simon) as well as minimally invasive stimulation (e.g. 0.1-0.3 mm skin penetration via electrodes in the ear as described in U.S. Pat. No. 9,089,691 entitled "Stimulator for auricular branch of vagus nerve" granted 28 Jul. 2015.

The exact stimulation pattern (power, duration and form) may be controlled by the script and adapted to the response of the specific user. The script may use different stimulation patterns at different times, and adapt the stimulation patterns in real-time during the stimulation session.

As discussed herein above, system 100 may perform continuous monitoring and recording of the movements of user 5, based on the available sensors and possibly including external video view of user 5 if available. This may be done both in session and out of session.

Figure 9:
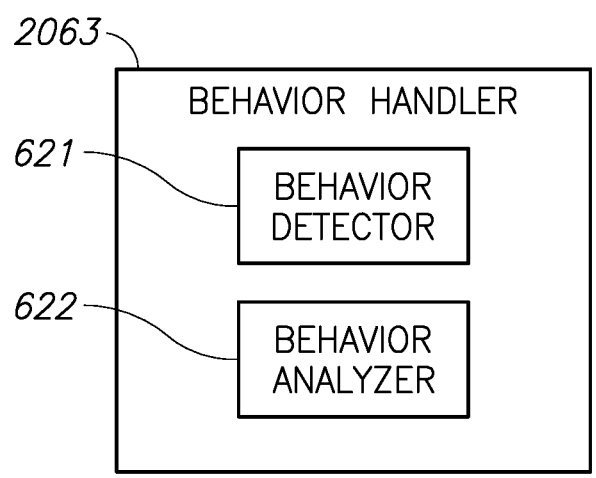
FIG. 9 is a schematic illustration of the elements of the behavior handler of FIG. 5A, constructed and operative in accordance with a preferred embodiment of the present invention.

Behavior handler 2063 may handle readings and analysis of behavior based monitoring. Behavior handler 2063 may further comprise a behavior detector 621 and a behavior analyzer 622 as is illustrated in FIG. 9 to which reference is now made.

It will be appreciated, that depending on the availability and quality of the sensors, behavior handler 2063 may also monitor fine-grain movements (such as tics and muscle twitching) so to build a more comprehensive log of the movements of user 5.

System 100 may also use multiple wearable elements 60 to detect motions of body parts relative to each other, e.g. using two arm bracelets which can measure their relative position and distance to gather further information about arm movement.

Based on the detected motion information, behavior detector 621 may recognize gestures and use them for system control and as part of script interaction.

Behavior detector 621 may also use detected motion to detect indicators of the psychological state of user 5 such as nervousness, sleepiness, focus (which may be correlated to physical response time) etc.

Behavior detector 621 may detect the body language of user 5, e.g. based on body posture, micro-motions etc. as well as analyze major motion, such as the way user 5 walks, runs etc.

It will be appreciated that such information may also help in deducing information from user 5 responses. For example, when system 100 asks user 5 (as part of the in session induction stage as described in more detail herein below) if he feels calm and well rested, user 5 may simply answer "yes" or "no" (through nodding or shaking his head). Behavior detector 621 may be able to detect, based on body language recognition, how calm user 5 is, and possibly recognize that user 5 is saying he is calm when his body language shows that he seems nervous and tense.

It will be appreciated that user 5 may wish to modify a specific type or class of movements, and system 100 may measure such movements to support the relevant script.

For example, user 5 may be suffering from some tics or twitching, and may use a script to help him reduce the amount and frequency of tics, behavior detector 621 may evaluate the progress of user 5 (by measuring the tics or twitching).

Behavior handler 2063 may evaluate the response by user 5 to instructions requiring user 5 to perform specific physical actions (e.g. a "lift your right arm" instruction).

It will be appreciated that behavior handler 2063 may measure the ability (or inability) of user 5 to perform the instructions based on raw motion data received from info receiver 204, and this may indicate the trance levels of user 5 and the success of the hypnotic induction process.

Behavior detector 621 may detect specific higher-level behaviors, including in particular these which the user would like to modify. Such behavior detection may be assisted by additional (non-movement-related) sensors, such as gas sensors which may detect alcohol consumption. It may also be assisted by any video capture of the user himself. Such video capture may be available (out of session) from external sources (e.g. an office computer webcam viewing the user and is connected to the system), or from video camera included in any wearable element 60 though in the latter case system 100 would have to compensate for any variance and instability of the collected video.

Behaviors detectable through motion detection and integrated sensor input may include (for example) smoking (detecting a pattern of lifting hand to mouth), eating (possibly including speed of eating and chewing time), specific sport activities (e.g. walking, running, cycling), body posture (sitting, lying down, standing etc.) and body shaking (stress, nervousness).

Other detectable behaviors are Various Body Focused Repetitive Behaviors (BFRB) such as Onychophgia (nail biting), Excoriation (skin picking), hair picking, teeth grinding, repetitive leg syndrome (RLS) and more.

Behavior detector 621 may detect the activity, and may also detect its basic parameters (e.g. distance traveled during a walking activity, chewing time during eating etc.). Such behavior detection may also be used to suggest area of improvement to user 5 as noted above.

It will be appreciated that system 100 may typically use an expert system (such as server ML engine 136 and client ML engine 2066 as discussed in more detail herein below) to gradually learn the movement patterns specific to the performance of a given activity by the specific user, possibly correlating it with the information gathered on the execution of the same activity by other users.

It will also be appreciated that the behavior detection can be completely automatic or may be user-assisted. In the latter case, user 5 may (for example) inform system 100 whenever he picks up a cigarette (e.g. by using a voice command, a gesture with the "other" hand or by pressing a button on one of the wearable elements 60). System 100 may associate this indication with the other body movements, and so gradually learn to recognize the specific user's physical movements when he picks up a cigarette. System 100 may also include negative indication, i.e. allow user 5 to inform system 100 that its recognition and detection of a given activity is incorrect (e.g. indicate that "this hand lifting is not related to cigarette picking").

Behavior detector 621 may also be able to detect some of these behaviors (e.g., smoking, eating, alcohol consumption etc.) during an out of session period based on their effect on the physiological characteristics of user 5. For example, smoking will raise heart rate, increase skin temperature and cause an increase in EEG alpha bands, with the exact effects varying from user to user but also between different times the analyzed behavior is performed.

It will be appreciated that analyzer 134 may analyze and correlate the behavior and sensor information over time for a specific user in order to create a personalized behavior physiological signature (PBPS) for each such analyzed behavior. Analyzer 206 may then use (for example) the gas sensor data along with the PBPS information to corroborate these events.

Analyzer 206 may also correlate between the measured neurological information and the detected behavior as part of the PBPS so to support concept reading as described in more detail herein below). Thus, system 100 may be able, after gathering sufficient personalized data, to locate specific neurological (and physiological) patterns which may indicate (for example) that user 5 is thinking about smoking. This also allows behavior detector 621 to perform "stealth training" for its behavior detection capability (for the specific user, and possibly assisting the learning for other users as well).

System 100 may also support detailed behavior detection, for example, behavior detector 621 may detect a general behavior (e.g. eating) for which multiple "sub behaviors" exist (e.g. the user is eating different types of foods). This may be required in the scenario where user 5 may want to assist himself in changing his diet to more healthy foods and therefore merely detecting that user 5 is eating may not be sufficient for the script. System 100 may employ the methods described above (e.g. learning system, motion detection, additional sensor integration, video capture, user feedback and PBPS) to detect such detailed behaviors.

It will be appreciated that neurological information of user 5 may be read (with varying degrees of precision and quality) through a number of mechanisms or combinations thereof. These mechanisms may include skin-level measurements as well as these that measure deeper neurological activities. These mechanisms may include electroencephalography (EEG), near Infrared Spectroscopy (NIRS), such as these based on Digital Light Processing (DLP), Functional Magnetic Resonance Imaging (fMRI), possibly using a mobilized version, Galvanic Skin Response (GSR)/Electrodermal Activity (EDA), Blood Volume Pulse (BVP) or Photoplethysmogram (PPG) signal and Electromyography (EMG)/facial electromyography (fEMG).

System 100 may read and integrate the input from multiple sensors so to get the best information regarding the state of the autonomic nervous system and the peripheral nervous system (ANS/PNS).

It will be appreciated that readings are usually made through an EEG, typically performed through electrodes attached to the scalp of user 5. Such electrodes may be part of a dedicated EEG headset, or could be combined with sensors in another element (such as headband or glasses). Different configurations and types of electrodes (as described herein above) may provide different precision and reading quality, possibly requiring substantial follow-up signal processing and improvement. GSR and HRV may also reflect the state of PNS/ANS. For example, relaxation can be determined using both GSR and EEG. Each sensor has its own shortcomings as (for example) GSR changes might not be provide precise information when the user is under the effect of some anti-depressant medication. On the other hand, EEG is harder to measure continuously and may also be harder to process and analyze. Thus, system 100 may produce the best results by combining sensors which complement each other.

Figure 10:
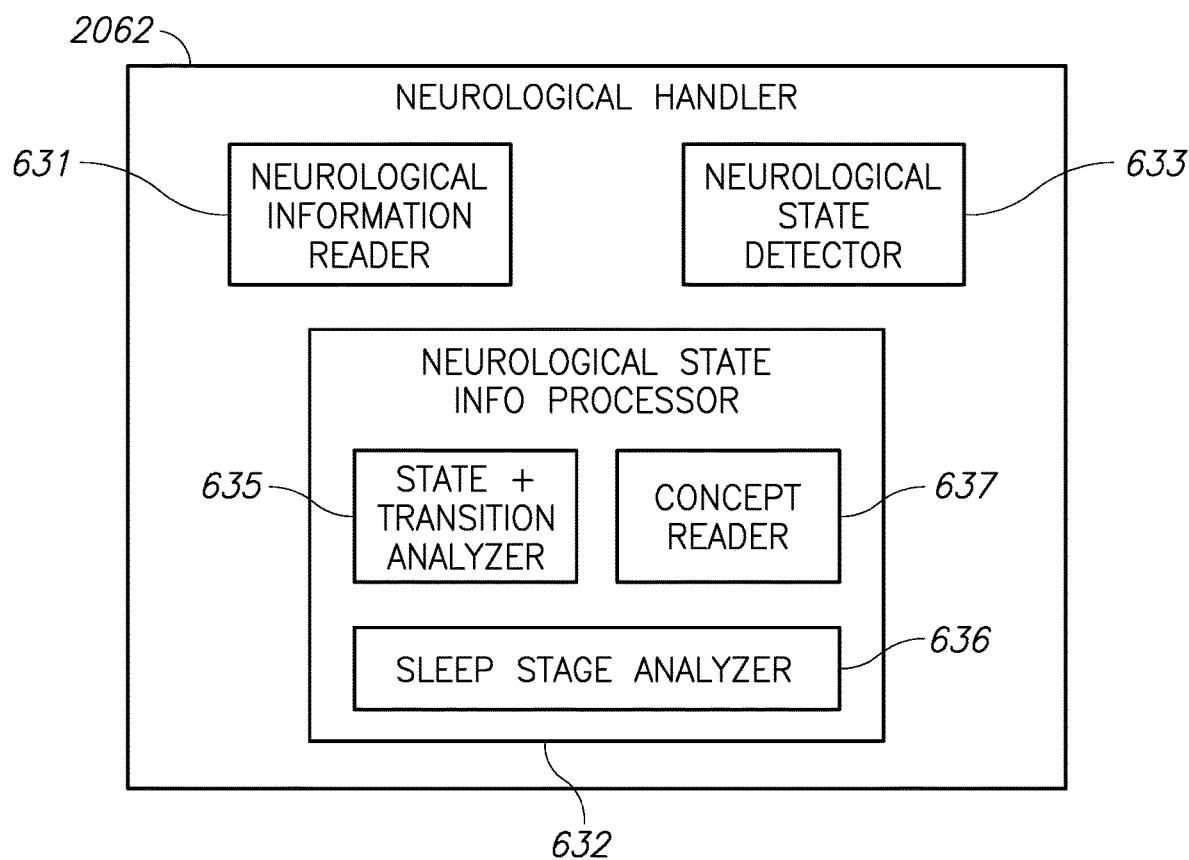
FIG. 10 is a schematic illustration of the elements of the neurological handler of FIG. 5A, constructed and operative in accordance with a preferred embodiment of the present invention.

Neurological handler 2062 may receive neurological readings and process and analyze states accordingly. Reference is now made to FIG. 10 which illustrates the elements of neurological handler 2062. Neurological handler 2062 may further comprise a neurological information reader 631, a neurological state information processor 632 and a neurological state detector 633.

Neurological information reader 631 may receive the results of the readings as described herein above in their raw data format and neurological state information processor 632 may perform pre-processing on the raw neurological information, extracting features which can be used by server ML engine 136, client ML engine 2066 together with statistical modeling algorithms used by integrator 137 or decision maker 2067. Such processing may include noise cancellation algorithms (such as Blind Source Separation (BSS) and adaptive noise cancellation), custom IIR or FIR filters, frequency analysis, regression and curve fitting. The extracted features may include spectrum bands and different bands ratios, as well as artifact information and sleep-stage related markers. Similar processing (e.g. BSS algorithm) may be applied to other sensor inputs as well, so to improve the quality of the information extracted from them.

Figure 11:
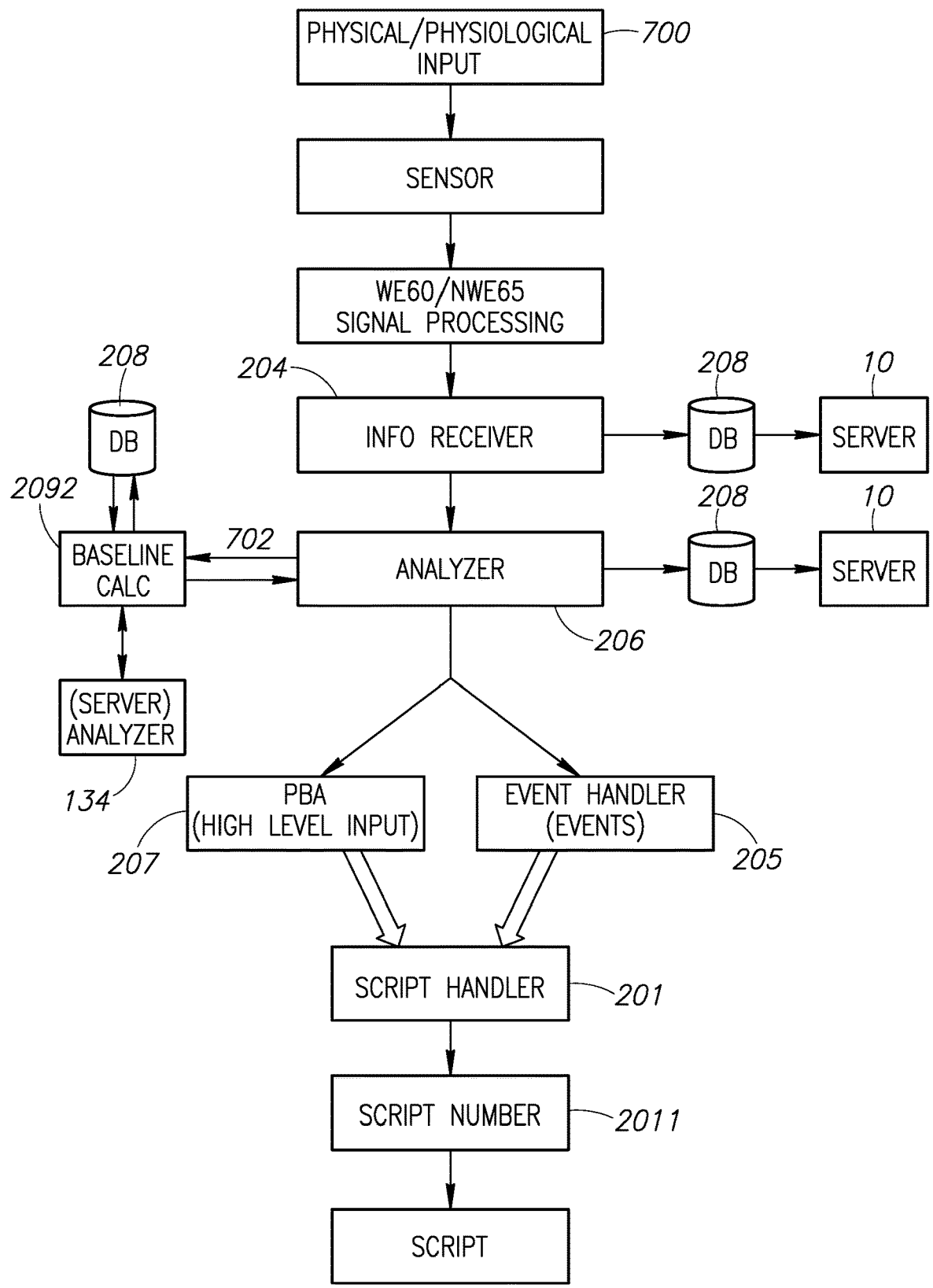
FIG. 11 is a schematic illustration of the flow of sensor input information in the system of FIG. 1, constructed and operative in accordance with a preferred embodiment of the present invention.

Reference is now made to FIG. 11 which illustrates an example process of the above mentioned flow of information for a typical session. Some form of physical/physiological input (such as EEG data) may be received (step 700) by a wearable element 60/a non-wearable element 65/other sensor which may perform signal processing and forward the data to the appropriate analyzer element in analyzer 206 (neurological handler 2062.) via information receiver 204 (step 701). In parallel, this data may also be stored on local database 208 and sent to server 10 for further analysis and storage on database 140. The appropriate elements of analyzer 206 may analyze the data accordingly (neurological information reader 631 and neurological state information processor 632) and either run it through baseline calculator (2092) if it is a new session/user 5 (step 702) or pass it on to PBA 207 for abstraction and event handler/generator 205 to check for any reminders (as discussed in more detail herein below). Finally the abstracted data is given to script handler 201 who may activate script runner 2011 to run the pertinent script accordingly as described in more detail herein below.

Neurological state detector 633 may perform neurological state detection and processing during both in session and out of session periods. The gathered neurological state information includes multiple complex multi-frequency signals which describe the activity in multiple brain areas. As discussed herein above, these signals may include electrical flow information (via EEG), blood flow activity (via NIRS or fMRI) or other types of base signals.

It will be appreciated that there may be multiple sets of measurements with different accuracies which may reflect different combinations of the underlying activity signals (e.g. due to the use of multiple electrodes attached in different positions, or the use of different activity measurement methods as noted above).

Furthermore, the measurement may contain differing amounts of interferences or "noise", which may include (for example) noise resulting from various body functions of user 5, known as artifacts. Such measurement noise may be EOG-induced (due to eye motion/blinking/ . . . ), ECG-induced (Cardiac), EMG-induced (Muscle), etc.

Other interferences may be noise generated by the sensors themselves, interference from the sensor-carrying or other wearable elements 60, environmental noise (e.g. created by nearby electronic equipment), for NIRS readings, interferences created due to motion of skin color effects and sample rate drift correction. It will be appreciated that some of the noise sources above create interferences at specific frequency range, and thus require correction for specific brainwave frequency bands (during the brainwave band separation described herein below).

Neurological state information processor 632 may perform high level processing based on the gathered raw information, and provide the running scripts with high-level information about the neurological state of user 5. Such processing may include state and transition analysis as well as concept reading as discussed in more detail herein below. As discussed herein above, neurological state information processor 632 may further comprise a state and transition analyzer 635 to extract high-level state information from the raw neurological state of user 5, a concept reader 637 to determine user concepts i.e. determine concepts that user 5 is thinking of and a sleep stage analyzer 636 to analyze user sleep patterns.

It will be appreciated that system 100 may perform a pre-processing stage (as described in more detail herein below) employing BSS analysis to reduce the noise and artifacts that may have been introduced into any EEG results. BSS analysis may lower the noise level, and separate different types of data, so noise and interferences do not interfere with the actual analysis of the raw data.

State and transition analyzer 635 may use Evoked Related Potential (ERP) to detect certain brain waves patterns (for the specific user), according to the running script. This may include, for example, performing an averaging process on the signal in certain pre-scheduled "marked" intervals during the running of the script as determined by the script designer or automatically by system 100.

It will be appreciated that a script may include (for example) a specific trigger (e.g., instructions, stimuli or direct physical effect) affecting the user, and may direct system 100 to perform detailed analysis of the response to this trigger in the period following the trigger. Such an analysis may take into account the delay between the trigger and the response.

A script may also make hypnotic relaxation deeper (known as "Hardening") and use suggestions through generated motor imaginary using motor ERP (Event Related Potential) signals. For example, users may be asked to imagine a certain movement—such as hand up, hand down and system 100 may be required to interpret the imagined movement. Such endogenously motor imaginary techniques may be used to test hypnotic susceptibility and improve user's confidence in the system's monitoring capability.

Thus, neurological state information processor 632 may perform script-guided processing of the raw neurological information, which takes into account the different phases and requirements of the running script.

State and transition analyzer 635 may further subdivide any detected rhythmic activity into multiple bands of differing frequency ranges as known in the art (<4 Hz for Delta, 4-7 Hz for Theta, 8-15 Hz for Alpha etc.) in order to measure the signal strength of each band.

These bands are known to correlate to various mental state (e.g. states of awareness, relaxation or resting)—though there is no known precise "trance state signature".

State and transition analyzer 635 may employ several algorithms to distinguish different brain wave bands, including FFT (Fast Fourier transform), STFT (Short-Time Fourier Transform) and wavelets. The STFT and wavelets are especially important when performing time-frequency analysis. State and transition analyzer 635 may use a Morlet wavelet a well as specialized wavelets for ERP analysis.

It will be appreciated that the fine-tuning of this analysis may rely on user-specific frequency analysis based on previous sessions. This may include collected knowledge based on running of multiple scripts from different script providers, i.e. state and transition analyzer 635 may analyze a given user's response to a specific trigger (e.g. a specific vibration direct physical effect with specific strength and duration), and use this information to support other scripts from different providers. State and transition analyzer 635 may also use the information collected for similar by non-identical triggers to infer information for the given trigger.

The analysis may also rely on correlation with additional user parameters, such as current activity type, recent activity history, additional physiological or physical parameters, user profile etc. and correlation with information collected on other users (including selecting other users based on similarity or parameters).

Concept reader 637 may also analyze the raw neurological state information to perform concept reading to determine concepts user 5 is thinking about. Such concepts may include actual abstract concepts, specific words and phrases, non-verbalized thoughts (e.g. images, scents etc.), feelings/emotions and other thought sequences.

Concept reader 637 may perform based on responses to phrases, i.e. concept reader 637 may initiate a specific repeated and covert trigger (e.g. a spoken phrase, an image or a music section), and analyze the specific brainwave patterns, including in particular the transient (non-rhythmic) ones created in response to the specific trigger.

It will be appreciated that such recognition typically requires a long set of training and calibration sessions. It will be appreciated that system 100 may integrate this process into regular sessions so to avoid requiring separate training session.

Thus, concept reader 637 may "feed" user 5 with words and tunes during a normal session and repeat them multiple times (to get high Signal/Noise Ratio of ERP's) without interfering with the user 5 experience (e.g. by combining them with the relevant segments in the "carrier session").

Concept reader 637 may use the gathered response data to determine how and to what extent user 5 perceives certain words. For example, concept reader 637 may determine if an association between a word and an emotional event can be made or not. Moreover, it may also allow system 100 to determine (to a certain extent) if user 5 is cooperating with the session or is in a mind-wandering state of mind, i.e. is the user thinking about subjects raised in the session, and whether he is responsive to stimuli included in the session.

Furthermore, concept reader 637 may attempt multiple variations of the concept trigger including variations of the actual trigger content as well as parameters of its introduction. Based on the detected responses to the various variations, concept reader 637 may create a feedback loop so to improve pattern analysis and find optimal trigger delivery method for further concept reading analysis. Concept reader 637 may explicitly analyze such a feedback loop using (for example) a genetic algorithm.

For example, concept reader 637 may find that (for the specific user), delivering a concept word trigger to the right ear only, using a given playback voice actor, and using a given pitch and voice strength produces the best feedback. In this scenario it may instruct media deliverer 611 accordingly, and media deliverer 611 may adapt some of the media and stimuli in future scripts to adapt them to this specific delivery methodology.

Concept reader 637 may also employ analysis results found when analyzing the same or similar concepts with other users. This may include in particular the results of media pre-analyzer 176 when pre-analyzing script media segments on script loading and user 5 responses to these media segments (as described herein above).

Sleep stage analyzer 636 may analyze the raw neurological information to determine sleep stages and sub-stages. This way, analyzer 206 may characterize states of the consciousness of user 5 and use the high-level resulting analysis to synchronize script activities. Sleep stage analyzer 636 may also rely on additional sensor information as described in more detail herein below.

For example, sleep stage analyzer 636 may inspect the frequency spectrum and detect:

NREM stage 1, characterized by high level of alpha waves.

NREM stages 2, characterized by higher level of theta waves, sleep spindles and k-complexes.

NREM stage 3 (SWS), characterized by higher levels of delta waves. NREM 3 and SWS stages may be regarded as separate stages under some methods of analysis.

In an alternative embodiment, sleep stage analyzer 636 may detect the REM stage may through EOG as well as changes in the level of beta, alpha, heart rate and GSR readings.

Such detection may be based on the user's (stored) historical readings, the readings made though the current and session and information gathered from other users.

For example, during a hypnosis session, user 5 may easily go through a full cycle of sleep stages (i.e. NREM 1, NREM 2, NREM 3/SWS, REM). Through these stages, sleep stage analyzer 636 may determine the exact consciousness state of user 5 and instruct the script accordingly.

It will be appreciated that in addition to the system-user interfaces noted above, system 100 may also include interfaces intended to detect environment information not directly related to user 5 such as environment detector 30A as illustrated in FIG. 3 back to which reference is now made.

These may include, for example, the detection of the environmental noise level, the external light level (e.g. bright daylight, dim room etc.) and the external lighting type, artificial or natural lightings, daylight vs. night time light (e.g. as this may be related to different therapeutic techniques).

There may also be sensors to detect UV exposures levels and the external setting, e.g. in which room is the user located, is there an open television set or other source of distraction in the same room, etc.

Sensors may also detect geographic location, the temperature level of a room and the time of day (as this generally affects the level of awareness of the user and their ability to concentrate.)

Environmental calculator 2064 may detect environmental conditions and calculate an Environmental Condition Estimation (ECE). The ECE parameters may be taken into account while building up script as well as during playback time. For example, a script designer might decide to only play his script in a room with little to no noise, certain lighting conditions or low room temperature.

System 100 may also include advanced environment detection. Environmental calculator 2064 may also try to recognize the type of location the user is in (during an out of session period), and possibly initiate scripts or scripts sections related to this environment. This could include recognizing a gym, a restaurant, a park etc.

It will be appreciated that recognition of the location could be assisted through location services (based on GPS, Wi-Fi information or other sources). Environmental calculator 2064 may also use publically available business addresses information and other sources of geographical information.

Environmental calculator 2064 may also use information gathered from media played in the environment (during an out of session period) and the response of user 5 to them to further enrich the calibration database of the user as described in more detail herein below.

For example, Environmental calculator 2064 may recognize that a given media segment (audio, video, etc.) is playing in the background/environment (e.g. through a subsystem which recognizes played media), and may also recognize the emotional or physiological responses of user 5 to the media segment. User 5 may (for example), become elated to hear some music, become stressed when viewing a horror movie etc.

It will be appreciated, that in an ideal situation, user 5 may perform sessions in a silent environment with no disturbance or background noise. As noted above, environmental calculator 2064 may perform ECE detection and the script may in fact require the environmental noise not to exceed specific maximal noise level.

However, in actual use, user 5 may perform a session in noisy environment. Such environmental noises may include traffic (e.g. aircraft, train or car noise), rain, wind, construction work, children play, background media (radio, TV or played music) noise, emergency vehicle sirens, yelling, background conversations etc.

Environmental calculator 2064 may detect these sounds, analyze them and use a number of ways to mitigate their effect on the on-going session, or actually use the noise to support the session. Such mitigation may be done in a number of ways (which may be combined) including canceling or reducing the noise via adaptive noise cancelation and using the noise to support processes in the running script, e.g. to support deepening of the current session.

It will be appreciated that the detection of noise is done through continuous monitoring and detection by microphones. These could be an integral part of some of the wearable elements 60 (e.g. microphones connected to the headphones) or separate, possibly non-wearable elements 65 (e.g. the microphone included in user 5's smartphone). To support adaptive noise cancelation (as described in more detail herein below, it is preferable to include two microphones located as close as possible to the ears of user 5, or at least one such microphone.

Some of the noises may be highly structured and repetitive (such as the constant background noise heard while riding a train) while some of the noise may be highly unstructured (such as the noise created by a nearby construction project).

To cancel or reduce the noise, noise adjuster 2065 may use the technique known as active noise cancelation (ANC) or active noise reduction (ANR). Noise adjuster 2065 may use the microphones (described above) to capture the environmental noise, and dynamically produces a sound signal having inverted values or shifted phase (or other specialized patterns).

Noise adjuster 2065 may then mix the sound signal with the session sound produced by system 100 (e.g. script media/speech output) so to cancel or reduce the effect of the environmental noise.

In a complementary solution, noise adjuster 2065 may attempt to adapt (rather than cancel or reduce) the environmental noise. Noise adjuster 2065 may analyze the noise, and recognize that it is similar to another sound which is far less disrupting. Noise adjuster 2065 may then use techniques similar to these used in ANC/ANR (e.g. generating a shifted-phase sound track of the difference between the two sounds) so to modify the existing (disrupting) sound to a less disrupting one.

In an alternative embodiment, noise adjuster 2065 may turn this background noise to something relaxing, something that will deepen the state of user 5 considerably, convincing user 5 that every yell will take them deeper and deeper into relaxation. System 100 may convince user 5 that the environmental sound is in fact relaxing and cannot distract user 5, and would thus leverage these sounds to deepen the state dynamically.

Such an approach is best applied to repetitive sounds, and these which can be predicted to some extent. For example, user 5 may perform a session in his home, next to a school which plays a specific (loud) music to announce the beginning and the end of each school break.

Noise adjuster 2065 may perform a personalized calculation for each user which depends on numerous personalized parameters as detailed below the current relaxation state of user 5.

Furthermore, noise adjuster 2065 may experiment with each user to determine when and how to apply this technique. Some users may prefer (and respond better) to ANC/ANR, and some users may respond better to such leveraging of the environmental noises and such preference may depend on the relaxation state or stage, the specific environmental noise and other parameters.

Noise adjuster 2065 may employ a feature extraction engine, which may analyze the surrounding noise and take any of the following factors into account: user specific parameters and information and background noise information, e.g. how much is the current "noise session" repetitive. It may also take into account a target set of "effective" sound sequences, e.g. types (and samples) of background noise which are known to be effective in general, for the current user or for users similar to the current user based on a set of attributes or parameters) as well as the current state of the user (in general, and specific to the current session) and background noise history during sessions, previous sessions, and for the specific time of day or day of week as related to the given user or environment.

Also taken into account may be GPS location and specific environment type (e.g. are we in/near a train station if so, we know we can expect incoming trains at given frequencies or times), traffic information (e.g. from external systems 40 which provide current traffic information such as Google's Ware), time information, known background noise profiles during day/week/month/year (including taking holidays into account) and human speech and speech analysis, for example, in case of emergency the system might promptly end the session.

Based on all of the above, noise adjuster 2065 may estimate the expected profile of the background noise, how much is the noise likely to continue, and how repetitive it would be. Based on this and the parameters above, noise adjuster 2065 may converge on best method (subtract/cancel/modify) or mix of methods to handle the background noise, implement them, test the response and possible modify the method used along the way.

Furthermore, noise adjuster 2065 may make a script-specific determination (e.g. use a given environment noise for deepening in one part of the script and awakening in another part of the script).

System 100 may make similar use of other, non-noise environmental or background conditions, such as vibrations, rain high humidity, cold etc.). This could be as a part of a session (e.g. "The train's constant vibrations reminds you of the rocking cradle you slept in as a baby, making you want to sleep").

This could also be used during out of session, noise adjuster 2065 may integrate information on such background sounds and other (detected) background conditions, activity recognition and other information (such as script running history and time of day) to generate out of session prompts to user 5. System 100 may use such prompts to connect in the user's mind between noticeable external conditions/events and specific desired thoughts, suggestions or moods.

Such out of session prompts may be vocal (e.g. when detecting rain during physical ac, "You feel the rain in your hair, cooling you down and making you run better"), vibration based or based on other forms of delivery available in system 100.

Such prompts may include notifications, reminders or media delivery e.g. instructions or stimuli). They may be generated during a specific activity (e.g. during a physical training session), or may be independent of any activity (e.g. a reminder to the user to engage in specific activity or refrain from one).

Such prompts may be limited to a simple message to user 5 which connects to background condition (sound vibration, humidity). Such prompts may also be associated with a trigger to activate a previous suggestion, e.g. when performing physical activity and the temperature drops, triggering a specific suggestion which helps the user make his physical activity ore intense (which also helps the user warm up).

It will be appreciated that a person does not live in a vacuum and family members and close friends have a tremendous impact on the nervous system, which can affect the physical and emotional state of a user as well as his health.

An example is when a couple is going through some tough period or a crisis. If both partners are using system 100, it is possible (with the consent of both users) to integrate the data collected from both users and to find better scripts and therapy that will serve them both better. As another example, when attempting a health improvement regime, such as a weight-loss diet, smoking cessation or sport activity, it is often advantageous for both partners to engage in a similar regime or activity. This way, each partner could support his partner's progress, and the couple could engage in some activities jointly.

In an alternative embodiment to the current invention, system 100 may be constructed to serve multiple users, or use multiple instances of system 100 interconnected either locally (e.g. through communication means adapted to system 100 instances located closely together) or remotely (e.g. through the common server or directly in using remote peer-to-peer communication).

Moreover, it is possible to treat the couple separately, presenting each partner with a complementary script so to mitigate the difficulties in handling a crisis situation (for example). Alternatively, the couple may take a joint treatment session, with the script possibly including interaction between the two partners. Note that in such situations the scripts (for each partner) may be quite different from each other, but may still cooperate or complement each other.

Another example for such use is pregnancy period, during which system 100 might detect high level of stress in both the woman and the man, and may be able to match and fine-tune treatments for both of them and not just for the woman.

Thus system 100 may support multiple connected users in such way, and not just couples. For example, three friends who decide to start running together may use coordinated scripts between them which would support all three of them in their joint endeavor.

It will be appreciated during out of session periods; system 100 does not allow scripts to run on an on-going basis. Rather, system 100 may define a finite set of events, and may allow scripts to be associated with the occurrence of events and be activated when the event occurs. Such events may include, for example user behaviors (e.g. the user has picked up a cigarette or has actually started smoking one), time triggers (e.g. every day at 12:00) and user-related physical/physiological/mental events detected by the system 100 sensors (e.g. blood pressure rising above a certain level or a certain EEG pattern). This may also include results of higher-level analysis of the sensor input (e.g. detecting that the user is highly stressed based on combined sensor, video and voice analysis).

Such events may also be environment-related (e.g. whenever user 5 enters a restaurant as detected by video or GPS analysis) or a combination of any the above (e.g. the user 5 has opened a refrigerator between 22:00 and 7:00, or user 5 starts smoking a cigarette while his heart rate is above a certain value). The qualifying conditions of such a combination may be referred to as event conditions.

It will be appreciated that client system 25 may maintain a log of all such events stored on local database 208 and may synchronize this information with database 140, even if not associated with a specific script. This way, when associating a script to an event in the future, analyzer 134 may analyze earlier occurrences of the event (i.e. before the association was made) and provide additional analyzed information to the script. This way, for example, a weight loss script would receive information about the eating habits of user 5 and may be able to select the appropriate therapy strategy to use.

It will also be appreciated that event definitions, script/event associations and event logs are all system-level and persistent. User 5 may change a wearable element 60 at any time (e.g. replacing sport activity headband with a different work-time headband) and the definitions/associations/logs should be persistent across the change. It will be appreciated that the information may also be stored on one or more client system 25 elements (including local database 208 in particular), external client side systems 30 or the system server 10 depending on availability. Client system 25 may synchronize the locally stored information with system server 10 whenever an appropriate connection is available.

Based on the triggering of events (and any associated event conditions) script runner 2011 may start running the associated script as described in more detail herein below.

It will be appreciated that there can be multiple scripts associated with different events. Such associations are requested by user 5 or the script (e.g. if user 5 runs a smoking cessation script, the script may request activation during the out of session stage whenever the user picks up a cigarette or smokes one). Script controller 2013 may control the associations to prevent two scripts from running at the same time (e.g. due to the same event), possibly limit an out of session script running time and allowed actions, and provide proper spacing between scripts. System 100 may prompt user 5 to confirm such out of session activation.

When running, the script may instantly alert user 5 (e.g. through a vibration engine or other direct physical effect). The vibration (or other direct physical effect) may also be associated with a relevant post-hypnotic suggestion.

As discussed herein above, system 100 may maintain a global log for each event type in which data is kept and accessible by scripts that are used by user 5. Such logs may typically include additional information about the time, location, circumstances and environmental conditions. This information could later be used to improve in session script behavior and better adapt it to the specific obstacles facing user 5.

It will also be appreciated that the elements of system 100 perform the input (raw data) processing and extraction, and only return the extracted abstract information to the script, which does have access to the raw data.

Thus, a script would not receive exact EEG readings, user pulse information or low-level motion detection readings. Rather the script may receive abstract events ("user is not calm"), possibly with additional abstract parameters (e.g. "user calmness level at 0-100%").

Physiological and behavioral abstractor (PBA) 207 may perform this abstraction based on information collected and analyzed by system as described herein below.

PBA 207 may also handle script outputs. For example, the script may request to "calm the user". PBA 207 may use information collected by system 100 from multiple users on which types of stimuli and signals work best, and which do not, and specific information on the current user. Thus PBA 207 may determine the best way to handle such requests. This could be a highly individualized action by system 100, such as heat direct physical effect for one user 5 or a specific music segment for another user 5.

Alternatively, the script may provide a base output stimulus, but allow system 100 to replace it with alternative segments in some cases.

In an alternative embodiment to the present invention, PBA 207 may allow some scripts to use specific stimulus media in specific points, rather than letting PBA 207 select all media to be played. This could be, for example, a specific stimulus or media segment for which there are specific references in other system output segments.

Thus, PBA 207 may act as an interface layer between the script and the inputs and outputs of the script, translating or analyzing these inputs and outputs as required. As described above, PBA 207 does not typically perform a direct translation, but rather a more advanced form of abstraction/interpretation (on input) or decision.

As discussed herein above, system 100 may guide user 5 through a series of phases which may be repeated as desired to achieve the desired goals. These phases may include in session and out-of-session use, and additional phases supporting these periods.

System 100 may allow user 5 to combine in session and out-of-session periods in any desired manner, e.g. he may perform a number of sessions, and only then use system 100 in the out-of-session mode. Conversely, user 5 may perform a single session, and then use system 100 multiple times in out-of-session mode. User 5 may also mix multiple in session stages, each of which is related to a different script, with out-of-session stages (which may in general relate to multiple scripts as further described below).

Thus the primary activity of system 100 during the out-of-session period is monitoring user 5 so to provide appropriate data to the in session scripts, while possibly activating some of the scripts based on event associations as described herein above.

For example, system 100 may monitor the frequency and circumstances in which a user reaches for a cigarette and the occasions in which he actually smokes one (including environmental, physical, physiological and mental information).

This information could help a smoking cessation script determine when user 5 is tempted to smoke, and when he actually manages to fight this temptation.

As discussed herein above, scripts do not run independently during out-of-session periods. They may be run based on a particular user 5 request (e.g. "I want to fight my smoking habit"). A script may associate script segments with given out-of-session events and conditions under the control of system 100 (e.g. "Activate script segment X whenever user 5 actually smokes/whenever the s pulse rate of user 5 is above X").

Script runner 2011 may operate these script segments when the events and conditions occur, ensuring proper spacing and no-interference between any running script segments (i.e. running them in a managed environment).

It will be appreciated that the entire process may be under high-level control of user 5 (e.g. determining which scripts may operate during any out-of-session period). Such user 5 control may be done on a high level basis (a general setting control panel) or on detail basis (e.g. via a prompt "The script X would like to use smoking detection information—please confirm").

It will also be appreciated that the script segment hooked to a given event may, for example, may perform an effect which is associated with a given suggestion. For example, a smoking cessation script segment may emit a specific audible tone, or perform a vibration direct physical effect, when system 100 detects that user 5 is reaching for a cigarette. This tone or vibration may in turn be associated with an anti-smoking suggestion.

It will be appreciated that in session period may instill and support the desired change in user 5 (be it improvement, mental change or behavior modification). The out-of-session period then serves to reinforce the desired change, provide feedback to user 5 as well as system 100 and may monitor and measure the progress of user 5 to provide information for further sessions. The out-of-session period monitoring may also detect new behavioral or medical issues which did not exist or differ from the previous conditions and an analysis of these changes may trigger specific script sections as required.

Thus system 100 may handle multiple issue types (behavioral, medical, or other areas of change). User 5 may be aware of some of these issues, and may be unaware of others. For example, some issues may be obvious (and externally observable), such as excessive smoking or problems with sport performance and user 5 may is fully aware of them and would like to improve them.

Some issues may still be externally observable but user 5 is not always (or ever) aware of them. Examples may include nail biting, restless leg syndrome etc.

Some issues may be internal to user 5, and not easily observable from the outside, but user 5 may be fully aware of them and would like to handle them. These may include, for example, various types of stress of phobias.

Some issues may not be externally observable, and user 5 may be aware of them or not. Example may include high blood pressure or other "internal" conditions, which are not observable, and user 5 may be aware of them (e.g. through past medical examination), or not at all.

It will be appreciated that for the scenarios where user 5 is not aware of the problem, system 100 may still detect the problem through its sensors and monitoring capability (during both in session and out of session periods). System 100 may try to report on such problems and suggest solutions, in the form of different therapy/script techniques that fit the profile of user 5.

Thus, system 100 may handle issues detected (and suggested) internally that user 5 was not aware of before, as well as other issues that user 5 would like to "tackle" and hence he is aware of.

Figure 12:
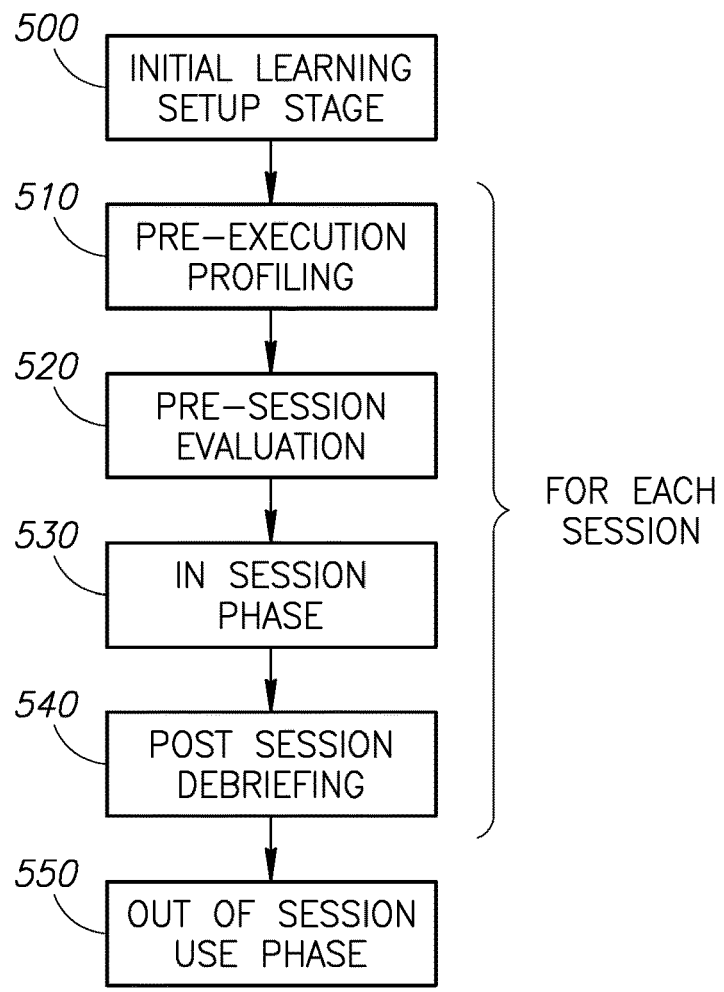
FIG. 12 is a flowchart of the different phases of the system of FIG. 1 for each session and for out of session use, constructed and operative in accordance with a preferred embodiment of the present invention.

Reference is now made to FIG. 12, which illustrates the different phases of system 100 for each session. The phases are:

Initial system learning and setup phase (step 500).
Pre-execution profiling (step 510).
Pre-session evaluation (step 520).
In session phase (step 530).
Post-session de-briefing (step 540).
Out of session use phase (step 550).

It will be appreciated that all phases may include interaction with user 5 through various UI methods (including visual/touch, physical buttons or other controls, voice UI, gesture and expression based) as discussed herein above. However, system 100 may use different methods for different phases and settings (e.g. full alertness, in session trance and outdoors out of session use which all may all require different interaction methods).

These phases are described in more detail herein below. It will be appreciated that for illustration purposes, the description refers to a scenario in which system 100 is used with a smoking cessation script. The description below focuses on a typical system 100 use scenario, which includes a hypnotherapy session in session phase, integrated with applicable use during an out of session phase.

It will be appreciated that system 100 may also be used in a number of alternative scenarios such as a non-hypnotherapy in session use. These may include (for example) sessions performed by a human therapist (such as psychoanalysis, acupuncture or other treatments), sessions perform using various technologies (such as Transcranial Magnetic Stimulation (TMS), heat-based therapy or visual/audio/smell based therapy) and other medical or alternative medicine procedures.

System 100 may also be used in cases in which the in session phase consists of a hypnotherapeutic session performed in conjunction with another treatment, e.g. to replace anesthetics during a medical procedure, or to reduce the side effects of some medical procedure.

System 100 may be used with an in session only mode, without integrating out of session tracking.

System 100 may also be used in out of session only mode, e.g. to monitor the effects of a non-system-managed therapeutic session (hypnotic or otherwise) and to detect new behavioral or medical issues (as discussed herein above).

It will be appreciated that initial system learning and setup phase (step 500 in FIG. 12) is typically performed upon initial access to system 100. However, user 5 may return to this phase under a number of circumstances as discussed in more detail herein below.

It will be appreciated that this part of the phase includes installation, setup, updating/upgrades and testing, including in particular device recognition and connectivity testing.

As discussed herein above, wearable elements 60 and non-wearable elements 65 may be delivered as complete kits (including both hardware and software) while some may require installation (of hardware add-ons and/or software) on external systems such as the Smartphone of user 5.

Furthermore, system 100 may consist of multiple separate devices which may be replaced, and devices may be added or removed as needed. Thus there is a need for system 100 to test the devices themselves, as well as the connectivity between devices (including any newly added devices) to ensure proper functioning.

It will be appreciated that connectivity testing is particularly important with non-traditional device connectivity methods, including in particular body-area networking (i.e. using the body as a signal carrier). Such connectivity testing may include the connection with external devices (non-system elements) which may perform part of the system functionality. System 100 may also provide on-the-fly re-configuration and connectivity detection, allowing later dynamic addition of devices to the system.

Reference is now made back to FIG. 5E which illustrates the elements of setup/config handler 209. Setup/config handler 209 may set up system 100 for a new user 5 the first time he uses system 100. As discussed herein above setup/config handler 209 may further comprise a user profile builder 2091, a baseline calculator 2092, a system tester 2093 and a user trainer 2094.

As described above, system 100 may contain a substantial number of sensors and direct physical effect devices, including devices combining multiple such functions. It will be appreciated that some of these sensors require careful placement or physical configuration. For example, the quality of EEG reading may vary greatly depending on the exact placement and fit of the electrode carrying device (e.g. a headband). This may vary from user to user, e.g. depending on the exact skull shape. Thus, system tester 2093 may require that user 5 test the various sensors and direct physical effect devices, so to make sure they are properly configured and adapted to the specific user User trainer 2094 may train user 5 in the use of system 100 and its elements, through an interactive learning system, on-line tutorial, a video tutorial or other means typically via a built in screen or a screen non-wearable element 65.

It will be appreciated that during the initial learning and setup stage (step 500); user profile builder 2091 may build a psychological and physiological profile of user 5. User profile builder 2091 may collect and store data during an interactive session with user 5 including the selection of issues to tackle (smoking, dieting, self-improvement, etc.), specific goals, personal preferences etc. As discussed herein above, these topics may include issues requested by user 5 as well as those suggested by system 100 (as discussed in more detail herein below). The results from user profile builder 2091 may be also be used by script handler 201 and PBA 207 to provide parameters for the execution of a pertinent script. User profile builder 2091 may also assess any user expectations.

Baseline calculator 2092 may also collect baseline values for the various physiological sensors (e.g. EEG or heart rates) and physical (e.g. motion) in a normal alert state. Such collection may be performed during the entire phase, including in particular during the system learning sub-phase. These baseline values are later used as reference values for the various scripts. Baseline calculator 2092 may modify these reference values based on later out of session measurements. PBA 207 may use this information as described herein above.

User profile builder 2091 may also import any relevant information from external sources and systems 40 (accessible through system server 10) or 30, such as a user medical information, genetic information (when available) etc.

As discussed herein above, system 100 may perform continuous monitoring and recording of the input sensors, this information may be stored on databases 208 and 140 and may describe the state of user 5 over time. It will be appreciated that baseline calculator 2092 may use this data to form a baseline for further measurements. This is performed in particular as part of the initial system learning and setup phase (which provide a canonical baseline set), and later in the pre-execution profiling phase (during which the system runs a system calibration super-script) but continues throughout the use of system 100.

Analyzer 206 may detect that some parameters of the state of user 5 (neurological, physiological, physical or otherwise) are out of the ordinary, and may check values not just against the generic expected values, but also against the specific values for the same user in a similar situation in the past. Analyzer 206 may also compare state parameters against these of other users in the same or similar situations, and may also compare state parameters against each other as well as the profile parameters of user 5 (so to find correlations specific to the given user or to multiple users, including correlations which depend on specific user profile parameters).

The profile parameters used for user correlation (and the resulting baseline calibration) may include various personal parameters, such as the gender, age, etc. of user 5. They may also include physiological (or other) parameters of user 5 not typically measured by system 100, but imported from user 5 reporting or other medical systems. These could include (for example) information about the user 5 medical history and profile, genetic profile, hormone level, psychological profile, external evaluations etc. Some of this information may be fixed whereas some may vary over time (e.g. hormonal measurement parameters).

Analyzer 206 (possibly consulting with analyzer 134) may compare current state parameters values against the baseline information to provide information and guidance to running scripts. These two sets of values are also used by PBA 207 as described in more detail herein above, to determine the processed (abstract) user 5 state values provided as input to the script.

For example, when beginning a session, and before starting the induction process, Baseline calculator 2092 may note the neurological state of the user (e.g. EEG readings), physiological state (e.g. muscle twitching, HRV and GSR) and physical state (e.g. use the motion sensor to detect RLS etc.). Based on this combined information, baseline calculator 2092 may determine whether user 5 is particularly nervous compared to his ordinary state. Baseline calculator 2092 may then provide this information script handler 201 which may (for example) either prevent user 5 from running the script, determine to proceed as usual or modify the script behavior (e.g. add a relaxation sub-script in the beginning of the session). Script handler 201 may also switch to a different script or run the script, but use modified baseline values for some state parameters during running (e.g. use different brainwave value thresholds to determine script transitions).

As another example, analyzer 134 may also deduce that a certain script or script variation is more effective on female users in the age range 20-30 with South American ancestry, but requires different brainwave reading threshold (for given transition points) than the general population. In this scenario, Analyzer 134 may notify script handler 201 accordingly.

As baseline calculator 2092 accumulates additional state and baseline information, it may learn about user 5 and may modify the baseline values for further activities (e.g. "this user moves a lot, so correct the threshold for detection of nervousness").

It will be appreciated that based on the data gathering process described above, Baseline calculator 2092 may perform stealth calibration, executing the calibration process while minimizing (or omitting entirely) any requests for explicit actions by user 5.

For example, the system 100 vendor may create a training model for EEG artifacts removal or for gesture recognition during various parts of the introductory phase of system 100 to be presented to user 5 by user trainer 2094. This way, system 100 may avoid annoying user by requiring him to execute a tiresome training session.

Baseline calculator 2092 together with PBA 207 may also use calibration requirements when evaluating (for example) which media segments to use for various purposes. Thus, baseline calculator 2092 together with PBA 207 may handle a request by the script to "calm the user" by playing different segments of music using other stimulus or direct physical effect altogether) at different times, and so expand the baseline information regarding the responses of user 5.

Thus baseline calculator 2092 together with PBA 207 may experiment, essentially performing an automatically-generated multivariate test, so to find the best way to calm user 5.

It will be appreciated that baseline calculator 2092 together with PBA 207 may run system server 10 or on client hub 20. Baseline calculator 2092 may collect information and updates both databases 208 and 140 with baseline information about each user. Database 140 may also include multiple baseline value together with information about the conditions under which they were gathered, e.g. a baseline heart rate is different between a sedentary session and an out of session physical activity period or during day time vs. night time.

During media playback, the biological/physical sensor values are collected and quantified by analyzer 206 A generic biological baseline is derived as well as a specific baseline that correlates with the type of media that was played.

It will be appreciated that there may be a general baseline that characterizes user 5 while active, resting, stressing etc. and a specific media "baseline" per script/media segment in order to compare and weight each script or partial section of a script. Baseline calculator 2092 may also take environmental values into account so to create multiple baseline versions (e.g. different GSR values depending on the temperature and resulting levels of perspiration).

Integrator 137 may create an initial baseline based on that of other users with similar attributes/profile as described in more detail herein below. Baseline calculator 2092 may also gather baseline data from external sources 40 (such as medical database or specific baseline data collection projects). Integrator 137 may further correlate the baseline of user 5 to that of other users.

It will be appreciated that all data is managed by information analyzer 206 and is used when running multiple scripts, and therefore it is not private to a specific script. PBA 207 may use the stored calibration data and profile information (from local database 208) to process the raw inputs and to provide the script with high-level abstract analyzed information (without providing the actual raw data) as described herein above.

It will be appreciated that once this phase is completed, system 100 has the basic information required for both in session and out of session use.

It will also be appreciated that user 5 may have to return to this phase for example, whenever the system 100 configuration changes or additional external user data is available. In particular, the sensors may have to be re-tested whenever starting a session (as described herein above), but only after primary setup and configuration have been performed in this phase.

It will also be appreciated that the interaction in this phase is mainly controlled by setup/config handler 209 and not by any specific script). However, user 5 may select scripts in this phase to be used in later stages.

It will also be appreciated that system 100 may be configured for joint use of some of the wearable elements 60 and non-wearable elements 65 by multiple users. In this scenario, system 100 may support multiple user identities, with each user having its own user profile, scripts and information, including different calibration parameters and a baseline for information for the same sensor when used by different users.

In this scenario, the physical configuration of system 100 should be such that elements which physically touch the users (electrodes, on-skin wearable elements and other) should all be replaceable (single or multi-use), or built to facilitate their cleaning or sterilization.

During the pre-execution profiling phase (step 510), setup/config handler 209 may run a general-purpose calibration script that determines different parameters needed to run and select scripts. System 100 may later use the collected information for all other scripts.

It will be appreciated setup/config handler 209 may instruct script handler 201 to play the system calibration script to a new user 5 in order for user profile builder 2091 to build a new profile. The calibration script may collect physiological characteristics (such as user's resting pulse, resting breath rate etc.), may play different sub-scripts that include different themes, hypnosis and therapy techniques to user 5 and may and collect information that can be used to determine the impact on the of each sub-script on user 5.

This system-run calibration script may also play possible media segments and possible triggers (which may be generated by media handler 2061 and PBA 207). The calibration script may also try to apply multiple therapeutic techniques, assessing their compatibility and effectiveness on user 5.

It will be appreciated that the collected data gathered by baseline calculator 2092 may be "shared" with other scripts. Though scripts cannot really access this collected data, script runner 2011 may use the collected data indirectly (via PBA 207) to play different scripts optimally. It will be appreciated that this collected data is the one used by PBA 207 to provide abstract high-level events and information to the script (e.g. "the user is not calm" as the user's current heart pulse rate is higher than the one measured when the user is resting).

Setup/config handler 209 may re-run the calibration script (fully or partially) so to confirm various physiological measures which may change over time.

The pre-session evaluation phase (step 520) is performed just prior to the running of the actual session.

Setup/config handler 209 may trigger environment sensor 30A to detect relevant environmental conditions to the pertinent therapy. As discussed herein above, environmental conditions may affect the functioning of the script, and may prevent some scripts from running entirely (e.g. an audio-oriented script may be unusable in a noisy environment).

Environmental conditions may also affect parameters such the running time allocated to the script, the way temperature sensation direct physical effect is applied (heating in cold room, cooling in hot room), the sound stimulus volume level etc.

As discussed herein above, baseline calculator 2092 may perform baseline value recording for use in the upcoming session, receiving the up-to-date values for the various users' physical and physiological measurements. This allows system 100 to further deduce information about the user's physical, physiological and (possibly) psychological state, building an extended and up-to-date profile of the user.

System Tester 2093 may present options of scripts to user 5 to select according to the problem user 5 would like to deal with (e.g. smoking, insomnia, etc.) and providing the user 5 with the means and suitable interface to fine-tune session goals and out of session monitoring. This script selection process may refer to additional parameters provided by user 5 (e.g. problem severity).

It will be appreciated that this phase may involve searching for a script and purchasing it directly from the system 100 vendor, from user script store 160 or other source as discussed in more detail herein below. It will also be appreciated that user 5 may be using system 100 to run multiple scripts, and would need to select which script he would like to run now. It will be further appreciated that the running of the chosen script may depend on environmental conditions and the state of user 5, which may prevent some scripts from running, and may make some scripts less desirable.

As discussed herein above, system tester 2093 may perform an initial calibration of the sensors and elements to the user 5 during the learning and set-up phase (step 500). However, baseline calculator 2092 may also recalibrate and test the various sensors and elements (as well as the connectivity between the elements) just prior to the session. This way, system 100 may ensure that the calibration, setup and connectivity are proper for the immediately following session, and for the current element combination.

Setup/config handler 209 may also perform an additional dialog with user 5 at this stage. This may include gathering any additional information required by user profile builder 2091 to expand the user's profile or otherwise. This dialog may also include specifying any script limitations for the upcoming session that would be enforced on the running script. For example, user 5 may set a time limit (e.g. "allow 30 minutes for the upcoming session") which would be enforced by system 100 on the running script, so even in case of script error or problem. Other limits may be related to medical or other physiological condition of the user ("don't let the script run if my blood pressure rises above X" etc.).

It will be appreciated that setup/config handler 209 may provide these limits to script handler 201 to incorporate into the script, which may plan its work accordingly. Furthermore, script controller 2013 may abort the script (using the nearest interruption point if available as discussed in more detail herein below).

The dialog may also include any parameters or other information needed by the script, e.g. expected session length, information about the expectations of user 5 from the session and any other script-specific information.

It will be appreciated that all information gathered may be recorded in databases 208 and 140, and may be used by the different elements of system 100 and the scripts to affect the upcoming session as well as out of session use and future sessions.

The in session phase (step 530) may include the actual session, and is managed by a single running script, under oversight of script handler 201 (which may enforce some limitations as required by user 5). Even if user 5 has multiple goals and is interested in running a number of scripts, a single session still operates under a single script.

For the smoking cessation example, the in session would include a hypnotic session which induces general suggestions related to smoking cessation, as well as a specific suggestion making cigarettes handling undesirable or unpleasant. The specific suggestion may further be associated with a vibration sensation (a direct physical effect) affected by sensor activator 2031.

It will be appreciated that the various possible sub-stages of the session (introduction, relaxation, attention focusing etc.) are described herein above. However, the composition and sequence of these stages is under control of the running script and different scripts may employ different stages and stage structures. As discussed herein above, the stages are dynamic, and some stages may be skipped, prolonged or shortened.

Furthermore, the in session stages may include stages in which user 5 is in some form or stage of sleep with the script being synchronized with the various sleep stages. Though synchronization of script stages to sleep stages, system 100 may start a session without induction, using (for example) background music to let the user fall asleep and only start the induction when the user has reached a specific sleep phase. System 100 may also perform stages which require a certain sleep stage (so to enter deeper levels of hypnosis) and may also end a session by having user 5 leave the trance state but remain asleep.

Post session debriefing (step 540) maybe be performed by post session de-briefer 210 which may gather user feedback on system 100 in general as well feedback on the specific script and session. Post session de-briefer 210 may forward this collected post-session feedback to script handler 201 to affect follow-up sessions accordingly and analyzer 134/server ML engine 136 to be gathered into a per-script profile collected by system 100 (e.g. are users satisfied with the script? Does it help them?).

It will be appreciated that post session de-briefer 210 may be initiated by user 5, the script itself or script handler 201. It may also be initiated due to information received from server 10 or other users.

The de-briefing may include in particular any problem or distress conditions (as described herein below) encountered during the session possibly inquiring user 5 about them and determining if they should affect the session planning or future script use.

In an alternative embodiment, the de briefing phase may be excluded and system 100 may gather information as part of a relaxation/wakeup or later stage as required without asking user 5 any explicit debriefing questions.

The next phase is the out of session phase (step 550). It will be appreciated that system 100 use during the out of session period may be characterized by longer term use compared to in session use, possibly throughout an entire day, or maybe during certain activities or periods of the day. Furthermore, such use may occur in the typical environment of user 5 (e.g. driving, working or sport activity), typically when user 5 is engaged in various tasks, and possibly moving. Furthermore, system 100 may be used during sleep (e.g. in conjunction with the treatment of some sleep disorders).

Thus, the configuration of system 100 including the selection of elements (especially wearable elements 60) and system use pattern should be as convenient, power efficient, non-intrusive and inconspicuous as possible, and be adapted to mobile and non-focused use.

For example, user 5 may use a more lightweight and less noticeable type of headband, replace the headband with smart glasses or music-headset or earphones (so to be able to provide at least audio feedback during the out of session period). Such a headband may integrate several capabilities such as built-in ear-buds (possibly using bone conduction), multiple sensors (e.g. temperature, humidity, UV, motion etc.), physiological sensors (e.g. EMG, EEG, PPG, smart sensing electrodes etc.), direct physical effect generators (e.g. hot/cold, vibrations, odor etc.), communication modules (e.g. Wi-Fi, BLE, and Bluetooth), UI interaction (through holograms, gestures, buttons etc.) and storage (e.g. using flash memory). Such a headband may be engineered for sleep (requiring comfortable use) as well as waking states.

In another example, user 5 may use full VR glasses for UI in the in session mode, but use AR glasses instead in the out of session mode. In this embodiment, the UI would not replace (and hide) the real world view but only augment it.

Thus, various parts of system 100 (e.g. the scripts, UI, stimuli and direct physical effects) may function differently in various out of session conditions, and system 100 may be required to adapt script elements and content accordingly.

For example, script controller 2013 may instruct media handler 2061 to modify the volume of audio content based on ambient noise level.

System 100 may also modify AR-based content based on what is viewed (e.g. indoors, outdoors, or specific scene. For example, script controller 2013 may move AR content elements so not to hide important parts of the viewed scene.

As discussed herein above, scripts may be interrupted during sessions. Client script handler 201 may provide the ability to detect and deal with different kinds of session interruptions. The detection is performed by the elements of information analyzer 206. Client script handler 201 may offer multiple built-in interruption handling mechanisms.

Script handler 201 may pause a script, may activate a specific script segment (e.g. playing special recordings) and may reevaluate the physiological state of user 5 to determine the point from which the session should continue.

Script handler 201 may also allow user 5 to resume a script (e.g. after the interruption trigger has been handled).

It will be appreciated that a script may define multiple possible interruption points. When such a point is triggered, script handler 201 may instruct the script to perform an orderly exit, possibly including waking the user up from a hypnotic state.

Script handler 201 may register an interruption point and may have a delay period associated with it. Such a delay period may be substantial (i.e. a few minutes), since the orderly exit procedure may take some time.

It will be appreciated that it is the responsibility of the script designer to mark such points in their script and include hints to client script handler 201 on the proper handling and to provide the proper handling method for leaving the script smoothly (e.g. provide a relevant script segment or audio track). Client script handler 201 may require the script to provide a minimal set of interruption points, so the script can always be aborted at a nearby interruption point, taking no more than a given time. Script compiler 171 may enforce this requirement, including checking for minimum duration between the points when processing the script for inclusion in system 100 (e.g. in user script store 160).

Script handler 201 may use the handling method (e.g. playing an audio segment) and the hints that the script designer has provided as well as the current and historical (general and specific to this session) physiological state to tell from where to continue when the session is resumed. It will be appreciated that script handler 201 may be required to repeat some of the script in some cases.

It will be appreciated that an interruption point may be triggered by script controller 2013 in a number of situations, including (for example), upon detection of current or imminent system failure (e.g. problem with the sensors, inter-component connectivity or battery about to run out before the script end etc.). Client hub 20 may pre-evaluate the battery level on the (multiple) system elements involved in a session, so not to start a session if there is insufficient battery charge left in any of the elements to complete the session. Still, a battery may run out due to malfunction, interruptions etc.

An interruption point may be triggered upon detection of a change in the environmental conditions which make the script running impossible or ineffective as detected by environmental calculator 2064 (e.g. running an audio-based script in an environment which suddenly became very noisy and continues to be so for a substantial period of time).

Another trigger is the detection of emotional distress or extreme emotional response in user 5 by information analyzer 206 (e.g. a script mentioning water used by a user with an acute fear of water) as reflected by the EEG and other physiological sensors and the detection of other extreme physiological or physical conditions (e.g. high blood pressure, uncontrollable shaking etc.) which may indicate some kind of mental/physical distress. Script controller 2013 may also interrupt the script even if information analyzer 206 cannot actually detect the underlying media/physical distress by itself, but only its symptoms.

Another trigger is the detection of the user's body exceeding script limitations set by the user himself for the session (as further described above).

Other interruption triggers are the request to abort the script made by the user 5 via an appropriate communication means implemented by system 100 such as an abort key or button, an abort (spoken) "safe word" or gesture or other means which may allow user 5 to safely terminate the script.

Similar to interruption points above, some scripts may also implement suspension points if possible, though many scripts have no such reasonable point. These suspension points may be used in the non-trance parts of a session in case user 5 has to briefly suspend the session but may return to it quickly. They are activated by a user-initiated trigger, and script controller 2013 may resume the session once user 5 returns from the interruption.

In the general case it is highly unlikely that a script can be paused and resumed, as it is very likely that the physiological state of user 5 has changed due to the interruption. Thus, analyzer 206 should quickly reevaluate the state of user 5 based on the physiological parameters before restarting the session.

Information Analyzer 206 may recognize distress conditions during script operation which may include emotional, physiological or physical conditions which may be related to the script operation, content, stimuli, direct physical effects or other effects.

User 5 himself may not be aware of such conditions, e.g. due to conditions involving unobservable internal physiological parameters (e.g. high blood pressure), due to being in a trance at the moment, or due to the distress being of an emotional/psychological nature that user can't consciously recognize or handle.

Post-session de-briefer 210 may log such distress conditions and report them to user 5 via client system 25's UI, so that user 5 is aware of the problem with the given script in order to avoid it in the future (e.g. by not running the script or running a modified or alternate version).

Client script handler 201 may also report the issue to the script designer via script design system 50 together with supporting data about the circumstances (anonymously and possibly subject to approval from user 5) so to help in the script's further tuning and development.

Information analyzer 206 (or possibly analyzer 134) may integrate in session period interactions and out of session period interactions. For example, in the out of system phase, behavior handler 2063 may monitor the motions (or vital signs) of user 5 and attempt to recognize smoking-related behaviors. Thus, when detecting (though behavior recognition) that user 5 is starting to handle a cigarette, analyzer 206 may send this information to event handler/generator 205 which may check to see that there is an out of session script segment associated with the event (e.g. based on an event/ response table stored in local DB 208). If there is, event handler/generator 205 instructs script handler 201 which may activate the script element which determines that a vibration (serving as a cue to a post hypnotic anti-smoking re-enforcement suggestion) is the correct way to handle the situation. The script segment may then instruct DPE activator 2032 to administer a vibration direct physical effect via the relevant wearable element 60.

This would both remind user 5 (at the conscious level) that he should not smoke, and help trigger a suggestion (at the unconscious level) that makes cigarette handling undesirable, though this suggestion may have been activated already by merely touching the cigarette.

It will be appreciated that this reminder may also reinforce the suggestion and associated behavior change, and furthermore serve as a positive or negative bio-feedback loop. For example, system 100 may reward the user with a cool feeling (using cold-generation direct physical effect as described above) for desirable behaviors to be reinforced, and with low-voltage electrical current for undesirable behaviors.

It will be appreciated that for the smoking cessation example, system 100 may also detect (e.g. though a gas sensor) that user 5 has begun smoking, while failing to recognize that the user picked up a cigarette before.

This could be because, for example, behavior handler 2063 has learned how to recognize cigarette picking from a pack in the shirt pocket of user 5, and user 5 has now picked up a single cigarette from his wallet instead.

Thus information analyzer 206 may review the earlier raw motion sensing information (saved for user 5) to recognize which motions user 5 made to pick up a cigarette, and possibly instruct behavior handler 2063 to modify its "cigarette picking-up recognition" filters (adapted to the specific user), so to include the new motion types.

It will also be appreciated that system 100 may also monitor and measure (out of session) the frequency of such (cigarette handling) incidents, and information analyzer 206 may decide to provide this information to the in session script via script handler 201 to be used in the next in session phase (e.g. by modifying the script or adapting it in some way).

Thus the pertinent script may attempt multiple suggestion types, and could modify the suggestion used based on actual results, without relying on subjective (or just imprecise) user 5 reports.

It will be appreciated that in this manner, the out of session phases may act as on-going A/B-test environments, allowing system 100 to dynamically test script (and session) variations and to determine the best result for the specific user. Such testing may also be performed during the in session phase, but such in session testing may be more constrained as the behavior of the in session for user 5 is more controlled (e.g. user 5 will typically not smoke during an in session period, and thus cannot not provide actual feedback to a smoking-cessation script). It should be noted that for some script types (e.g. scripts which deal with issues that user 5 can't consciously control such as high blood pressure or restless leg syndrome), system 100 may very well perform such A/B testing during the in session period as well.

Furthermore, information analyzer 206 may detect additional, related or environmental information about the occurrence of such incidents (out of session) and may use this information to support the improvement process. For example, the analyzer 134 may deduce that user 5 is more likely to smoke in the mornings, or while driving, and locate and therefore information analyzer 206 may instruct script handler 201 accordingly to include this information in the next session an appropriate script or sub-script related to these specific cases.

It will also be appreciated, that in addition to the above, information analyzer 206 may deduce (for example) that user 5 usually reaches for a cigarette when within 5 minutes of reaching a certain level of stress or nervousness, as detected through a physiological measurement (e.g. EEG reading) or external detection (e.g. detection of extensive twitching or fidgeting by the motion detection sensors of system 100).

Information analyzer 206 may receive the information and may notify script handler 201. As a result, the script may include (for upcoming sessions) additional suggestions directing user 5 to relax whenever he reaches this stress level, e.g. by taking a short rest or a brief session of meditation. Such rest should help user 5 avoid the desire to smoke in the first place.

Information analyzer 206 may also directly notify the script designer (via script handler 201 and through system server 10 script design system 50) so that the script designer may create a specific script to handle such cases, possibly including an updated version of the script.

Thus system 100 may then monitor and provide feedback on the secondary relaxation process in parallel with the monitoring and providing feedback on the primary smoking prevention process.

Event handler/generator 205 may provide reminders to user 5 via a suitable interface from "it's time to take your next pill" to "it's a nice weather outside, how about jogging?" It will be appreciated that event handler generator 205 may be activated according to information provided by multiple sources, such as behavior handler 2063 (e.g. "the user is about to smoke" event as described above), information analyzer 206 (e.g. "the user is suddenly very tense based on EEG analysis"), environmental calculator 2064, the system timer of client hub 20, script handler 201 (e.g. "set up a given music in x minutes") or other sources that setup event triggers. In an alternative embodiment, it may also be used by user 5 to set himself reminders.

It will also be appreciated that unlike the reminders provided by existing systems (such as those provided by calendar software, alarm clocks and sport and fitness software), event handler generator 205 may initiate reminders based on external information from external sources to initiate the activity (e.g. the weather forecast and current weather information as provided by Internet services in the jogging example above).

The reminder may also depend on measured information both environmental (from environment detector 30A), location related and user-related (through the various sensors included in the out of session configuration). Thus, for example, event handler generator 205 will not trigger a jogging reminder if it detects that user 5 is particularly tired (e.g. based on an EEG reading or motion detection). The reminder may be subliminal and may invoke a specific suggestion, i.e. the reminder is not a regular explicit (verbal or otherwise) urging, but rather a specific vibration or buzzing which has been associated with a desire to go out and jog. Thus, user 5 may (for example) configure event handler generator 205 (via script handler 201) so that "starting one day after each time I jog, induce me (though suggestion) to go jogging once more if I'm not at work (as defined by GPS), if the weather is good and I'm well rested". The reminder may include an (implicit or explicit) urging to begin a new session when a script requires a series of session. This way, system 100 may handle some of the tendency of user 5 to procrastinate, delay or skip sessions.

Analyzer 134 may analyze and create correlations based on information collected on multiple users (while preserving the privacy and anonymity of user 5), further supporting the goal of user 5 and script functionality.

It will be appreciated that the combination of the phases and in session/out of session interactions as described herein above, may allow system 100 to provide a feedback loop to user 5 and help him to reach his goals, while simultaneously creating an environment which provides a computerized feedback loop to the system's scripts, allowing the scripts to improve their functionality.

It will also be appreciated that the out of session script execution environment may differ from the in session environment. In the in session environment, the script is typically required to conform to a given time frame, but otherwise has full control of system 100 and the full and dedicated attention of user 5, and may operate through a series of stages defined by the script designer.

It will be appreciated that in the out of session environment, there are no predefined stages and durations, and script and script segments may be activated by script handler 201 based on their association with given events and event conditions. Such events could occur at pre-defined times or be based on a given user 5 behavior (e.g. system 100 has detected that user 5 has begun smoking) or a physiological or any other event (e.g. the blood pressure of user 5 has risen above a certain value) as described herein above.

It will be also be appreciated that system 100 may allow a single script to implement both an in session section and an out of session section. Such a script may have multiple entry points, some associated with in session use (e.g. different ways to run the script during in session) and some associated with specific event types in out of session use.

Alternatively, system 100 may implement multiple scripts (for in session and out of session use), and allow them to be associated, e.g. if user 5 runs in session script X, system 100 may follow it with out of session script Y for use following a given event.

Furthermore, if the in session environment is stable, the script can assume that the same configuration of elements (wearable elements 60 and non-wearable elements 65) is used throughout the script execution. However, an out of session script may be constructed so as to support certain degree of element configuration changes mid-run. System 100 may provide the underlying continuity and persistence (as discussed herein above), so that the script may continue running and be notified of the configuration change. The script may determine how to handle the configuration change, e.g. stop running, continue as usual or adapt to the new configuration.

As discussed herein above, system 100 performs low-level processing and only provides the scripts with high-level abstract data (e.g. as provided by PBA 207) and with no access to the low-level raw data. However, system 100 may define certain scripts or script components as privileged (requiring special approval), and allow such scripts specific access to some of the raw data. System 100 may also require user 5 confirmation to such raw data (similar to the "this application wants to use your location data" prompts issued by smartphones for some application).

It will also be appreciated that privileged script components may also provide specialized, complementary or additional functionality. For example, a third party vendor may offer a specific behavior recognition privileged component for some field of activity (e.g. tennis playing) and may allow script vendors to develop multiple tennis playing improvement scripts, while provide common functionality which recognizes specific tennis moves to all such scripts. As another example, components may be created which detect and analyze specific medical conditions. Such components may also create additional system events, which can be used for script segment hooking (in session and out of session). System 100 may also provide a marketplace for such components, privileged or not, as part of designer store 150.

Figure 13:
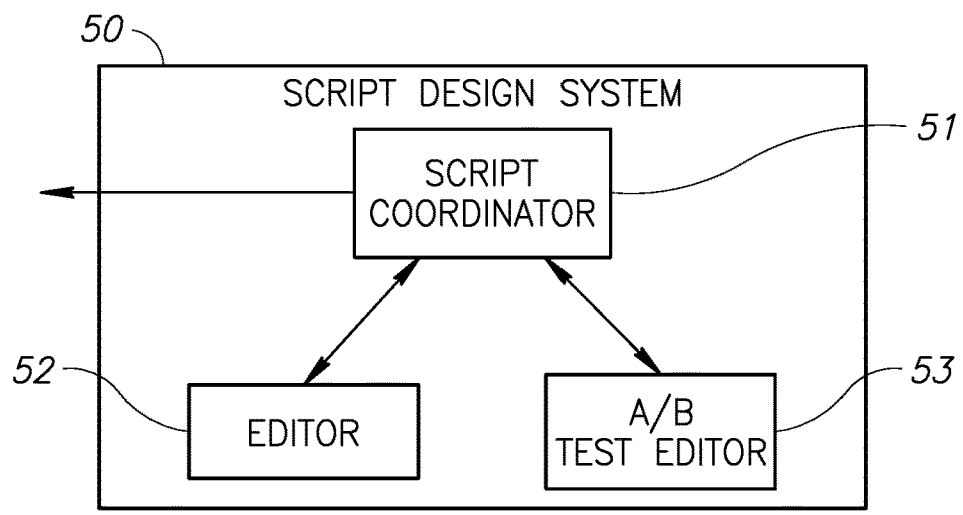
FIG. 13 is a schematic illustration of the elements of the script design system of FIG. 1, constructed and operative in accordance with a preferred embodiment of the present invention.

As discussed herein above, scripts may be created by script designers (which may be regular system users or professional vendors) via script design system 50. Reference is now made to FIG. 13 which illustrates the elements of script design system 50. Script design system 50 may comprise a script coordinator 51, an editor 52 and an A/B test editor 53.

Script coordinator 51 may receive updates from global analyzer 134 regarding information and feedback which may have been gathered during different sessions as described herein above, and which may be relevant to scripts provided by the specific script designer. Editor 52 may provide an interface with a script designer or even a professional (psychologist etc.) which may be required to tweak a script accordingly so to provide the best mode of therapy for a future use of specific scripts (by the current users or new ones). A/B test editor 53 may analyze the results of offering different scripts or script behaviors to different users as a result of a controlled A/B experiment as discussed in more detail herein below. Script design system 50 may also use direct communication with the client hub 20 of a specific script user 5 to provide premium services such as human support or intervention, possibly related to the user of individualized script versions.

It will be appreciated that script design system 50 may be an Internet-based server which provides on-line editing of the scripts and distribution to the users, delivered as Software-as-a-Service (SaaS). Alternatively, script design system 50 may support local editing of scripts and alternative distribution method (physical media based or network-based).

Editor 52 may also be used for the import and inclusion of content segments for use in scripts, and may provide media editing tools for some of the media types.

The system 100 vendor may provide library of sample scripts and script elements. Third party vendors may also provide plug-in elements and other script segments and resources for use by script designers. System 100 may support the use of templates (for complete scripts or script segments), with template being provided by the system 100 vendor or third party vendors. System 100 may offer all of the above (including sample scripts, script elements, plug-in elements, third party offerings/resources and script/segment templates) through designer store 150.

System 100 also may support a media, script or script segment marketplace through designer store 150 and user script store 160, which may include various services to sellers and buyers including searching, marketing and billing services. Such billing may be integrated with the main system server, allowing billing options such as per installation, per use, per session, per hour of use, per results etc. Such billing options may be supported by the results of global analyzer 134, and may be enforced by billing manager 180 (who could moderate a "payment contract" submitted by the script or script element writer, and paid by the user of a script, or another script vendor which uses a script section in his script). As an example of the latter case, a provider of a high-quality hypnosis-deepening script segment may offer his script segment in the designer store 150, and charge other script vendors using his script segment an amount calculated according to percentage of the later script vendor revenues, or a per-minute of use amount. It should further be noted that system 100 may cooperate with third party providers of external designer stores 150 or user script stores 160.

It will be appreciated script handler 201 may run scripts locally and may run with intermittent Internet connectivity or none at all. It will also be appreciated that some back-end script elements may execute on a vendor's server, a third party module and component providers' server or on a script designers' machine. It will be appreciated that scripts may run persistently while the element configuration changes.

System 100 may also support streaming of scripts and referenced media files. Server coordinator 120 may perform such streaming based on earlier analysis of the script (e.g. during script compilation by script compiler 171) which may determine the right schedule and sequence for streaming of the various elements of the scripts, taking into account the structure and alternative paths of the script, the timeline of the script execution, the size of the media files involved together with the possible combinations of system elements (wearable elements 60 and non-wearable elements 65) which receive the streamed media so to minimize element-to-element communication requirements. In particular, the combination of elements used by the current user, and the amount and types of storage available on each of the system 100 elements.

Script compiler 171 may also take into account information specific to the current user, e.g. the execution history of user 5 for the given script as well as information on script execution from other users. For example, the script may contain multiple alternate large-size media files for the same specific purpose. System 100 may determine that only one specific media file is suitable for the specific user, and discard other files so to reduce the compiled script size as part of script personalization when user 5 purchases a script from script store 160.

It will also be appreciated that script may specify the content to be retrieved. This could be though direct links, or through query/content attributes. The actual selection of the media segments to be played may be performed by PBA 207 (based on the script's instructions) as discussed in more detail herein below.

Script runner 2011 may analyze script instructions (arranged in a graph as discussed in more detail herein below) and may execute them by using the real-time collected "hints" provided by the active and non-active sensors and other possible script inputs as described in more detail herein below.

It will be appreciated that non-active sensor data may refer to collected baseline and calibration data as well as collected information about user 5 responses to various script elements. It may also be used to replace data from sensors which are malfunctioning or not available. Such data may also include previous analysis of the collected data as described herein above.

It will be appreciated that each event, condition, or command may be defined and may operate on different low-level inputs, such as gesture, breath, heart-rate, and so on. However, the script may typically operate (and make decisions) based on generic, higher-level inputs (concepts), for example, "relaxation", "non-relaxation", "script is working", "script not working" and so on. Such higher-level inputs are generated by PBA 207 based on information provided by the information analyzer 206 combining multiple sensor inputs (i.e. sensor fusion) and use of the user 5 baseline information.

It will also be appreciated that the EEG, all other sensors and the various author inputs (e.g. comments, expected user response marking and so on) may also be used as hints, once the script file has been downloaded and the instructions are available. The physiological data samples are only used as hints by script runner 2011.

Each line or group of lines in the script is executed based the script transition conditions as discussed herein above (state, neurological state, psychological condition etc.). The granularity of the script is determined by the script designer.

It will be appreciated that neurological information analyzer 206 may maintain a hypnogram to determine the sleep stage and neurological state of user 5, and to record the sleep stage variations specific to user 5.

In this scenario, each edge in the script may have a weight associated with it, so that script runner 2011 may utilize these weights to determine the next playable item in the current playing script. As discussed herein above, the actual media segment selection will typically be performed by PBA 207 based on the collected information for the specific user (i.e. which media segment has the best effect on this user).

It will be appreciated that the script may be constructed using any of the models used in developing event-based systems, including tree-structured, component based, template based, time-line based or otherwise. The following discussion refers to a common implementation involving a tree-structured script, although much of the discussion is relevant to any other script structure. In an alternative embodiment, system script manager 170 may also include a script simulator 172 which may allow a script designer to "debug" his script. Such a facility may allow the designer to play the script with dummy data, a specific user's past data (if access is granted) or anonymized user data (possibly selected according to user selection criteria) and see that the script functionality is correct. In an alternative embodiment, simulator 172 may provide anonymized (or accessed-allowed) data for simulation execution on script design system 50. System 100 may thus protect the privacy of the users 5, while allowing developers to use collected information for testing.

It will also be appreciated that scripts manage the display of outputs (including instructions, media, stimuli and direct physical effects as described herein above) based on rules, inputs and a decision mechanism. The progress/transitions in scripts may be based on direct reading or analysis of any of the following script inputs both in session and out of session. The inputs below may be values (e.g. current heart rate) as well as event-type inputs (e.g. a specific detected motion or behavior).

The inputs may include information collected during the earlier phases (initial system learning (step 500), pre-execution profiling (step 510) and pre-session user evaluation (step 520), the current mode of the user (in session, out of session/awake, out of session/sleeping) and explicit user testing/feedback, e.g. "would you like to continue/abort?", "do you feel sleepy?" etc. Input may be received through any of UI methods detailed above, including in particular natural voice processing and gestures recognition (e.g. head nodding/shaking, hand raising etc.) but may also include traditional input method (e.g. touch screen use). Script updater 2012 may add the inputs to the script accordingly.

Other inputs may include the cognitive/neurological state of the user (e.g. relative brainwave strengths), a specific sleep stage or stage change (e.g. user entered NREM 3 sleep), recognized concepts/emotions (e.g. the user displays a given emotion), physiological sensor input (e.g. low heart rate, slow breathing pattern) and user response to explicit instructions (e.g. "please lift your hand") as recognized (for example) by the pertinent motion detection capability.

Inputs may also include response to the outputs of other scripts (media, stimuli, and direct physical effects) including the exact timing of the response. This may include neurological state changes as well as physiological, physical or other forms of response and user behavior detection including explicit behavior (e.g. "user is smoking") or implicit/unconscious behavior (twitching, shaking of leg/head/body).

Other user related parameters may include reading of the user's body language, timing, including calculations based on desired session length and remaining time, session history, including current/previous sessions and history of the user, including information measured during general interactions, out of session period and other scripts.

Parameters may also include out of session measured information, including relevant behavior information in particular (e.g. how often did the user smoke during the out of session, how effective was a given suggestion during the out of session etc.), collected user baseline information, user profile information (including any medical or genetic information) and information gathered on other users (as relevant to the user and properly anonymized) in particular users related to the current user through the use of the same or similar script, or through similar or related profile information (including medical condition or genetic similarity) together with intervention by user 5/system operator/script designer etc. Parameters may further include script designer hints such as comments associated with tracks, expected user's response marking and so on.

As discussed herein above, PBA 207 may typically process the inputs above and provide the running script with the abstract events (which are analyzed and generalized). However, system 100 may handle some of the inputs differently. For example, some privileged system 100 components may be granted specific access to some raw data (as noted above) and some inputs may be handled completely by system 100 and not be transferred to the script at all. Some inputs may be gathered by system 100 (e.g. in database 208) and provided to the script by PBA 207 only in analyzed, summarized or generalized manner (but not in real time).

Some of these inputs may function as asynchronous input to the script. User 5 may use (for example) hand gestures at any time, and system 100 may determine how and when to interpret or respond to them (e.g. abort or suspend the script, perform a pre-defined asynchronous functionality, send a specific event to the script etc.). Such asynchronous inputs may include (for example) physical sensors, motion/gesture recognition and concept recognition.

As discussed herein above, script design system 50 may maintain a two-way communication and data collection channels between user 5 and the designer or vendor of the script for a number of purposes.

A script may contact its designer via coordinator 51 and the script design system 50 interface in the case of a problem to request possible resolution. It will be appreciated that system 100 may allow a set of designer intervention methods which can be implemented by the script.

The script may also be designed so to include specific hooks/spaces for designer intervention. Such an intervention may be controlled by user 5 who may limit or disable it entirely. Such an intervention may also be a premium service as discussed in more detail herein below.

Script design system 50 may collect performance/session history from script users via system script manager 170 retrieved from database 140 for presentation to the script designer. System script manager 170 may also provide context and relevant profile and user history information to help the script designer improve his script.

It will be appreciated that security/privacy manager 175 may guarantee user privacy/anonymity though limiting the information provided to script design system 50. Alternatively security/privacy manager 175 may allow detailed information access based on a generated random ID (per user/session).

As discussed herein above A/B test editor 53 may provide the script designer with the means to include A/B tests in his script, define A/B population selection criteria (e.g. based on user profile details), manage the A/B test (create, close, accept, suspend, un-suspend, define population etc.). A/B test editor 53 may also support multivariate tests in the same manner.

A/B test editor 53 may provide the summarized A/B testing reports to the designer who may (for example) determine which variant to use or further modify the test. A/B testing may be used in both in session and out of session periods.

It will be appreciated that the actual data structure of a script may consist of a script graph, some of whose nodes contain a decision module which applies a set of probabilities as described below.

As discussed herein above, the edges in the script graph represent branching in the script flow. Such branches may reflect script progress decisions (e.g. "script should move to the deepening session stage or start inducing suggestions"), as well allowing system 100 to adapt the session flow to different users (and provide different experience to each). The decision is typically based on generic conditions such as "the user is focused" (as provided by PBA 207).

Figure 14:
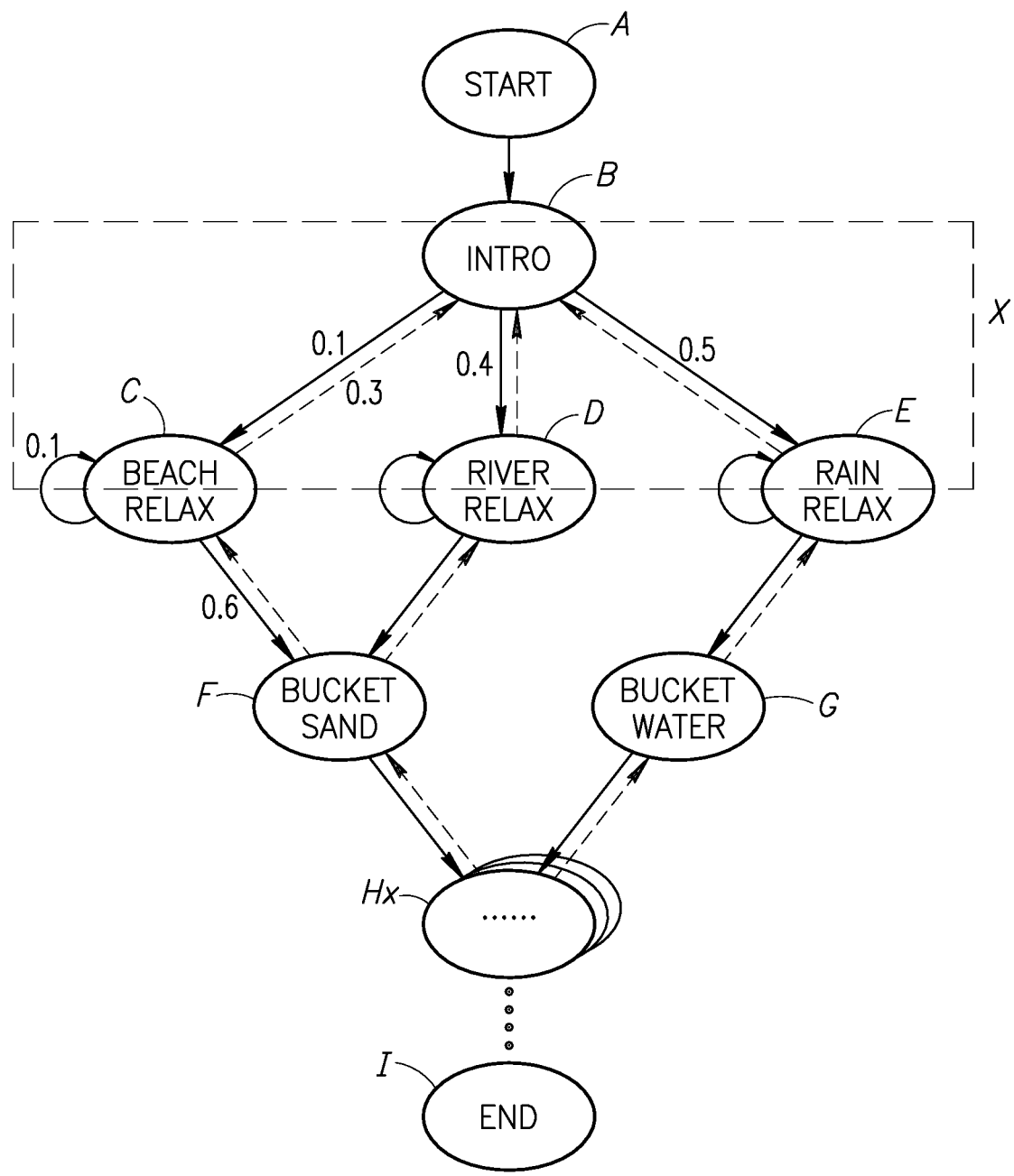
FIG. 14 is a schematic illustration of the structure of a script executed by the system of FIG. 1, constructed and operative in accordance with a preferred embodiment of the present invention.

Reference is now made to FIG. 14 which illustrates a sample script transition graph and its elements. The script consists of nodes (A-I), directional edges between the nodes (e.g. A=>B, B=>A, B=>D and D=>B) and probabilities associated with the edges (such as 0.1 probability associated with the edge B=>C and the 0.3 probability associated with the edge C=>B). It will be appreciated that in FIG. 14 probabilities are only illustrated for the edges starting at nodes B and C.

It will be appreciated that there could be multiple node types. As is shown in FIG. 14, each node represents an interaction with user 5, and may have media and instructions associated with it.

It will be further appreciated that the transition edges can also be between a node and itself (e.g. from node C to itself), signifying that system 100 should re-perform the tasks associated with node C in such case.

For the sake of illustration, forward edges such as B=>C (which represent the script progress) are shown using full lines, whereas backward edges such as C=>B (which represent a problem case in which the script has to return to previous stage) are shown using dash lines.

As can be seen from the example, the sum of probabilities for the different outgoing edges for each node should be exactly 1.0. For example, the outgoing edges from node C have the probabilities 0.3 (C=>B), 0.1 (C=>C) and 0.6 (C=>F), with 0.3+0.1+0.6=1.0.

System 100 would start the session with node A (start) and from it move to node B (introduction). From node B the system would move to one of nodes C (beach relaxation), D (river relaxation) and E (rain relaxation) depending on the outgoing edge probabilities of node B.

Each of the relaxation nodes C, D and E represents a different scene description conveyed to the user to support the relaxation process. System 100 may determine (for example) to transition to node E (rain relaxation) based on the probabilities associated with node B. It should be noted that system 100 may have modified these probabilities, e.g. based on previous experience with this user or other user in past sessions.

Script runner 2011 may then begin executing the instructions associated with node E. System 100 may describe to user 5 how he is standing in the cool rain, feeling the water flow over him and therefore user 5 may become relaxed.

System 100 may analyze the response of user 5 (as measured by the various system 100 sensors and received by information receiver 204) to determine how likely it is that user 5 has reached the appropriate relaxation level. Based on the user 5 response, system 100 and the analysis performed by information analyzer 206 and global analyzer 134 may modify the probabilities associated with the edges associated with node E.

Script runner 2011 may then transition to node F (bucket sand). In this node, system 100 instructs user 5 with a suggestion that he is holding in his stretched hand a bucket and the bucket gradually becomes filled with sand and becomes heavier. If the suggestion affects user 5, his hand would automatically drop (due to the "weight of the sand in the bucket"), confirming the suggestibility of user 5 at this point. If this fails, analyzer 134 may adjust the probabilities, and go back possibly going back all the way to B and selecting a different relaxation method (e.g. node C river relaxation).

Script runner 2011 may also perform non-graph transitions due to various events or exceptions, such as aborting the script (or returning to a specific point) when certain predefined, physiological limits are exceeded (e.g. blood pressure), user 5 has requested the script to stop to suspend it for a short time and a time limit has been exceeded etc.

The script may define computation areas, i.e. set of nodes which are related and affect each other's probabilities. For example, nodes B/C/D/E may be in the same computations area X, since the success of each of the relaxation nodes C/D/E may affect the probabilities of the transitions from B to C/D/E.

As discussed herein above, the mentioned probabilities may be calculated by analyzer 134. Analyzer 134 may use information collected in database 140, including collected historical user inputs (signals and otherwise), computed scripts alternatives paths and as multiple active session signals to build a set of feature vectors. These feature vectors allow analyzer 134 to effectively compute current script transition probabilities which will produce the most effective script paths to taken by client system 25 when the script is run.

Server ML engine 136 may employ multiple machine learning approaches and data representation in each script computation round. The approaches and data representations may include (for example) any of the following or a combination thereof: decision tree learning or regression trees, a supervised learning method that is trained with the most effective feature vector, where each decision tree node tests a feature and eventually used to build the model to predict the target values that are used to discriminate and classify the best script's path. The learning could also be partially leveraged with methods such as KNN, or multi-class Support Vector Machines (SVM's). Another option is artificial neural networks with possibly multilayered feed-forward architecture.

It will be appreciated, that in one possible implementation, the script itself may be represented using a hierarchically structured data description language (such as XML or JSON). Such a language/format may be used to represent the source version of the script, and may also be used (in a binary version) to represent a compiled version of the script.

The script may include a set of such files, with associated media and related files (which are required for the script to run), as well as per-user data files that are needed and generated per user and session.

The main script file may be a static file which is read only and is the file created by the script author, and is the file which includes links to media files. The script may include other dynamic script files that are created and updated on the fly and which are linked by the static file.

As discussed herein above in relation to FIG. 14, each node may be a command, event or condition. It will be appreciated that these node types may be blocking or non-blocking.

For example, the script may want to play a certain track and wait for it to finish before it plays the next, so the graph may include a node specifying a "Play" command in a blocking mode. A similar concept may be applied to events; the script designer may decide that only when user 5 is nodding it can continue with the session, so the designer may use a blocking wait event.

On the other hand, a non-blocking event may be used to stop the script if user 5 starts shaking at any time during the script execution or playing multiple media files simultaneously as confusion script.

It will be appreciated that each command, condition or event may take several parameters, some static (i.e. defined by the script designer) and others dynamic (i.e. inputs provided by the sensors measuring the physical, physiological and other parameters of user 5. Dynamic parameters may be used, for example to synchronize music stimuli playback speed with the user's heart rate or other synchronization rates, to administer a vibration direct physical effect based on the relaxation level (e.g. uses a slower vibration when the user is more relaxed) or to apply a hot/cold direct physical effect to calm the user when he is not relaxed.

It will be appreciated that system 100 may run the same script differently to different people. As a given script will be used by many users, and getting a certain person to a certain state is usually non-deterministic, system 100 may personalize the script. Such personalization may be applied to the transition graph and to the process of applying probabilistic reasoning to the tree edges. The personalization may allow script runner 2011 to determine what to play next, which sounds, event or direct physical effects to operate to route user 5 to the defined state of mind. It will be appreciated that even the same user might like or hate different things at different times.

Decision maker 2067 may use (in real time or off-line) a learning mechanism transition graph to assign probabilities for each option in this regression, and may make decisions on how to maximize the impact of the script on each individual by selecting the best course of action.

It will be appreciated that that the probabilities described herein above are typically pre-computed by decision maker 2067 based on the information provided by the script designer, calibration information of user 5, user preferences and the history of user 5). Decision maker 2067 may also modify the probabilities in real-time, merging them with real-time gathered session real-time information.

The script designer may determine an initial set of edge conditions and probabilities, based on his (generic) knowledge and with the help of recommendations made by system 100. However, the script designer cannot possibly predict the entire range of possibilities and options for each user.

It will be appreciated that decision maker 2067 may use a learning mechanism which is applied to each transition graph for such script decision nodes. At each decision node of the script graph, script runner 2011 may try to predict which branch should be taken based on the user sensor input. To do this, system 100 may use the current and historical data for user 5 as well as different users' history data that determines the likelihood of taking each branch from the current decision node.

It will also be appreciated that ML engine 136 may base its learning on the information gathered by information processor 130 for the current user, as well as information collected from other users.

ML engine 136 may further locate additional users and draw from their experiences to train system 100 for current users. ML engine 136 may locate users based on similarity of data in their user profile/information, similar responses to common patterns (stimulus or otherwise), similar data in session logs (e.g. similar sequences of values of measured physiological parameters), It will be appreciated that system 100 may employ multiple inter-related learning systems. For example, ML engine 136 may train a learning system at the user level and a different one at the script level. Thus, the user level system may acquire knowledge about the specific user (e.g. personalized signatures (PBPS's) for various behaviors) which may be applicable to multiple scripts. In parallel ML engine 136 may train the script level learning system which correlates session results from multiple users of the same script.

ML engine 136 may take into account input values not provided to the script (i.e. measured by system 100 but not actually provided or required by the script), so to gradually improve the ability of system 100 when the script is run.

System 100 may support dynamic mode authoring (as discussed herein above), in which the speed and parameters of various system processes are adjusted based on biological signs or other detected rates that are read from user 5 (through the various system sensors) in real-time as detailed for synchronized media delivery as described herein above.

Script updater 2012 may adjust the script accordingly based on readings from global analyzer 134. Such processes may include (for example): media delivery (audio, video etc.), script direction/branch predilection (e.g. timing script loops according to heart rate or brain waves) and continuous direct physical effect activation (e.g. changing level of heat or cold according to a given rate).

It will be appreciated that the script designer may opt to include certain parts as dynamic while others as static (played as is). Both editor 52 (which specifies the dynamic mode elements) and PBA 207 (which provides the dynamic mode media presented based on directives from script runner 2011) may implement this. It will be appreciated that at the basic level, this capability may allow a designer to specify that a given segment of music will be synchronized with the heart rate or breathing patterns of user 5. As another example, system 100 may recognize the power-lifting rhythm of user 5 in a gym, and provide a vocal encouragement (possibly associated with a suggestion) after every 10 power lifts.

It will also be appreciated that a script may employ continuous change of the played media. Instead of switching complete media segments (e.g. switching to a new music track to get a better trance state), media deliverer 611 may continuously modify played segments and their playing parameters. In this scenario, script controller 2013 may try to correlate changes to the media with changes in the resulting brainwave patterns and other indications detected by the system sensors similar to dynamic mode support described above.

Sample media changes may include changing music speed, volume or bi-aural parameters and having music recorded with multiple tracks and changing different track parameters, track mixing parameters, or just adding or removing tracks.

Thus script controller 2013 may introduce dynamic variations automatically, e.g. via a genetic-algorithm type system which introduces variations (mutations) so to find the best mutation(s) based on the detect trance state and sensors or based on a success criteria defined by the script. It will be appreciated that this genetic algorithm mechanism may unite feedback results from multiple users to locate the best variations.

In an alternative embodiment to the present invention, system 100 may offer human intervention as premium service. The discussion herein above has referred to fully an autonomous script execution by script runner 2011, which does not require human intervention. However, system 100 may allow offering human intervention (e.g. as a premium service). This could be the script designer, the system operator or a fourth party.

It will be appreciated that such intervention may be integrated into the script execution, i.e. the script designer can leave "hooks" or "spaces" for human intervention. The script should be flexible enough to support different time periods and manners of intervention.

The script may include elements which together create a secondary UI dynamically to be used by a human intervenor/operator. These could be a full specification of such UI, or parameters used by the system to generate a UI for use by the intervenor.

Security/privacy manager 175 may allow user 5 to limit or disable script designer intervention (including "intervenor firewall" "only let X intervene on issue Y"). The design may allow a fourth party (non-script designer) to provide human intervention services.

In yet another embodiment, user 5 may allow security/privacy manager 175 to use a relaxed privacy/anonymization policy to system 100, to allow the human intervenor to access specific parts of the detailed user 5 information collected by system 100. Such a relaxed policy may be specified on per-item basis, with user 5 being able to define precisely what items of information are provided in full detail, what in summarized form and what items are not provided.

The relaxed policy may define items of information that could be accessed in real time, and items which could only be accessed post-factum (e.g. after the session) and the frequency of access.

In yet another embodiment, system 100 may support personalized scripts which are designed and adapted specifically for user 5. In this scenario, the system 100 vendor or third party script designers may provide such customization services, tailoring the script to the requirements and characteristics of a specific ordering user.

The customization may be based on an existing script, existing script template or include a specialized script created for the ordering user. User 5 may approve a relaxed privacy/anonymization policy to the system for customized script designer access (as discussed herein above regarding human intervention). User 5 may also allow the customization to be integrated with human intervention by the script customization provider.

It will be appreciated that system 100 may be adapted to support pregnancy and childbirth either for the pregnant women by herself, or in conjunction with additional people supporting the pregnancy and the birth (e.g. the father, or a professional doula/birth companion) as discussed herein above. System 100 may greatly help with the stress inherent to the many phases of the pregnancy and to the birth in particular.

In this scenario, system 100 may include sensors to gather information about delivery and contractions, as well as fetal heartbeats (though not for the purpose of medical diagnosis) and to allow scripts to synchronize to that information. Such information may be gathered directly from the laboring woman, or from existing medical devices which gather birth related information.

Such gathering of information may be performed done using a direct software/electrical interface, by using vision and scene analysis capabilities of system 100 to "read" existing system displays as a human being would do and without requiring a specialized interface. System 100 may include a set of such virtual interfaces (e.g. specific image/display recognition modules) adapted to common medical instruments available in the delivery room.

The information may then be used in conjunction with scripts and hypnosis as usual. A person supporting the childbirth (e.g. a specially trained nurse, assistant doula or the father) may also use system 100, using a script which provides hooks for human intervention as described herein above.

The delivery-related sessions can leverage data that was collected previously during pregnancy and pre-delivery periods to determine what the best treatment is and how to operate. Such data may also include data gathered separately (e.g. from medical examinations performed by an examining physician or laboratory tests).

System 100 may also use a pregnancy/childbirth profile adapted to a specific user and in particular can use a profile gathered from past pregnancies and births of the same user. System may also use a pregnancy profile based on the analysis of pregnancies of other women, possible filtered according to similarity to the using women based on various parameters and attributes.

It will be appreciated that script runner 2011 may ensure that multiple scripts running simultaneously during an out of session phase do not interfere with each other using the methods described below. This may happen, for example, if two scripts (associated with different events) operate due to both events happening.

The script authors may define critical sections—script sections which should not be interrupted. In such a case, script controller 2011 may limit the length of such sections. Script controller 2011 may also force the script author to provide proper handling for such interference. Such limitations may also be verified statically (i.e. when the script is uploaded to system 100) through server script verifier 174 or client script verifier 2014.

Script runner 2011 may also determine script priority according to parameters provided by user 5 and environment calculator 2064. For example, user 5 may run a smoke cessation script in the office and sport encouragement script in the gym. Script runner 2011 may then determine script priority based on location detection by GPS, activity type, user state and sensor reading.

In another embodiment to the present invention, system 100 may provide a number of security-related mechanisms. Server script verifier 174 and client script verifier 2014 may perform automatic identification, analysis and blocking of ill-intentioned scripts. Such blocking may be performed (for example) at upon script submission to the system vendor, upon script compilation by script compiler 171, upon script purchase/download to the user and upon script running.

Server script verifier 174 and client script verifier 2014 may block scripts based on the identification of undesired scripts, or on analysis of the script content. Such analysis may require converting media elements (graphic, video and audio) into analyzable text format, and looking for inappropriate content or methods of delivery. The conversion may be performed via speech recognition engine or an OCR (applied to still graphics or video frames).

Client script verifier 2014 may further implement user-defined limitations and criteria for analysis and possible blocking of scripts starting at the script purchase stage, possibly even filtering the scripts which are offered to user 5 (similar to a motion pictures rating system). This can be done by user 5 himself, or by another user setting up the system (as is done in browsing parental control systems).

System 100 may also be configured to block specific content/media and not entire scripts. Server script verifier 174 and client script verifier 2014 may allow scripts to specify alternative content to that blocked.

As discussed herein above, system 100 gathers substantial information about the physical, physiological and behavioral information of user 5 into log files as described herein above. It will be appreciated that the actual raw data is only saved on the system 100 vendor's servers. The script vendors may only receive limited, analyzed information and a need-to-know basis as provided by PBA 207 or by security/privacy manager 175.

For example database 140 may store a complete record of the location history and motion tracking data for user 5. However, user 5 may only be using a smoking cessation script, which only gets the information on the occasions that user 5 picks up a cigarette or actually smokes. User 5 may also define a retention period for the raw data, after which the data is completely erased, or is "reduced" to a summarized form useful for the classes of the scripts the user is interested in.

Thus system 100 may implement cognitive state alteration techniques (such as hypnotherapy), allowing a user to achieve personal self-improvement or other goals. In particular, system 100 combines wearable and non-wearable hardware and software elements, and interacts with the user during therapeutic sessions as well as non-session periods. The interactions are based on information gathered through continuous monitoring of the user, collected user information and additional sources. System 100 integrates the information gathered during the session and non-session periods and may analyze and use this analyzed information to update scripts in order to improve treatment.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type such as a client/server system, mobile computing devices, smart appliances or similar electronic computing device that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general-purpose computer selectively activated or reconfigured by a computer program stored in the computer. The resultant apparatus when instructed by software may turn the general purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A cognitive state alteration system, the system comprising:
   at least one of: a wearable element and a non-wearable element to measure state or activity of a subject and to provide at least one stimulus to said subject;
   a storage unit to store in session scripts and associated out of session scripts, for cognitive state alteration processes,
   wherein each cognitive state alteration process comprises first and second in session media-based treatment processes and an out of session reinforcement stimulus process between said first and second in session media-based treatment processes, to track said state or said activity and to trigger at least one reinforcement stimulus to reinforce a goal at least for said first in session media-based treatment process, each said in session script and each said out of session script to manage said at least one of: said wearable element and said non-wearable element and wherein a first said in session script manages said first in session media-based treatment process and each said out of session script manages an associated said out of session reinforcement stimulus process for said first in session media-based treatment process; and
   at least one processor implementing a cognitive state alteration unit, said cognitive state alteration unit comprising:
   a script handler at least to run said first in session script and said out of session script associated with a cognitive state alteration process selected by said subject from said storage unit;
   an information analyzer at least to perform analysis of readings of at least one of: said wearable element and said non-wearable element during said selected cognitive state alteration process; said information analyzer comprising:
   a behavior handler to administer said at least one reinforcement stimulus in response to an analysis at least of physical behavior of said subject during said out of session reinforcement stimulus process; and
   an environment calculator to determine state of surrounding environment of said subject during said out of session reinforcement stimulus process and at least to remove any effect on said readings utilized by said information analyzer;
   an integrator to integrate said analysis at least from said selected cognitive state alteration process in said first in session media-based treatment process and said associated out of session reinforcement stimulus process; and
   a script updater to update at least one of said first in session script and said out of session script for said selected cognitive state alteration process in response to said analysis and to said integrated analysis.

2. The cognitive state alteration system of claim 1 and also comprising a de-briefer to collect user feedback information about said first in session script, said out of session script, said first in session media-based treatment process, and said out of session reinforcement stimulus process and wherein said information analyzer comprises:
   a decision maker to make decisions on how to maximize an impact of at least one of said first in session script and said out of session script for said selected cognitive state alteration process based on at least one of said integrated analysis and post session debriefing from said de-briefer; and
   a machine learner to update at least one of said first in session script and said out of session script for said selected cognitive state alteration process based on subject data from any of said first in session script and said out of session script, subject data from multiple subjects using any of said first in session script and said out of session script and multiple subjects using scripts similar to any of said first in session script and said out of session script.

3. The cognitive state alteration system of claim 1 and wherein said non-wearable element is a camera.

4. The cognitive state alteration system of claim 1 and wherein said at least one of: said wearable element and said non-wearable element comprises a sensor to read results of at least one of an EEG (electroencephalogram), a HRV (heart rate variability), an EMG (electromyography) a GSR (galvanic skin response), an ECG (electrocardiogram), and a PPG (photoplethysmogram).

5. The cognitive state alteration system of claim 1 and also comprising an event handler defining events to be responded to for said selected cognitive state alteration process and an output deliverer to activate at least one of: a direct physical effect (DPE) activator, a media presenter, earphones and a wearable screen according said first in session script and said out of session script and in response to said events.

6. The cognitive state alteration system of claim 1 and wherein said information analyzer further comprises at least one of:
  a media handler to handle at least delivery of media to said subject and selection and adaptation of media segments;
  a neurological handler to receive neurological readings and to analyze a neurological state of said subject based at least on said neurological readings; and
  said behavior handler to also detect indicators of a psychological state of said subject.

7. The cognitive state alteration system of claim 1 and wherein an output is at least one of: a stimulus, a media element and an instruction.

8. The cognitive state alteration system of claim 1 and wherein said selected cognitive state alteration process comprises at least one of: hypnosis, meditation, psychoanalysis, psychotherapeutic handling, pregnancy support, combined therapies and nerve stimulation.

9. The cognitive state alteration system of claim 1 and also comprising a neuro-linguistic programming (NLP) analyzer to utilize NLP-based analysis of said subject's communication with a surrounding environment to support the progress of said subject towards desired goals.

10. The cognitive state alteration system of claim 1 and wherein said information analyzer also comprises a physiological behavior analyzer to administer said at least one reinforcement stimulus in response to an analysis of physiological behavior.

11. The cognitive state alteration system of claim 2 and also comprising a script runner to run said first in session script and said out of session script, wherein said script runner causes a transition to a new state upon receipt of an indication of at least one of: sleep stage synchronization, pre-defined neurological states, pre-defined physiological states, timing, including calculation based on desired session length and remaining time and an intervention by at least said subject.

12. The cognitive state alteration system of claim 2 and also comprising a script runner to run said first in session script and said out of session script, wherein said script runner causes a transition to a new state upon receipt of an analysis based on at least one of: user profile information, explicit subject feedback, subject's cognitive or neurological state, neurological state reading, physiological sensors reading, subject behavior detection, post-session feedback from said subject and information from other subjects.

13. The cognitive state alteration system of claim 11 and wherein each said transition has a transition probability associated therewith and said script updater updates said transition probabilities.

14. The cognitive state alteration system of claim 12 and wherein each said transition has a transition probability associated therewith and said script updater updates said transition probabilities.

15. The cognitive state alteration system of claim 3 and wherein said storage unit, script handler, information analyzer, integrator and script updater and de-briefer are implemented on a client/server system.

16. A cognitive state alteration method, the method comprising:

having at least one of: a wearable element and a non-wearable element to measure state or activity of a subject and to provide at least one stimulus to said subject;
  storing in session scripts and associated out of session scripts for cognitive state alteration processes,
  wherein each cognitive state alteration process comprises first and second in session media-based treatment processes and an out of session reinforcement stimulus process between said first and second in session media-based treatment processes, to track said state or said activity and to trigger at least one reinforcement stimulus to reinforce a goal at least for said first in session media-based treatment process, each said in session script and each said out of session script to manage said at least one of: said wearable element and said non-wearable element and wherein a first said in session script manages said first in session media-based treatment process and each said out of session script manages an associated said out of session reinforcement stimulus process for said first in session media-based treatment process;
  running said first in session script and said out of session script associated with a cognitive state alteration process selected by said subject;
  performing analysis of readings of said at least one of: said wearable element and said non-wearable element during said selected cognitive state alteration process, said performing analysis comprising:
    administering said at least one reinforcement stimulus in response to an analysis at least of physical behavior of said subject during said out of session reinforcement stimulus process; and
    determining state of surrounding environment of said subject during said out of session reinforcement stimulus process and at least removing any effect on said readings utilized by said performing analysis;
  integrating said analysis at least from said selected cognitive state alteration process in said first in session media-based treatment process and said associated out of session reinforcement stimulus process; and
  first updating at least one of said first in session script and said out of session script for said selected cognitive state alteration process according to results of said integrating and said performing analysis.

17. The cognitive state alteration method of claim 16 and also comprising collecting user feedback information about said first in session script and said out of session script, said first in session media-based treatment process and said out of session reinforcement stimulus process and wherein said performing comprises:
  making decisions on how to maximize an impact of at least one of: said first in session script and said out of session script for said selected cognitive state alteration process based on at least one of said integrating and said collecting; and
  second updating at least one of said first in session script and said out of session script for said selected cognitive state alteration process based on subject data from any of said first in session script and said out of session script, subject data from multiple subjects using any of said first in session script and said out of session script and multiple subjects using scripts similar to any of said first in session script and said out of session script.

18. The cognitive state alteration method of claim 17 and wherein said running comprises:

third updating each said in session script and each said out of session script from updates from said first updating and second updating.

19. The cognitive state alteration method of claim 16 and also comprising defining events to be responded to for said selected cognitive state alteration process and activating at least one of: a direct physical effect (DPE) activator, a media presenter, earphones and a wearable screen according to each said in session script and each said out of session script and in response to said events.

20. The cognitive state alteration method of claim 16 and wherein said performing analysis further comprises at least one of:
    handling at least delivery of a media to said subject and selection and adaptation of media segments;
    receiving neurological readings and analyzing a neurological state of said subject based at least on said neurological readings; and
    said monitoring movements of said subject to also detect indicators of a psychological state of said subject.

21. The cognitive state alteration method of claim 16 and wherein an output is at least one of: a stimulus, a media element and an instruction.

22. The cognitive state alteration method of claim 16 and wherein said selected cognitive state alteration process comprises at least one of: hypnosis, meditation, psychoanalysis, psychotherapeutic handling, pregnancy support, combined therapies and nerve stimulation.

23. The cognitive state alteration method of claim 16 and wherein said running comprises causing a transition to a new state upon receipt of an indication of at least one of: sleep stage synchronization, pre-defined neurological states, pre-defined physiological states, timing, including calculation based on desired session length and remaining time and an intervention by at least said subject.

24. The cognitive state alteration method of claim 23 and wherein each said transition has a transition probability associated therewith and said first updating comprises updating said transition probabilities.

25. The cognitive state alteration method of claim 16 and wherein said running comprises causing a transition to a new state upon receipt of an analysis based on at least one of: user profile information, explicit subject feedback, subject's cognitive or neurological state, neurological state reading, physiological sensors reading, subject behavior detection, post-session feedback from said subject and information from other subjects.

26. The cognitive state alteration method of claim 25 and wherein each said transition has a transition probability associated therewith and said first updating comprises updating said transition probabilities.

27. The cognitive state alteration method of claim 16 and also comprising utilizing NLP-based analysis of said subject's communication with a surrounding environment to support the progress of said subject towards desired goals.

28. The cognitive state alteration method of claim 16 and wherein said performing analysis also comprises administering said at least one reinforcement stimulus in response to an analysis of physiological behavior.

* * * * *